United States Patent

Ohwa et al.

Patent Number: 6,022,906
Date of Patent: Feb. 8, 2000

[54] α-AMINOACETOPHENONE PHOTOINITIATORS

[75] Inventors: Masaki Ohwa, Kobe; Hitoshi Yamoto, Takarazuka; Jean-Luc Birbaum, Higashinada-ku; Hiroko Nakashima, Toyonaka; Akira Matsumoto, Asahi-machi; Hidetaka Oka, Takarazuka, all of Japan

[73] Assignee: Ciba Specialty Chemicals Corporation, Tarrytown, N.Y.

[21] Appl. No.: 08/982,147

[22] Filed: Dec. 1, 1997

[30] Foreign Application Priority Data

Jun. 12, 1996 [DE] Germany ............................... 96810854

[51] Int. Cl.$^7$ ........................... C08F 2/50; C07C 221/00; C07D 265/32; G03C 1/175
[52] U.S. Cl. .................................. 522/8; 522/15; 522/16; 522/17; 522/18; 522/33; 522/34; 522/36; 522/39; 522/75; 522/81; 523/160; 427/510; 427/511; 430/281.1; 430/286.1; 430/269; 564/342; 564/340
[58] Field of Search ................................ 522/34, 36, 39, 522/40–46, 8, 15, 16, 18, 7, 75, 81, 17, 33; 430/281.1, 286.1, 269; 544/87, 175, 162; 523/160; 427/510, 511; 564/342, 340

[56] References Cited

U.S. PATENT DOCUMENTS

| | | | |
|---|---|---|---|
| 4,307,182 | 12/1981 | Dalzell et al. | 430/339 |
| 4,582,862 | 4/1986 | Berner et al. | 522/14 |
| 4,992,547 | 2/1991 | Berner et al. | 544/162 |
| 5,077,402 | 12/1991 | Desobry et al. | 544/87 |
| 5,124,235 | 6/1992 | Fukui et al. | 430/281 |
| 5,541,038 | 7/1996 | Ohta et al. | 430/281.1 |
| 5,698,285 | 12/1997 | Kojima | 428/65.2 |

*Primary Examiner*—Susan W. Berman
*Attorney, Agent, or Firm*—Luther A. R. Hall; David R. Crichton

[57] ABSTRACT

Compounds of the formulae I, II, III and IV

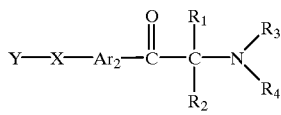 (I)

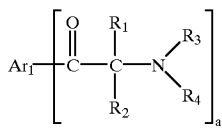

(II)

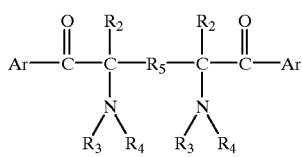

(III)

(IV)

wherein Ar for example is a phenyl, biphenyl or benzoylphenyl group, which is unsubstituted or substituted; $Ar_1$, for example, has the same meanings as Ar; $Ar_2$ is inter alia phenyl; X may be a direct bond; Y hydrogen, etc.; $R_1$ and $R_2$ for example $C_1$–$C_8$alkyl; $R_3$ inter alia hydrogen or $C_1$–$C_{12}$alkyl; $R_4$ is inter alia $C_1$–$C_{12}$alkyl; or $R_3$ and $R_4$ together are $C_3$–$C_7$alkylene; $R_5$ is for example $C_1$–$C_6$alkylene; and Z is a divalent radical; provided that at least one of the radicals Ar, $Ar_1$, $Ar_2$, $Ar_3$, $R_1$, $R_2$, $R_3$, $R_4$, $R_5$ or Y is substituted by 1 to 5 SH groups, or provided that Y contains at least one —SS— group, are photoinitiators for the polymerization of ethylenically unsaturated compounds.

27 Claims, No Drawings

α-AMINOACETOPHENONE PHOTOINITIATORS

The present invention is directed to new α-aminoacetophenone compounds, compositions containing these compounds and the use of the compounds as photoinitiators.

α-Aminoacetophenone compounds are known as photoinitiators for radical photopolymerisation reactions. Such compounds are, for example, disclosed in U.S. Pat. Nos. 4,582,862, 4,992,547 and 5,077,402. In U.S. Pat. No. 5,541,038 α-aminoacetophenone compounds are described to be useful in combination with dialkoxyacetophenone compounds for the production of printing plates.

In photopolymerization technology there still exists a need for reactive, easy to prepare and easy to handle photoinitiator compounds.

It now has been found, that compounds of the formula I, II, III and IV

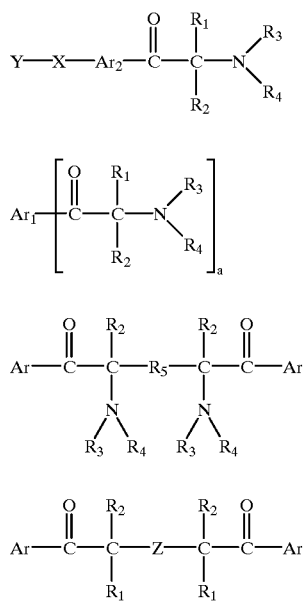

wherein
a is an integer 1, 2 or 4;
Ar is a phenyl, biphenyl or benzoylphenyl group, which phenyl, biphenyl or benzoylphenyl group is unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —$OR_7$, —SH, —$SR_8$, —$SOR_8$, —$SO_2R_8$, —CN, —$SO_2NH_2$, —$SO_2NH(C_1$–$C_4$alkyl), —$SO_2$—N$(C_1$–$C_4$alkyl)$_2$, —$NR_9R_{10}$, —$NHCOR_9$, or by a group of the formula V,

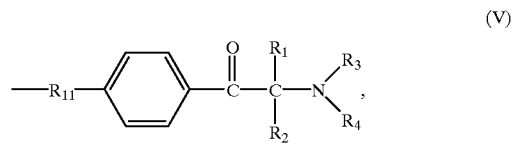

or Ar is a group of the formula VI or VII

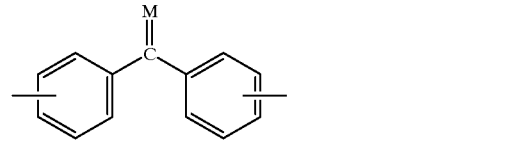

$Ar_1$ if a is 1 has the same meanings as Ar;
if a is 2, $Ar_1$ is a divalent aromatic radical of the formula VIII or VIIIa (VIII)

(VIIIa)

if a is 4, $Ar_1$ is a tetravalent aromatic radical of the formula VIIIb

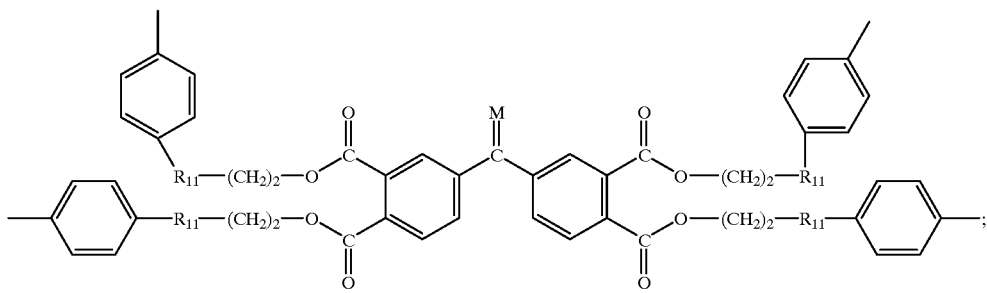

Ar₂ is 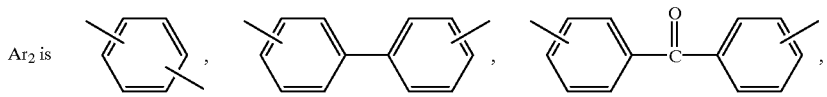

these groups are unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR₇, —SH, —SR₈, —SOR₈, —SO₂R₈, —CN, —SO₂NH₂, —SO₂NH($C_1$–$C_4$alkyl), —SO₂—N($C_1$–$C_4$alkyl)₂, —NR₉R₁₀, —NHCOR₉, or by a group of the formula V as defined above, or Ar₂ is a group of the formula VIa or VIIa

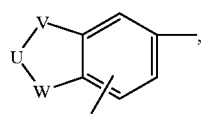 (VIa)

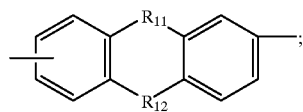 (VIIa)

X is a direct bond, —O—, —S— or —N(R₆)—;

Y is hydrogen, $C_1$–$C_{12}$alkyl, which is unsubstituted or substituted by 1 to 5 OH, OR₆, COOR₆, SH, N(R₆)₂ or halogen or substituted 1 to 5 times by a group of the formula Ia

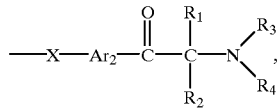 (Ia)

or Y is $C_2$–$C_{20}$alkyl, which is interrupted by 1 to 9 —O—, —N(R₆)—, —S—, —SS—, —X—C(=O)—, —X—C(=S)—, —C(=O)—X—, —X—C(=O)—X—, —C(=S)—X—,

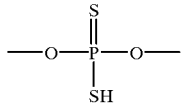

wherein the interrupted $C_2$–$C_{20}$alkyl can further be substituted by 1 to 5 SH, or Y is benzyl which is unsubstituted or substituted once or twice by —CH₂SH and said benzyl may further be substituted by 1 to 4 $C_1$–$C_4$alkyl, or Y is Ar (as defined above), or a group

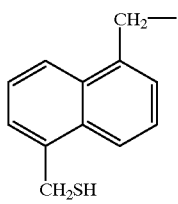

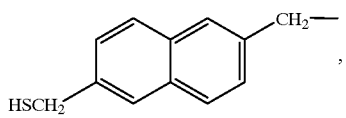

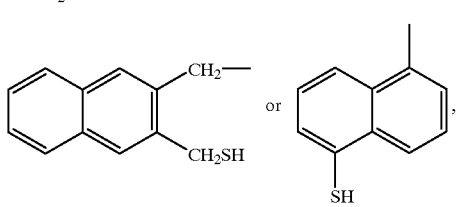

or Y is a heterocyclic 5–7 membered aliphatic or aromatic ring, comprising 1 to 4 N, O or/and S-atoms, or Y is a 8–12 membered bicyclic aliphatic or aromatic ring system, comprising 1 to 6 N, O or/and S-atoms, which mono- or bicyclic rings can further be substituted by SH or 1–5 times by a group of the formula Ia, or Y is a group

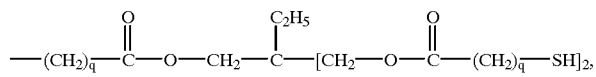

-continued

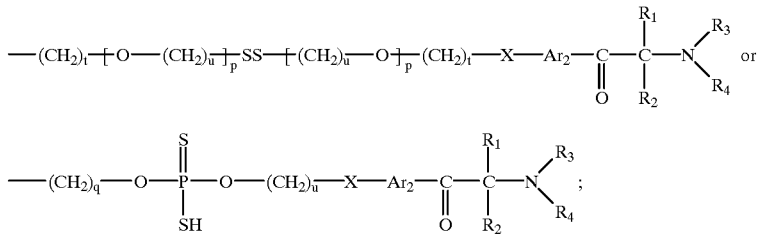

q is 1 or 2;
r is 1, 2 or 3;
p is 0 or 1;
t is 1 to 6;
u is 2 or 3;
$R_1$ and $R_2$ independently of one another are $C_1$–$C_8$alkyl, which is unsubstituted or substituted by OH, $C_1$–$C_4$alkoxy, SH, CN, —COO($C_1$–$C_8$alkyl), ($C_1$–$C_4$alkyl)-COO— or —N($R_3$)($R_4$), or $R_1$ and $R_2$ independently of one another are $C_3$–$C_6$alkenyl, phenyl, chlorophenyl, $R_7$—O-phenyl, $R_8$—S-phenyl or phenyl-$C_2$–$C_3$-alkyl, wherein said $C_3$–$C_6$alkenyl, phenyl, chlorophenyl, $R_7$—O-phenyl, $R_8$—S-phenyl or phenyl-$C_2$–$C_3$-alkyl are unsubstituted or substituted by 1 to 5 SH, or $R_1$ and $R_2$ together are unbranched or branched $C_2$–$C_9$alkylene, $C_3$–$C_9$oxaalkylene or $C_3$–$C_9$azaalkylene, wherein said $C_2$–$C_9$alkylene, $C_3$–$C_9$oxaalkylene or $C_3$–$C_9$azaalkylene are unsubstituted or substituted by 1 to 5 SH or $R_1$ and $R_2$ independently of one another are a radical of the formula IX or X

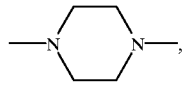

(IX)

(X)

$R_3$ is hydrogen, $C_1$–$C_{12}$alkyl, $C_2$–$C_4$alkyl, which is substituted by OH, SH, $C_1$–$C_4$alkoxy, CN or —COO ($C_1$–$C_4$alkyl), or $R_3$ is $C_3$–$C_5$alkenyl, $C_5$–$C_{12}$-cycloalkyl or phenyl-$C_1$–$C_3$alkyl;
$R_4$ is $C_1$–$C_{12}$alkyl, $C_2$–$C_4$alkyl, which is substituted by OH, SH, $C_1$–$C_4$alkoxy, CN or —COO($C_1$–$C_4$alkyl), or $R_4$ is $C_3$–$C_5$alkenyl, $C_5$–$C_{12}$-cycloalkyl, phenyl-$C_1$–$C_3$alkyl, unsubstituted phenyl or phenyl, which is substituted by halogen, $C_1$–$C_{12}$alkyl, $C_1$–$C_4$alkoxy or —COO($C_1$–$C_4$alkyl);
or $R_4$ together with $R_2$ is $C_1$–$C_7$alkylene, phenyl-$C_1$–$C_4$alkylene, o-xylylene, 2-butenylene or $C_2$–$C_3$oxaalkylene or $C_2$–$C_3$azaalkylene;
or $R_3$ and $R_4$ together are $C_3$–$C_7$alkylene, which can be interrupted by —O—, —S—, —CO— or —N($R_6$)— and which $C_3$–$C_7$alkylene can be substituted by OH, SH, $C_1$–$C_4$alkoxy or —COO ($C_1$–$C_4$alkyl);
$R_5$ is $C_1$–$C_6$alkylene, xylylene, cyclohexylene, wherein said $C_1$–$C_6$alkylene, xylylene, cyclohexylene are unsubstituted or substituted by 1 to 5 SH, or $R_5$ is a direct bond;

$R_6$ is hydrogen, unsubstituted or OH—, SH— or HS—($CH_2$)$_d$—COO-substituted $C_1$–$C_{12}$alkyl, $C_2$–$C_{12}$alkyl, which is interrupted by —O—, —NH— or —S—, or $R_6$ is $C_3$–$C_5$alkenyl, phenyl-$C_1$–$C_3$-alkyl, $CH_2CH_2CN$, unsubstituted or OH- or SH-substituted $C_1$–$C_4$alkyl-CO—$CH_2CH_2$—, unsubstituted or OH- or SH-substituted $C_2$–$C_8$alkanoyl or $R_6$ is benzoyl;
Z is a divalent radical of the formula

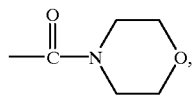

—N($R_{17}$)— or —N($R_{17}$)—$R_{18}$—N($R_{17}$)—;
U is unbranched or branched $C_1$–$C_7$alkylene;
V and W independently of one another are a direct bond, —O—, —S— or —N($R_6$)—, provided that V and W are not both a direct bond simultaneously;
M is O, S or N($R_6$);
$R_7$ is hydrogen, $C_1$–$C_{12}$alkyl, $C_3$–$C_{12}$-alkenyl, cyclohexyl, hydroxycyclohexyl, or $R_7$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO ($C_1$–$C_4$alkyl), —OOCR$_{19}$, —COOH, —COO ($C_1$–$C_8$alkyl), —CONH($C_1$–$C_4$alkyl), —CON ($C_1$–$C_4$alkyl)$_2$,

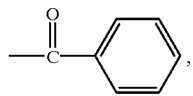

—CO($C_1$–$C_4$alkyl) or or $R_7$ is 2,3-epoxypropyl, —(CH$_2$CH$_2$O)$_m$H, unsubstituted phenyl, or phenyl which is substituted by halogen, $C_1$–$C_4$alkyl, $C_1$–$C_4$alkoxy or —COO($C_1$–$C_4$alkyl), or $R_7$ is phenyl-$C_1$–$C_3$alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si($R_{20}$)($R_{21}$)$_2$, or —SO$_2$R$_{22}$;
$R_8$ is $C_1$–$C_{12}$alkyl, $C_3$–$C_{12}$alkenyl, cyclohexyl, hydroxycyclohexyl, or $R_8$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO ($C_1$–$C_4$alkyl), —OOCR$_{19}$, —COOH, —COO $(C_1-C_8alkyl)$, $-CON(C_1-C_4alkyl)_2$,

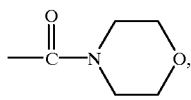

$-CO(C_1-C_4alkyl)$ or

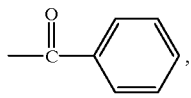

or $R_8$ is 2,3-epoxypropyl, phenyl-$C_1-C_3$alkyl, phenyl-$C_1-C_3$hydroxyalkyl, unsubstituted phenyl or phenyl which is mono- or poly-substituted by halogen, SH, $C_1-C_4$alkyl, $C_1-C_4$alkoxy or $-COO(C_1-C_4alkyl)$, or $R_8$ is 2-benzothiazyl, 2-benzimidazolyl, $-CH_2CH_2-O-CH_2CH_2-SH$ or $-CH_2CH_2-S-CH_2CH_2-SH$;

$R_9$ and $R_{10}$ independently of one another are hydrogen, $C_1-C_{12}$alkyl, $C_2-C_4$alkyl, which is substituted by OH, SH, $C_1-C_4$alkoxy, CN or $-COO(C_1-C_4alkyl)$, or $R_9$ and $R_{10}$ independently of one another are $C_3-C_5$alkenyl, cyclohexyl, phenyl-$C_1-C_3$alkyl, unsubstituted phenyl or phenyl which is mono- or poly-substituted by $C_1-C_{12}$alkyl or halogen, or $R_9$ and $R_{10}$ together are $C_2-C_7$alkylene which can be interrupted by $-O-$, $-S-$ or $-N(R_{18})-$;

$R_{11}$ and $R_{12}$ independently of one another are a direct bond, $-CH_2-$, $-CH_2CH_2-$, $-O-$, $-S-$, $-CO-$ or $-N(R_6)-$; provided that $R_{11}$ and $R_{12}$ are not a direct bond at the same time;

$R_{13}$ is hydrogen, $C_1-C_8$alkyl or phenyl wherein $C_1-C_8$alkyl or phenyl are unsubstituted or substituted by 1 to 5 SH;

$R_{14}$, $R_{15}$ and $R_{16}$ independently of one another are hydrogen or unsubstituted or SH-substituted $C_1-C_4$alkyl;

$R_{17}$ is hydrogen, unsubstituted or SH-substituted $C_1-C_8$alkyl or unsubstituted or SH-substituted phenyl;

$R_{18}$ is unbranched or branched $C_2-C_{16}$alkylene, which can be interrupted by 1 to 6 $-O-$, $-S-$ or $-N(R_{17})-$ or substituted by 1 to 5 groups SH;

$R_{19}$ is $C_1-C_4$alkyl, $C_2-C_4$alkenyl or phenyl;

$R_{20}$ and $R_{21}$ independently of one another are $C_1-C_4$alkyl or phenyl;

$R_{22}$ is $C_1-C_{18}$alkyl, phenyl or phenyl substituted by $C_1-C_{14}$alkyl;

$Ar_3$ is phenyl, naphthyl, furyl, thienyl or pyridiyl, wherein said radicals are unsubstituted or substituted by halogen, SH, OH, $C_1-C_{12}$alkyl, $C_1-C_4$alkyl, which is substituted by OH, halogen, SH, $-N(R_{17})_2$, $C_1-C_{12}$alkoxy, $-COO(C_1-C_{18}alkyl)$, $-CO(OCH_2CH_2)_nOCH_3$ or $-OCO(C_1-C_4alkyl)$, or said radicals are substituted by $C_1-C_{12}$alkoxy, $C_1-C_4$alkoxy, which is substituted by $-COO(C_1-C_{18}alkyl)$ or $-CO(OCH_2CH_2)_nOCH_3$, or said radicals are substituted by $-(OCH_2CH_2)_nOH$, $-(OCH_2CH_2)_nOCH_3$, $C_1-C_8$alkylthio, phenoxy, $-COO(C_1-C_{18}alkyl)$, $-CO(OCH_2CH_2)_nOCH_3$, phenyl or benzoyl;

n is 1 to 20;
m is 2 to 20;
provided that at least one of the radicals Ar, $Ar_1$, $Ar_2$, $Ar_3$, $R_1$, $R_2$, $R_3$, $R_4$, $R_5$ or Y is substituted by 1 to 5 SH groups, or provided that Y contains at least one $-SS-$ group; and provided that if $R_3$ and $R_4$ are morpholino and $R_1$ and $R_2$ simultaneously are methyl, $Ar_1$ is not phenyl substituted by $SR_8$, with $R_8$ being H or $-CH_2CH_2-O-CH_2CH_2SH$; and provided that if $R_3$ and $R_4$ are morpholino and $R_1$ and $R_2$ simultaneously are methyl, and $Ar_2$ is phenylene and X is S, Y is not hydrogen or $-CH_2CH_2-O-CH_2CH_2-SH$;

or an acid addition salt of a compound of the formula I, II, III or IV, are effective initiators for the photopolymerization of ethylenically unsaturated compounds.

$C_1-C_{20}$alkyl is linear or branched and is, for example, $C_1-C_{18}$-, $C_1-C_{14}$-, $C_1-C_{12}$-, $C_1-C_8$-, $C_1-C_6$- or $C_1-C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl. $C_1-C_{18}$alkyl, $C_1-C_{14}$alkyl, $C_1-C_{12}$alkyl, $C_1-C_8$alkyl, $C_1-C_6$alkyl and $C_1-C_4$alkyl have the same meanings as given above for $C_1-C_{20}$alkyl up to the corresponding number of C-atoms.

Mono- or polysubstituted $C_1-C_4$alkyl is substituted 1 to 6 times, for example 1 to 4 times, especially once or twice.

$C_2-C_4$hydroxyalkyl is linear or branched $C_2-C_4$alkyl which is substituted by OH. $C_2-C_4$alkyl has the same meanings as given above for $C_1-C_{20}$alkyl up to the corresponding number of C-atoms. Examples are hydroxymethyl, 2-hydroxyethyl, 1-hydroxyethyl, 3-hydroxypropyl, 2-hydroxypropyl, 4-hydroxybutyl.

$C_2-C_{10}$alkoxyalkyl is $C_2-C_{10}$alkyl, which is interrupted by one O-atom. $C_2-C_{10}$alkyl has the same meanings as given above for $C_1-C_{20}$alkyl up to the corresponding number of C-atoms. Examples are methoxymethyl, methoxyethyl, methoxypropyl, ethoxymethyl, ethoxyethyl, ethoxypropyl, porpoxymethyl, prpopxyethyl, propoxypropyl. $C_2-C_{20}$alkyl interrupted by 1 to 9, 1–5, 1–3 or 1 or 2 $-O-$, $-N(R_6)-$, $-S-$, $-SS-$, $-X-C(=O)-$, $-X-C(=S)-$, $-C(=O)-X-$, $-X-C(=O)-X-$, $-C(=S)-X-$,

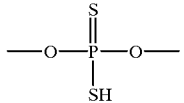

produces, for example, structural units such as $-CH_2-O-CH_2-$, $-CH_2-S-CH_2-$, $-CH_2-N(CH_3)-CH_2-$, $-CH_2CH_2-O-CH_2CH_2-$, $-[CH_2CH_2O]_y-$, $-[CH_2CH_2O]_y-CH_2-$, where y=1–5, $-(CH_2CH_2O)_5CH_2CH_2-$, $-CH_2-CH(CH_3)-O-CH_2-CH(CH_3)-$ or $-CH_2-CH(CH_3)-O-CH_2-CH_2CH_2-$. If $C_2-C_{20}$alkyl is interrupted by $-O-$, it is preferably interrupted by more than one $-O-$, for example 2 to 9, 2–5, 2–3 or 2 $-O-$.

$C_2-C_{16}$alkylene is linear or branched alkylene, for example $C_1-C_7$alkylene, $C_1-C_6$alkylene, $C_1-C_4$alkylene, namely methylene, ethylene, propylene, 1-methylethylene 1,1-dimethylethylene, 2,2-dimethylpropylene, butylene, 1-methylbutylene, 1-methylpropylene, 2-methylpropylene, pentylene, hexylene, heptylene, octylene, nonylene, decylene, dodecylene, tetradecylene or hexadecylene. $C_1-C_7$alkylene and $C_1-C_6$alkylene have the same meanings as given above for $C_2-C_{16}$alkylene up to the corresponding number of C-atoms and are linear or branched as well.

If $R_1$ and $R_2$ together are $C_2-C_9$alkylene, together with the C-atom to which they are bonded for example propyl, pentyl, hexyl, octyl or decyl rings are produced. If $R_1$ and $R_2$ together are $C_3-C_9$oxaalkylene or $C_3-C_9$azaalkylene, said rings are interrupted by O or N atoms. Thus, they are, for example piperidine, azolidine, oxolane or oxane rings.

If $R_3$ and $R_4$ together are $C_3-C_7$alkylene, optionally interrupted by $-O-$, $-S-$, $-CO-$ or $-N(R_6)-$, together with the N-atom to which they are bondend, for example morpholino or piperidino groups are formed. If $R_9$ and $R_{10}$ together are $C_2$–$C_7$alkylene, optionally interrupted by —O—, —S—, —CO— or —N($R_{18}$)—, together with the N-atom to which they are bondend, for example morpholino or piperidino groups are formed. If $R_{27}$ and $R_{28}$ together are $C_2$–$C_8$alkylene, optionally interrupted by —O—, —S— or —N($R_6$)—, together with the N-atom to which they are bondend, for example morpholino or piperidino groups are formed.

$C_3$–$C_{12}$alkenyl, for example $C_3$–$C_6$alkenyl or $C_3$–$C_5$alkenyl radicals may be mono or polyunsaturated and are for example allyl, methallyl, 1,1-dimethylallyl, 1-butenyl, 3-butenyl, 2-butenyl, 1,3-pentadienyl, 5-hexenyl or 7-octenyl, especially allyl. $C_3$–$C_6$alkenyl, $C_3$–$C_5$alkenyl and $C_2$–$C_4$alkenyl have the same meanings as given above for $C_3$–$C_{12}$alkenyl up to the corresponding number of C-atoms, $C_2$alkenyl is vinyl.

$C_2$–$C_8$alkanoyl is for example $C_2$–$C_6$-, $C_2$–$C_4$- or $C_2$–$C_3$alkanoyl. These radicals are linear or branched are are for example ethanoyl, propanoyl, 2-methylpropanoyl, hexanoyl or octanoyl. $C_2$–$C_3$alkanoyl has the same meanings as given for $C_2$–$C_8$alkanoyl up to the corresponding number of C-atoms.

$C_5$–$C_{12}$cycloalkyl is for example $C_5$–$C_8$- or $C_5$–$C_6$cycloalkyl, namely cyclopentyl, cyclohexyl, cyclooctyl, cyclododecyl, especially cyclopentyl and cyclohexyl, preferably cyclohexyl. $C_5$–$C_6$cycloalkyl is cyclopentyl or cyclohexyl.

$C_1$–$C_{12}$alkoxy, is for example $C_1$–$C_8$alkoxy, especially $C_1$–$C_4$alkoxy, and is a linear or branched radical, for example, methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, sec-butyloxy, iso-butyloxy or tert-butyloxy, preferably methoxy. $C_1$–$C_8$alkoxy and $C_1$–$C_4$alkoxy have the same meanings as given for $C_1$–$C_{12}$alkoxy up to the corresponding number of C-atoms.

$C_1$–$C_8$alkylthio, for example $C_1$–$C_6$- or $C_1$–$C_4$alkylthio is linear or branched and is, for example methylthio, ethylthio, n-propylthio, i-propylthio, n-butylthio, i-butylthio, s-butylthio, t-butylthio, pentylthio, hexylthio or octylthio, preferably methylthio or butylthio.

$C_3$–$C_5$alkenoxy radicals may be once or twice unsaturated and are for example allyloxy, methallyloxy, 1,1-dimethylallyloxy, 1-butenyloxy, 3-butenyloxy, 2-butenyloxy or 1,3-pentadienyloxy, especially allyloxy.

Phenyl-$C_1$–$C_3$-alkyl is for example benzyl, phenylethyl, α-methylbenzyl or α,α-dimethylbenzyl, especially benzyl. Substituted phenyl-$C_1$–$C_3$alkyl is substituted one to four times, for example once, twice or three times, especially twice or three times, on the phenyl ring.

A heterocyclic 5–7 membered aliphatic or aromatic ring, comprising 1 to 4 N, O or/and S-atoms is for example furyl, thienyl, pyrrolyl, pyridyl, pyrazinyl, pyranyl, benzoxazolyl, dioxolanyl, dioxanyl, thiazolyl, oxazolyl, 1,3,4-thiadiazolyl, azolyl or diazolyl.

A 8–12 membered bicyclic aliphatic or aromatic ring system, comprising 1 to 6 N, O or/and S-atoms is for example benzofuranyl, isobenzofuranyl, indolyl, indazolyl, purinyl, quinolinyl, quinoxalinyl, purinyl or isoquinolinyl.

Chlorophenyl is phenyl substituted by chlorine.

Substituted phenyl is substituted one to four times, for example once, twice or three times, especially once or twice. Substituents are, for example in position 2, 3, 4, 5 or 6, especially in position 2, 6 or 3 of the phenyl ring. Mono- or polysubstituted phenyl is substituted one to four times, for example once, twice or three times, especially once or twice.

Halogen is fluorine, chlorine, bromine and iodine, especially fluorine, chlorine and bromine, preferably bromine and chlorine.

Examples for Ar being a group of the formula VI are

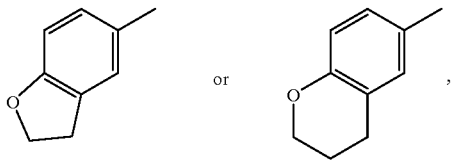

wherein V is O, U is $C_2$- or $C_3$alkylene and W is a direct bond.

The term "acid addition salts of the formulae 1–IV" covers α-aminoketone compounds of the formulae 1–IV which are reacted with a carboxylic acid derivative or organic sulfonic acid derivative. That means the compounds are protonated at a nitrogen atom and the counter ion is the respective anion of the acid derivative. Examples for suitable acid derivatives are trifluoromethyl carboxylic acid,

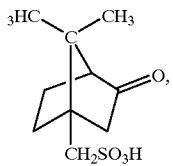

toluenesulfonic acid, preferably toluene sulfonic acid.

If $Ar_2$ is phenylene, X is S and Y is $C_2$–$C_{20}$alkyl interrupted by 1 to 9 O-atoms, the alkylene is preferably interrupted by more than one O-atoms, for example, 2–9, 2–8, 3–5, or 4, especially 2 O-atoms.

$R_8$ preferably is $C_1$–$C_{12}$alkyl, $C_3$–$C_{12}$alkenyl, cyclohexyl, hydroxycyclohexyl, or $R_8$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —OOCR$_{19}$, —COOH, —COO($C_1$–$C_8$alkyl), —CON($C_1$–$C_4$alkyl)$_2$,

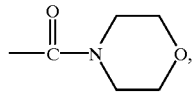

—CO($C_1$–$C_4$alkyl) or

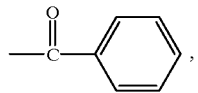

or $R_8$ is 2,3-epoxypropyl, phenyl-$C_1$–$C_3$alkyl, phenyl-$C_1$–$C_3$hydroxyalkyl, unsubstituted phenyl or phenyl which is mono- or poly-substituted by halogen, SH, $C_1$–$C_4$alkyl, $C_1$–$C_4$alkoxy or —COO($C_1$–$C_4$alkyl), or $R_8$ is 2-benzothiazyl, 2-benzimidazolyl, or —CH$_2$CH$_2$—S—CH$_2$CH$_2$—SH.

Y preferably is $C_1$–$C_{20}$alkyl, which is substituted by SH. Further preferred is Y as $C_2$–$C_{20}$alkyl interrupted by 1 to 9 —S—, —O—, —N($R_6$)—, —SS—, —X—C(═O)—, —C(═O)—X—, preferably —S—, wherein the alkyl group is linear or branched as indicated above and optionally substituted by 1 to 5 SH.

The thiol compounds of the formulae I can, for example, be prepared from halophenyl aliphatic ketones by treatment with an excess of the corresponding dithiol or polythiol.

Thiol compounds of the formulae I, II, III and IV can also be obtained from the corresponding vinyl, hydroxy, halogen or amino precursors by known methods. See, for example "The Chemistry of the Thiol Group", ed. S. Patai, John Wiley & Sons, p. 163, New York, 1974. The vinyl group can be transformed to the thiol group directly by hydrogen sulfide addition or by thioacetic acid addition and successive hydrolysis.

Halogen groups can be directly converted to thiols by reaction with metal hydrogen sulfides. Other routes to thiol groups include the transformation of Bunte salts, xanthates, isothiuronium salts, phosphorthiorate and thioesters. Further, hydroxy groups can be transformed to thiol groups directly by the reaction with hydrogen sulfide or phosphorous pentasulfides, or via the corresponding halogens using one of the methods described above. The esterification of alcohols with a mercaptocarboxylic acid, such as mercaptoacetic acid or mercaptopropionic acid provides another convenient access to thiols. Amines can, for example, be converted to thiols by amidation with a mercaptocarboxylic acid, such as mercaptoacetic acid or mercaptopropionic acid.

Dissulfides of the formula I according to the invention can also be obtained by known procedures, see, for example, "Organic Functional Group Preparations", S. R. Sandler, Academic Press, p. 586, New York, 1983. For instance, the desired disulfide compounds are prepared by the reaction of corresponding halides with sodium disulfide. Oxidation of the thiols is also a convenient method to prepare disulfides. For example, hydrogen peroxide, iodine in ethanol and alkaline solution of iodine can be used as oxidants. Unsymmetrical disulfides can be prepared by the reaction of sodium thiolates with an alkylthiosulfate, such as n-butylthiosulfate, or with an aryl thiosulfate.

The performance of such reactions and the reaction conditions for such reactions are generally known to the art-skilled. The reaction is preferably carried out in a polar solvent, for example dimethylformamide, dimethylacetamide, N-methylpyrolidine or dimethylsulfoxide. The reaction also can be carried out in a mixed solvent system, for instance, of one of the above mentioned polar solvents and an inert aprotic solvent, such as for example benzene, toluene, chloroform or methylenechloride. A large excess of dithiol is advisable for the reaction to minimise the formation of the dimeric form. The amount of dithiol used for the reaction is, for example, from 1 to 10 equivalents to the substrate, preferably from 2 to 6 equivalents. The reaction can, for example, be carried out at room temperature (about 20° C.) up to 150° C., preferably from to 100° C. The reaction can be progressed with or without stirring, however, the reaction with stirring is preferable to accelerate the progress of the reaction.

Methods for the preparation of aliphatic aromatic α-aminoketone compounds, which can be transformed into the SH-substituted or —SS-containing compounds according to the invention by the above indicated methods, are for example disclosed in U.S. Pat. No. 4,315,807 column 9, line 42—column 11, line 23 and column 13, line 53—column 16, line 54. The preparation of α-aminoketone precursors for the addition of a thiol group, wherein $R_1$ or $R_2$ are alkenyl, especially allyl, or benzyl by C-allylation or C-benzylation is, for example disclosed in U.S. Pat. No. 5,077,402, column 16, line 17—column 18, line 31. Further descriptions of the preparation of aliphatic aromatic α-aminoketone compounds are given in U.S. Pat. Nos. 4,582,862, 4,992,547 and 5,077,402.

Preferred are compounds of the formula II, wherein a is 1.

Of interest are compounds wherein $Ar_2$ is a group

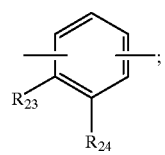

$R_{23}$ and $R_{24}$ independently of one another are hydrogen, halogen, $C_1$–$C_{12}$alkyl, cyclopentyl, cyclohexyl, phenyl, benzyl, benzoyl, $OR_{25}$, SH, $SR_{26}$, $SOR_{26}$, $SO_2R_{26}$, $NR_{27}R_{28}$, $NHSO_2R_{29}$;

$R_{25}$ is hydrogen, $C_1$–$C_{12}$alkyl, $C_1$–$C_6$alkyl substituted by —CN, —OH or —SH, or $R_{25}$ is $C_1$–$C_4$alkoxy, $C_3$–$C_5$alkenoxy, $OCH_2CH_2CN$, $OCH_2$—$CH_2COOR_{30}$, COOH or $COOR_{30}$, —$(CH_2$—$CH_2O)_sH$, $C_2$–$C_8$alkanoyl, $C_3$–$C_{12}$alkenyl, cyclohexyl, hydroxycyclohexyl, phenyl, phenyl substituted by halogen, $C_1$–$C_{12}$alkyl or $C_1$–$C_4$alkoxy, or $R_{25}$ is phenyl-$C_1$–$C_3$-alkyl, or —$Si(C_1$–$C_8$-alkyl)$_r$(phenyl)$_{3-r}$;

s is 2–20;

r is 1,2 or 3;

$R_{26}$ is $C_1$–$C_{12}$alkyl, $C_1$–$C_6$alkyl substituted by —OH, —SH, —CN, —$COOR_{30}$, $C_1$–$C_4$alkoxy, —$OCH_2CH_2CN$ or —$OCH_2$—$CH_2COOR_{30}$, or $R_{26}$ is $C_3$–$C_{12}$alkenyl, cyclohexyl, phenyl-$C_1$–$C_3$-alkyl, phenyl, phenyl substituted by halogen, $C_1$–$C_{12}$alkyl or $C_1$–$C_4$alkoxy;

$R_{27}$ and $R_{28}$ independently of one another are hydrogen, unsubstituted or SH-substituted $C_1$–$C_{12}$alkyl, $C_2$–$C_4$hydroxyalkyl, $C_2$–$C_{10}$alkoxyalkyl, $C_3$–$C_5$alkenyl, $C_5$–$C_{12}$cycloalkyl, phenyl-$C_1$–$C_3$-alkyl, phenyl, phenyl substituted by halogen, OH, SH, $C_1$–$C_{12}$alkyl or $C_1$–$C_4$alkoxy, or $R_{27}$ and $R_{28}$ are $C_2$–$C_3$alkanoyl or benzoyl; or $R_{27}$ and $R_{28}$ together are $C_2$–$C_8$alkylene which can be interrupted by —O—, —S— or —$NR_6$, or together are $C_2$–$C_8$alkylene which can be substituted by —OH, $C_1$–$C_4$alkoxy or $COOR_{30}$;

$R_6$ is hydrogen, unsubstituted or OH—, SH— or HS—$(CH_2)_q$—COO-substituted $C_1$–$C_{12}$alkyl, $C_2$–$C_{12}$alkyl, which is interrupted by —O—, —NH— or —S—, or $R_6$ is $C_3$–$C_5$alkenyl, phenyl-$C_1$–$C_3$-alkyl, $CH_2CH_2CN$, unsubstituted or OH- or SH-substituted $C_1$–$C_4$alkyl-CO—$CH_2CH_2$—, unsubstituted or OH- or SH-substituted $C_2$–$C_8$alkanoyl or $R_6$ is benzoyl;

q is 1 or 2;

$R_{29}$ is $C_1$–$C_{18}$alkyl, unsubstituted phenyl or naphthyl, phenyl or naphthyl substituted by halogen, $C_1$–$C_{12}$alkyl or $C_1$–$C_8$alkoxy,; and $R_{30}$ is unsubstituted $C_1$–$C_4$alkyl or $C_1$–$C_4$alkyl, which is substituted by OH or SH.

Other preferred compounds are those, wherein $Ar_2$ is

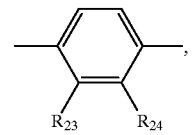

X is S and Y is Ar substituted by $SR_8$ or $OR_7$.

Preferred are further compounds wherein Y is SH-substituted $C_1$–$C_{12}$alkyl, $C_2$–$C_{20}$alkyl, which is interrupted by —S— or —SS—, or Y is a SH-substituted phenyl-, biphenyl- or benzoylphenyl-group, or a group

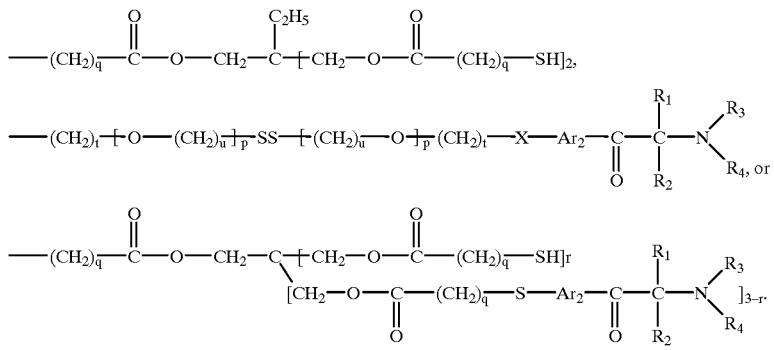

Of special interest are compounds of the formula I or II, wherein a is 1; $Ar_1$ is a phenyl or biphenyl group, which phenyl or biphenyl group is substituted by 1 to 5 of the radicals —$OR_7$, —SH, —$SR_8$, —$NR_9R_{10}$; $Ar_2$ is

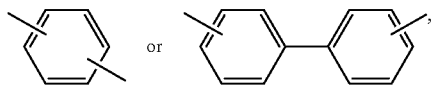

these groups are unsubstituted or substituted by 1 to 5 of the radicals —$OR_7$, —SH, —$SR_8$, —$NR_9R_{10}$; X is —O—, —S— or —$N(R_6)$—; Y is hydrogen, $C_1$–$C_{12}$alkyl, which is unsubstituted or substituted by 1 to 5 OH, SH, or Y is $C_2$–$C_{20}$alkyl, which is interrupted by 1 to 9 —O—, —S—, —X—C(=O)—, —C(=O)—X—, wherein the interrupted $C_2$–$C_{20}$alkyl can further be substituted by 1 to 5 SH, or Y is benzyl which is substituted once or twice by —$CH_2SH$ and said benzyl may further be substituted by 1 to 4 $C_1$–$C_4$alkyl; $R_1$ and $R_2$ independently of one another are $C_1$–$C_8$alkyl or phenyl, or $R_1$ and $R_2$ independently of one another are a radical of the formula IX or X

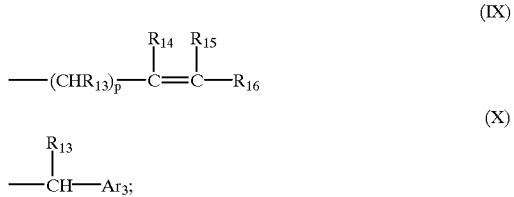

$R_3$ and $R_4$ are $C_1$–$C_{12}$alkyl, or $R_3$ and $R_4$ together are $C_3$–$C_7$alkylene, which can be interrupted by —O—, and which $C_3$–$C_7$alkylene can be substituted by SH; $R_7$ is $C_1$–$C_{12}$alkyl; $R_8$ is $C_1$–$C_{12}$alkyl, or $R_8$ is $C_1$–$C_4$alkyl, which is mono- or polysubstituted with SH, or $R_8$ is, —$CH_2CH_2$—O—$CH_2CH_2$—SH or —$CH_2CH_2$—S—$CH_2CH_2$—SH; $R_9$ and $R_{10}$ independently of one another are hydrogen or $C_2$–$C_4$alkyl, which is substituted by SH; and $R_{13}$, $R_{14}$, $R_{15}$ and $R_{16}$ are hydrogen.

Other interesting compounds are such, wherein $R_1$ and $R_2$ independently of one another are $C_1$–$C_4$alkyl, benzyl or $C_3$–$C_6$alkenyl; $R_3$ and $R_4$ independently of one another are $C_1$–$C_4$alkyl or $R_3$ and $R_4$ together are $C_3$–$C_7$alkylene, which is interrupted by —O—; $Ar_1$ is phenyl substituted by $SR_8$; $R_8$ is SH-substituted $C_1$–$C_4$alkyl or SH-substituted phenyl; $Ar_2$ is phenylen; X is S or NH; and Y is $C_1$–$C_{10}$alkyl substituted by SH and/or 1 to 2 OH.

In accordance with the invention, the compounds of the formula I, II, III and IV can be used as photoinitiators for the photopolymerization of ethylenically unsaturated compounds or of mixtures which comprise such compounds. This use may also be practised in combination with another photoinitiator and/or with other additives.

The invention therefore also relates to photopolymerizable compositions comprising (a) at least one ethylenically unsaturated photopolymerizable compound, and (b) as photoinitiator, at least one compound of the formula I, II, III or IV.

In this context, the composition may contain other additives in addition to component (b), and component (b) may be a mixture of photoinitiators of the formulae I, II, III or IV.

The ethylenically unsaturated compounds to be polymerized may be non-volatile monomeric, oligomeric or polymeric compounds. The unsaturated compounds may contain one or more olefinic double bonds. They may be of low molecular weight (monomeric) or of relatively high molecular weight (oligomeric). Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth) acrylamides, vinyl esters such as vinyl acetate, vinyl ethers such as isobutyl vinyl ether, styrene, alkylstyrenes and halostyrenes, N-vinylpyrrolidone, vinyl chloride or vinylidene chloride.

Examples of monomers containing two or more double bonds are the diacrylates of ethylene glycol, propylene glycol, neopentylglycol, hexamethylene glycol or bisphenol A, and also 4,4'-bis(2-acryloyloxyethoxy)diphenylpropane, trimethylolpropane triacrylate, pentaerythritol triacrylate or pentaerythritol tetraacrylate, vinyl acrylate, divinylbenzene, divinyl succinate, diallyl phthalate, triallyl phosphate, triallyl isocyanurate or tris(2-acryloylethyl)isocyanurate.

Examples of relatively high molecular weight (oligomeric) polyunsaturated compounds are acrylicized epoxy resins, and polyesters, polyurethanes and polyethers which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and vinyl ether oligomers, and also maleate-terminated oligomers having polyester, polyurethane, polyether, polyvinyl ether and epoxy main chains. Combinations of vinyl ether group-containing oligomers and polymers as are described in WO 90/01512 are particularly highly suitable. However, copolymers of vinyl ether and maleic acid-functionalized monomers are also appropriate. Such unsaturated oligomers can also be referred to as prepolymers.

Examples of particularly suitable compounds are esters of ethylenically unsaturated carboxylic acids and polyols or polyepoxides, and polymers containing ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic acid and methacrylic acid are preferred.

Suitable polyols are aromatic and, in particular, aliphatic and cycloaliphatic polyols. Examples of aromatic polyols are hydroquinone, 4,4'-dihydroxybiphenyl, 2,2-di(4-hydroxyphenyl)propane, and also novolaks and resols. Examples of polyepoxides are those based on said polyols, especially aromatic polyols and epichlorohydrin. Other suitable polyols include polymers and copolymers which contain hydroxyl groups in the polymer chain or in side groups, for example polyvinyl alcohol and copolymers thereof or hydroxyalkyl polymethacrylates or copolymers thereof. Other suitable polyols are oligoesters containing hydroxyl end groups.

Examples of aliphatic and cycloaliphatic polyols are alkylenediols, preferably having 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycol having molecular weights of preferably from 200 to 1500, 1,3-cyclopentanediol, 1,2-, 1,3- or 1,4-cyclohexanediol, 1,4-dihydroxymethylcyclohexane, glycerol, tris-(β-hydroxyethyl)amine, trimethylolethane, trimethylolpropane, pentaerythritol, dipentaerythritol and sorbitol.

The polyols may be partially or fully esterified by means of one or more unsaturated carboxylic acids, where the free hydroxyl groups in partial esters may be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritoldimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitolhexaacrylate, oligoester acrylates and methacrylates, glycerol di- and triacrylate, 1,4-cyclohexane diacrylate, bisacrylates and bismethacrylates of polyethylene glycol having molecular weights of from 200 to 1500, or mixtures thereof.

Further suitable components (a) are the amides of identical or different unsaturated carboxylic acids of aromatic, cycloaliphatic and aliphatic polyamines, preferably having 2 to 6, in particular 2 to 4, amino groups. Examples of polyamines of this type are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy) or di(β-aminopropoxy)ethane. Other suitable polyamines are polymers and copolymers which may contain additional amino groups in the side chain, and oligoamides containing amino end groups. Examples of unsaturated amides of this type are: methylenebisacrylamide, 1,6-hexamethylenebisacrylamide, diethylenetriaminetrismethacrylamide, bis(methacrylamidopropoxy)ethane, β-methacrylamidoethyl methacrylate, and N-[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides may also be derived from dicarboxylic acids and ethylenically unsaturated diols or diamines, in particular from relatively long chain compounds containing, for example, 6 to 20 carbon atoms. Examples of polyurethanes are those built up from saturated or unsaturated diisocyanates and from unsaturated or saturated diols.

Other suitable components (a) are aminomodified polyetheracrylates, obtained by partially reacting the respective acrylates with amines.

Polybutadiene and polyisoprene and copolymers thereof are known. Examples of suitable comonomers are olefins such as ethylene, propene, butene, hexene, (meth)acrylate, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of vinyl alcohol or hydroxyalkyl derivatives thereof which have been esterified using (meth)acrylic acid, or homopolymers and copolymers of (meth)acrylates which have been esterified using hydroxyalkyl(meth)acrylates.

The photopolymerizable compounds may be employed alone or in any desired mixtures. Preference is given to mixtures of polyol(meth)acrylates.

The invention particularly relates to a photopolymerizable composition comprising as component (a) a polymer or oligomer having at least two ethylenically unsaturated groups and at least one carboxyl function within the molecule structure and (b) as photoinitiator, at least one compound of the formula I, II, III or IV

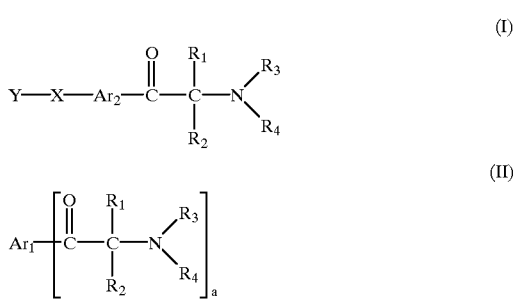

-continued

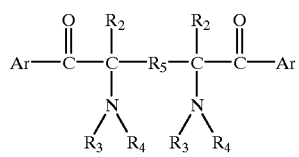 (III)

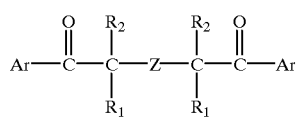 (IV)

wherein
a is an integer 1, 2 or 4;

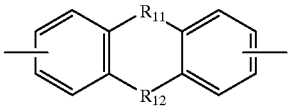 (VIII)

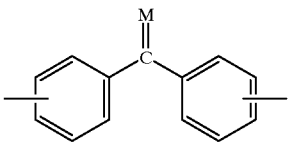 (VIIIa)

if a is 4, $Ar_1$ is a tetravalent aromatic radical of the formula VIIIb

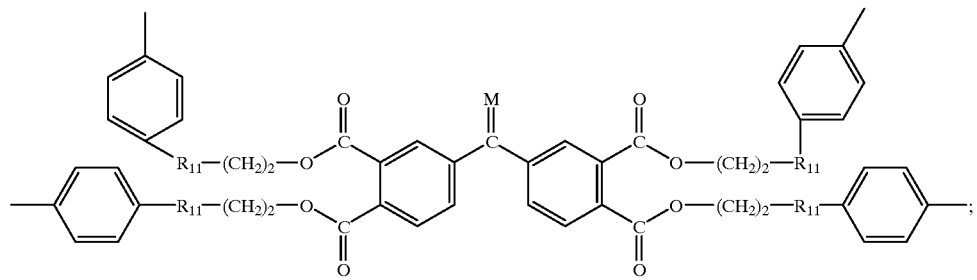 (VIIIb)

Ar is a phenyl, biphenyl or benzoylphenyl group, which is unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SH, —SR$_8$, —SOR$_8$, —SO$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of the formula V,

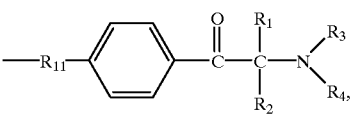 (V)

or Ar is a group of the formula VI or VII

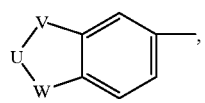 (VI)

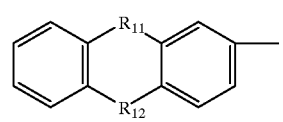 (VII)

$Ar_1$ if a is 1 has the same meanings as Ar;
if a is 2, $Ar_1$ is a divalent aromatic radical of the formula VIII or VIIIa $Ar_2$ is

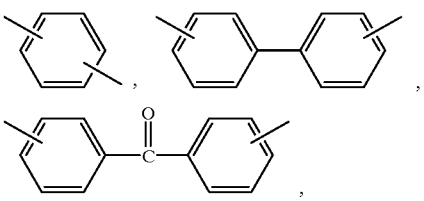

these groups are unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO ($C_1$–$C_4$alkyl), —OR$_7$, —SH, —SR$_8$, —SOR$_8$, —SO$_2$R$_8$, —CN, —SO$_2$NH$_2$, —SO$_2$NH($C_1$–$C_4$alkyl), —SO$_2$—N ($C_1$–$C_4$alkyl)$_2$, —NR$_9$R$_{10}$, —NHCOR$_9$, or by a group of the formula V as defined above, or $Ar_2$ is a group of the formula VIa or VIIa (VIa)

(VIIa)

X is a direct bond, —O—, —S— or —N(R$_6$)—;
Y is hydrogen, $C_1$–$C_{12}$alkyl, which is unsubstituted or substituted by 1 to 5 OH, OR$_6$, COOR$_6$, SH, N(R$_6$)$_2$ or halogen or substituted 1 to 5 times by a group of the formula Ia

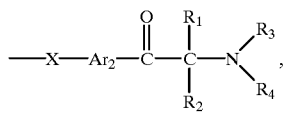
(Ia)

or Y is $C_2$–$C_{20}$alkyl, which is interrupted by 1 to 9 —O—, —N($R_6$)—, —S—, —SS—, —X—C(=O)—, —X—C(=S)—, —C(=O)—X—, —X—C(=O)—X—, —C(=S)—X—,

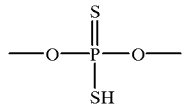

wherein the interrupted $C_2$–$C_{20}$alkyl can further be substituted by 1 to 5 SH, or Y is benzyl which is unsubstituted or substituted once or twice by —$CH_2SH$ and said benzyl may further be substituted by $C_1$–$C_4$alkyl, or Y is Ar (as defined above), or a group

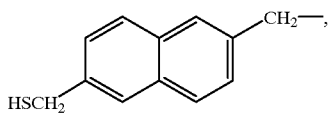

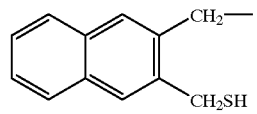
or

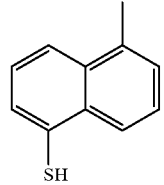

or Y is a heterocyclic 5–7 membered aliphatic or aromatic ring, comprising 1 to 4 N, O or/and S-atoms, or Y is a 8–12 membered bicyclic aliphatic or aromatic ring system, comprising 1 to 6 N, O or/and S-atoms, which mono- or bicyclic rings can further be substituted by SH or 1–5 times by a group of the formula Ia, or Y is a group

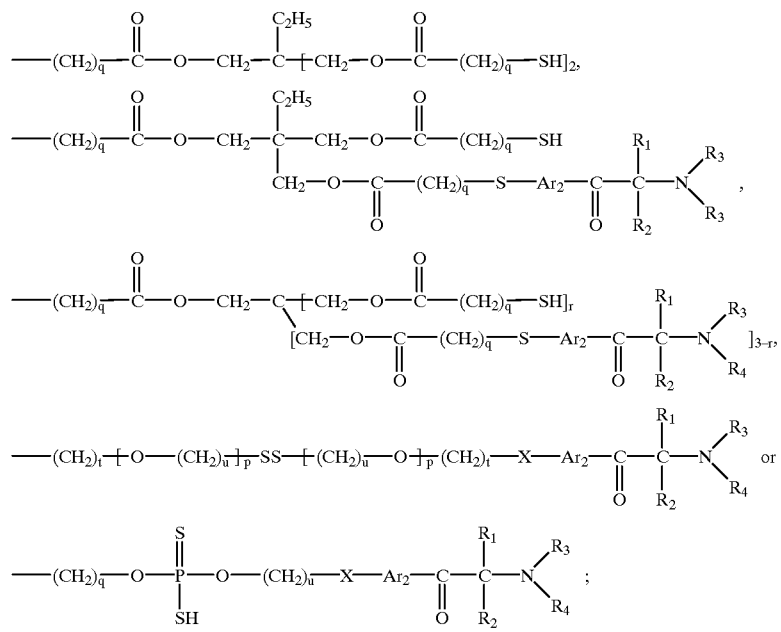

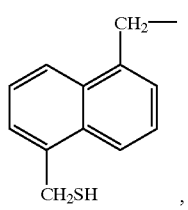

q is 1 or 2;
r is 1, 2 or 3;
p is 0 or 1;
t is 1 to 6;
u is 2 or 3;
$R_1$ and $R_2$ independently of one another are $C_1$–$C_8$alkyl, which is unsubstituted or substituted by OH, $C_1$–$C_4$alkoxy, SH, CN, —COO($C_1$–$C_8$alkyl), ($C_1$–$C_4$alkyl)-COO— or —N($R_3$)($R_4$), or $R_1$ and $R_2$ independently of one another are $C_3$–$C_6$alkenyl, phenyl, chlorophenyl, $R_7$—O-phenyl, $R_8$—S-phenyl or phenyl-$C_1$-$C_3$-alkyl, wherein said $C_3$-$C_6$alkenyl, phenyl, chlorophenyl, $R_7$—O-phenyl, $R_8$—S-phenyl or phenyl-$C_2$-$C_3$-alkyl are unsubstituted or substituted by 1 to 5 SH, or $R_1$ and $R_2$ together are unbranched or branched $C_2$-$C_9$alkylene, $C_3$-$C_9$oxaalkylene or $C_3$-$C_9$azaalkylene, wherein said $C_2$-$C_9$alkylene, $C_3$-$C_9$oxaalkylene or $C_3$-$C_9$azaalkylene are unsubstituted or substituted by 1 to 5 SH or $R_1$ and $R_2$ independently of one another are a radical of the formula IX or X

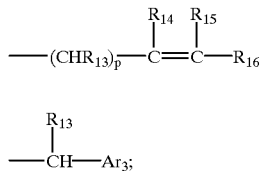

(IX)

(X)

$R_3$ is hydrogen, $C_1$-$C_{12}$alkyl, $C_2$-$C_4$alkyl, which is substituted by OH, SH, $C_1$-$C_4$alkoxy, CN or —COO($C_1$-$C_4$alkyl), or $R_3$ is $C_3$-$C_5$alkenyl, $C_5$-$C_{12}$-cycloalkyl or phenyl-$C_1$-$C_3$alkyl;

$R_4$ is $C_1$-$C_{12}$alkyl, $C_2$-$C_4$alkyl, which is substituted by OH, SH, $C_1$-$C_4$alkoxy, CN or —COO($C_1$-$C_4$alkyl), or $R_4$ is $C_3$-$C_5$alkenyl, $C_5$-$C_{12}$-cycloalkyl, phenyl-$C_1$-$C_3$alkyl, unsubstituted phenyl or phenyl, which is substituted by halogen, $C_1$-$C_{12}$alkyl, $C_1$-$C_4$alkoxy or —COO($C_1$-$C_4$alkyl);

or $R_4$ together with $R_2$ is $C_1$-$C_7$alkylene, phenyl-$C_1$-$C_4$alkylene, o-xylylene, 2-butenylene or $C_2$-$C_3$oxaalkylene or $C_2$-$C_3$azaalkylene;

or $R_3$ and $R_4$ together are $C_3$-$C_7$alkylene, which can be interrupted by —O—, —S—, —CO— or —N($R_6$)— and which $C_3$-$C_7$alkylene can be substituted by OH, $C_1$-$C_4$alkoxy or —COO($C_1$-$C_4$alkyl);

$R_5$ is $C_1$-$C_6$alkylene, xylylene, cyclohexylene, wherein said $C_1$-$C_6$alkylene, xylylene, cyclohexylene are unsubstituted or substituted by 1 to 5 SH, or $R_5$ is a direct bond;

$R_6$ is hydrogen, unsubstituted or OH—, SH— or HS—$(CH_2)_q$—COO-substituted $C_1$-$C_{12}$alkyl, $C_2$-$C_{12}$alkyl, which is interrupted by —O—, —NH— or —S—, or $R_6$ is $C_3$-$C_5$alkenyl, phenyl-$C_1$-$C_3$-alkyl, $CH_2CH_2CN$, unsubstituted or OH- or SH-substituted $C_1$-$C_4$alkyl-CO—$CH_2CH_2$—, unsubstituted or OH- or SH-substituted $C_2$-$C_8$alkanoyl or $R_6$ is benzoyl;

Z is a divalent radical of the formula

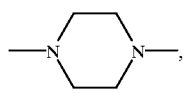

—N($R_{17}$)— or —N($R_{17}$)—$R_{18}$—N($R_{17}$)—;

U is unbranched or branched $C_1$-$C_7$alkylene;

V and W independently of one another are a direct bond, —O—, —S— or —N($R_6$)—, provided that V and W are not both a direct bond simultaneously;

M is O, S or N($R_6$);

$R_7$ is hydrogen, $C_1$-$C_{12}$alkyl, $C_3$-$C_{12}$-alkenyl, cyclohexyl, hydroxycyclohexyl, or $R_7$ is $C_1$-$C_4$alkyl, which is mono- or polysubstituted with Cl, Br, CN, SH, —N($C_1$-$C_4$alkyl)$_2$, piperidino, morpholino, OH, $C_1$-$C_4$alkoxy, —OCH$_2$CH$_2$CN, —OCH$_2$CH$_2$COO($C_1$-$C_4$alkyl), —OOCR$_{19}$, —COOH, —COO($C_1$-$C_8$alkyl), —CONH($C_1$-$C_4$alkyl), —CON($C_1$-$C_4$alkyl)$_2$,

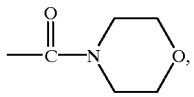

—CO($C_1$-$C_4$alkyl) or

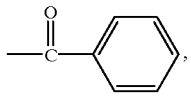

or $R_7$ is 2,3-epoxypropyl, —(CH$_2$CH$_2$O)$_m$H, unsubstituted phenyl, or phenyl which is substituted by halogen, $C_1$-$C_4$alkyl, $C_1$-$C_4$alkoxy or —COO($C_1$-$C_4$alkyl), or $R_7$ is phenyl-$C_1$-$C_3$alkyl, tetrahydropyranyl, tetrahydrofuranyl, —COOR$_{19}$, —COO($C_1$-$C_8$alkyl), —CONH($C_1$-$C_4$alkyl), —CON($C_1$-$C_8$alkyl)$_2$, —Si($R_{20}$)($R_{21}$)$_2$, or —SO$_2$R$_{22}$;

$R_8$ is $C_1$-$C_{12}$alkyl, $C_3$-$C_{12}$alkenyl, cyclohexyl, hydroxycyclohexyl, or $R_8$ is $C_1$-$C_4$alkyl, which is mono- or polysubstituted with Cl, Br, CN, SH, —N($C_1$-$C_4$alkyl)$_2$, piperidino, morpholino, OH, $C_1$-$C_4$alkoxy, —OCH$_2$CH$_2$CN, —OCH$_2$CH$_2$COO($C_1$-$C_4$alkyl), —OOCR$_{19}$, —COOH, —COO($C_1$-$C_8$alkyl), —CON($C_1$-$C_4$alkyl)$_2$,

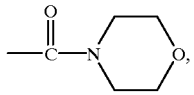

—CO($C_1$-$C_4$alkyl) or

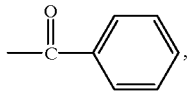

or $R_8$ is 2,3-epoxypropyl, phenyl-$C_1$-$C_3$alkyl, phenyl-$C_1$-$C_3$hydroxyalkyl, unsubstituted phenyl or phenyl which is mono- or poly-substituted by halogen, SH, $C_1$-$C_4$alkyl, $C_1$-$C_4$alkoxy or —COO($C_1$-$C_4$alkyl), or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

$R_9$ and $R_{10}$ independently of one another are hydrogen, $C_1$-$C_{12}$alkyl, $C_2$-$C_4$alkyl, which is substituted by OH, SH, $C_1$-$C_4$alkoxy, CN or —COO($C_1$-$C_4$alkyl), or $R_9$ and $R_{10}$ independently of one another are $C_3$-$C_5$alkenyl, cyclohexyl, phenyl-$C_1$-$C_3$alkyl, unsubstituted phenyl or phenyl which is mono- or poly-substituted by $C_1$-$C_{12}$alkyl or halogen, or $R_9$ and $R_{10}$ together are $C_2$-$C_7$alkylene which can be interrupted by —O—, —S— or —N($R_{18}$)—;

$R_{11}$ and $R_{12}$ independently of one another are a direct bond, —CH$_2$—, —CH$_2$CH$_2$—, —O—, —S—, —CO— or —N($R_6$)—; provided that $R_{11}$ and $R_{12}$ are not a direct bond at the same time;

$R_{13}$ is hydrogen, $C_1$-$C_8$alkyl or phenyl wherein $C_1$-$C_8$alkyl or phenyl are unsubstituted or substituted by 1 to 5 SH;

$R_{14}$, $R_{15}$ and $R_{16}$ independently of one another are hydrogen or unsubstituted or SH-substituted $C_1$–$C_4$alkyl;

$R_{17}$ is hydrogen, unsubstituted or SH-substituted $C_1$–$C_8$alkyl or unsubstituted or SH-substituted phenyl;

$R_{18}$ is unbranched or branched $C_2$–$C_{16}$alkylene, which can be interrupted by 1 to 6 —O—, —S— or —N($R_{17}$)— or substituted by 1 to 5 groups SH;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl, phenyl or phenyl substituted by $C_1$–$C_{14}$alkyl;

$Ar_3$ is phenyl, naphthyl, furyl, thienyl or pyridiyl, wherein said radicals are unsubstituted or substituted by halogen, SH, OH, $C_1$–$C_{12}$alkyl, $C_1$–$C_4$alkyl, which is substituted by OH, halogen, SH, —N($R_{17}$)$_2$, $C_1$–$C_{12}$alkoxy, —COO($C_1$–$C_{18}$alkyl), —CO(OCH$_2$CH$_2$)$_n$OCH$_3$ or —OCO($C_1$–$C_4$alkyl), or said radicals are substituted by $C_1$–$C_{12}$alkoxy, $C_1$–$C_4$alkoxy, which is substituted by —COO($C_1$–$C_8$alkyl) or —CO(OCH$_2$CH$_2$)$_n$OCH$_3$, or said radicals are substituted by —(OCH$_2$CH$_2$)$_n$OH, —(OCH$_2$CH$_2$)$_n$OCH$_3$, $C_1$–$C_8$alkylthio, phenoxy, —COO($C_1$–$C_{18}$alkyl), —CO(OCH$_2$CH$_2$)$_n$OCH$_3$, phenyl or benzoyl;

n is 1 to 20;

m is 2 to 20;

provided that at least one of the radicals Ar, $Ar_1$, $Ar_2$, $Ar_3$, $R_1$, $R_2$, $R_3$, $R_4$, $R_5$ or Y is substituted by 1 to 5 SH groups, or provided that Y contains at least one —SS— group; or an acid addition salt of a compound of the formula I, II, III or IV.

Examples of the component (a) as a polymer or oligomer having at least two ethylenically unsaturated groups and at least one carboxyl function within the molecule structure are acid modified epoxyacrylate (for example, EB9696; UCB Chemicals, KAYARAD TCR1025; NIPPON KAYAKU CO., LTD.) and acrylated acrylcopolymer (for example, ACA200M; Daicel Chemical Industries, Ltd.).

Preferred compounds of the formula I, II, III and IV are indicated above.

As diluent, a mono- or multi-functional ethylenically unsaturated compound, or mixtures of several of said compounds, can also be included in the above composition up to 70% by weight based on the solid portion of the composition. The content of (b) is 0.5–20% by weight based on the solid portion of the composition.

It is also possible to add binders to the compositions according to the invention; this is particularly expedient if the photopolymerizable compounds are liquid or viscous substances. The quantity of binder may be for example, 5–95% by weight, preferably 10–90% by weight and, in particular, 40–90% by weight, based on the overall solids content. The binder is chosen depending on the field of application and on the properties required therefor, such as the facility for development in aqueous and organic solvent systems, adhesion to substrates and sensitivity to oxygen.

Examples of suitable binders are polymers having a molecular weight of about 5000–2,000,000, preferably 10,000–1,000,000. Examples are homo- and copolymeric acrylates and methacrylates, for example copolymers of methyl methacrylate/ethyl acrylate/methacrylic acid, poly(alkyl methacrylates), poly(alkyl acrylates); cellulose esters and cellulose ethers, such as cellulose acetate, cellulose acetate butyrate, methylcellulose and ethylcellulose; polyvinylbutyral, polyvinylformal, cyclized rubber, polyethers, such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds may also be used in mixtures with non-photopolymerizable film-forming components. These may be, for example, physically drying polymers or solutions thereof in organic solvents, for example nitrocellulose or cellulose acetobutyrate. However, they may also be chemically curable or heat-curable resins such as, for example, polyisocyanates, polyepoxides or melamine resins. The additional use of heat-curable resins is important for use in so-called hybrid systems, which are photopolymerized in a first step and crosslinked by thermal aftertreatment in a second step.

The photopolymerizable mixtures may contain various additives in addition to the photoinitiator. Examples thereof are thermal inhibitors, which are intended to prevent premature polymerization, for example the hydroquinone, hydroquinone derivatives, p-methoxyphenol, β-naphthol or sterically hindered phenols such as 2,6-di(tert-butyl)-p-cresol. The shelf life in the dark can be increased, for example, by using copper compounds such as copper naphthenate, copper stearate or copper octanoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, paraffin or similar wax-like substances can be added; these migrate to the surface on commencement of the polymerization because of their low solubility in the polymer, and form a transparent surface layer which prevents the ingress of air. Light stabilizers which can be added in small quantities are UV absorbers, for example those of the benzotriazole, benzophenone, oxalanilide or hydroxyphenyl-s-triazine type. These compounds can be employed individually or as mixtures, with or without the use of sterically hindered amines (HALS).

Examples of such UV absorbers and light stabilizers are:
1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3- tetramethylbutyl)-6-benzotriazol-2-yl phenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl phenyl.

2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl and isooctyl α-cyano-β,β-diphenylacrylate, methyl α-carbo-methoxycinnamate, methyl and butyl α-cyano-β-methyl-p-methoxycinnamate, methyl α-carbo-ethoxy-p-methoxycinnamate and N-(β-carbomethoxy-β-cyanovinyl)-2-methylindoline.

5. Sterically hindered amines, for example bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the product of the condensation of N,N'-bis(2,2,6,6-tetramethyl-4-piperidyl) hexamethylene diamine and 4-morpholino-2,6-dichloro-1,3,5-triazine, the product of the condensation of 2-chloro-4,6-di(4-n-butyl-amino-2,2,6,6-tetramethyl-piperidyl)-1,3,5-triazine and 1,2-bis(3-aminopropylamino)ethane, the product of the condensation of 2-chloro-4,6-di(4-n-butylamino-1,2,2,6,6-pentamethylpiperidyl)- 1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxy-propyloxy )phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethyl-phenyl)-1,3,5-triazine.

8. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythrityl diphosphite, tris(2,4-di-tert-butylphenyl)phosphite, diisodecylpentaerythrityl diphosphite, bis(2,4-di-tert-butylphenyl) pentaerythrityl diphosphite, bis(2,6-di-tert-butyl-4-methylphenyl)pentaerythrityl diphosphite, bisisodecyloxypentaerythrityl diphosphite, bis(2,4-di-tert-butyl-6-methylphenyl)pentaerythrityl diphosphite, bis(2,4,6-tri-tert-butylphenyl)pentaerythrityl diphosphite, tristearyl sorbityl triphosphite, tetrakis(2,4-di-tert-butylphenyl)-4,4'-biphenylenediphosphonite, 6-isooctyloxy-2,4,8,10-tetratert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis(2,4-di-tert-butyl-6-methylphenyl)methyl phosphite, and bis(2,4-di-tert-butyl-6-methylphenyl)ethyl phosphite.

To accelerate the photopolymerization it is possible to add amines such as, for example, triethanolamine, N-methyldiethanolamine, ethyl p-dimethylaminobenzoate or Michler's ketone. The action of the amines can be intensified by the addition of aromatic ketones of the benzophenone type. Examples of amines which can be used as oxygen scavengers are substituted N,N-dialkylanilines as described in EP-A-339841.

The photopolymerization can also be accelerated by addition of photosensitizers or coinitiators which shift or broaden the spectral sensitivity. These are, in particular, aromatic carbonyl compounds such as benzophenone derivatives, thioxanthone derivatives, anthraquinone derivatives and ketocoumarin derivatives, especially 3-ketocoumarin derivatives and 3-(aroylmethylene) thiazolines, and also eosin, rhodanine and erythrosine dyes.

The invention therefore also pertains to a photopolymerizable composition comprising in addition to components (a) and (b) at least one coinitiator (c). The coinitiator is preferably a thioxanthone or ketocoumarine, especially a 3-ketocoumarine, compound. The amount of component (c) in the composition according to the invention varies from 0.01 to 10% by weight, preferably 0.05 to 5.0% by weight, based on the solid portion of the composition.

The curing process may be assisted, in particular, by compositions pigmented with TiO$_2$, for example, but also by addition of a component which forms free radicals under thermal conditions, for example an azo compound such as 2,2'-azobis(4-methoxy-2,4-dimethylvaleronitrile) or a peroxy compound such as a hydroperoxide or peroxycarbonate, for example t-butyl hydroperoxide, as described in EP-A245639.

The compositions according to the invention may also contain a photoreducible dye, for example a xanthene, benzoxanthene, benzothioxanthene, thiazine, pyronine, porphyrin or acridine dyes, and/or a trihalomethyl compound which can be cleaved by radiation. Similar compositions are described in, for example, EP-A-445624.

Other conventional additives are—depending on the application—optical brighteners, fillers, pigments, dyes, wetting agents or levelling assistants. Thick and pigmented coatings can suitably be cured by the addition of glass microbeads or powdered glass fibres, as described in U.S. Pat. No. 5,013,768, for example.

The invention also relates to compositions comprising as component (a) at least one ethylenically unsaturated, photopolymerizable compound which is emulsified or dissolved in water.

Radiation-curable, aqueous prepolymer dispersions of this type are commercially available in many variations. This term is taken to mean a dispersion of water and at least one prepolymer dispersed therein. The concentration of the water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymer in these compositions is in each case 100, to which are added the assistants and additives in various amounts depending on the application.

The radiation-curable, water-dispersed, film-forming prepolymers, which are frequently also dissolved, are, for aqueous prepolymer dispersions, monofunctional or polyfunctional ethylenically unsaturated prepolymers which are known per se, can be initiated by means of free radicals and contain, for example, from 0.01 to 1.0 mol of polymerizable double bonds per 100 g of prepolymer, and have an average molecular weight of, for example, at least 400, in particular from 500 to 10,000. Depending on the intended application, however, prepolymers having higher molecular weights may also be suitable. For example, polyesters containing polymerizable C—C double bonds and having a maximum acid number of 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates and α,β-ethylenically unsaturated acrylic copolymers containing acrylic radicals, as described in EP-A-12339, are used. Mixtures of these prepolymers may also be used. Also suitable are the polymerizable prepolymers described in EP-A-33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific alkyl(meth)acrylate polymers are described in EP-A-41125, and suitable water-dispersible, radiation-curable prepolymers made from urethane acrylates are disclosed in DE-A-2936039.

These radiation-curable, aqueous prepolymer dispersions may contain, as further additives, dispersion assistants, emulsifiers, antioxidants, light stabilizers, dyes, pigments, fillers, for example talc, gypsum, silica, rutile, carbon black, zinc oxide and iron oxides, reaction accelerators, levelling agents, lubricants, wetting agents, thickeners, matting agents, antifoams and other assistants which are conventional in surface-coating technology. Suitable dispersion assistants are water-soluble, high molecular weight organic compounds containing polar groups, for example polyvinyl alcohols, polyvinylpyrrolidone and cellulose ethers. Emulsifiers which can be used are nonionic emulsifiers and possibly also ionic emulsifiers.

Subject matter of the invention also is a composition comprising in addition to the components (a) and (b) at least one further photoinitiator (d) and/or other additives.

In certain cases it may be of advantage to use mixtures of two or more of the photoinitiators according to the invention. It is of course also possible to use mixtures with known photoinitiators, for example mixtures with benzophenone, acetophenone derivatives, for example α-hydroxycycloalkylphenyl ketones, dialkoxyacetophenones, α-hydroxy- or other α-aminoacetophenones, 4-aroyl-1,3-dioxolanes, benzoin alkyl ethers and benzil ketals, monoacylphosphine oxides, bisacylphosphine oxides, xanthones, thioxanthones, anthraquinones or titanocenes. When the photoinitiators according to the invention are employed in hybrid systems, cationic photoinitiators such as aromatic sulfonium or iodonium salts or cyclopentadienylareneiron(II) complex salts are used in addition to the free-radical curing agents according to the invention.

The invention is further directed to a composition comprising in addition to components (a) and (b) at least one dye-borate compound and/or borate salt and optionally an onium compound.

Suitable dye-borate compounds are for example disclosed in U.S. Pat. No. 4,751,102, U.S. Pat. No. 5057393, U.S. Pat. No. 5,151,520. Combinations of borate salts with dye-borates are, for example described in U.S. Pat. No. 5,176,984.

Suitable onium salts in these mixtures are, for example, diphenyliodonium hexafluorophosphate, (p-octyloxyphenyl)(phenyl)iodonium hexafluorophosphate, or corresponding other anions of these compounds, for example the halides; and also sulfonium salts, for example triarylsulfonium salts (Cyracure® UVI 6990, Cyracure® UVI-6974 from Union Carbide; Degacure® KI 85 from Degussa or SP-150 und SP-170 from Asahi Denka).

The photopolymerizable compositions contain the photoinitiator or the photoinitiator mixture (b) advantageously in a quantity of from 0.05 to 15% by weight, preferably from 0.1 to 5% by weight, based on the composition. Or, if additionally a component (d) is present, the sum of the quantity of the components (b) and (d) is advantageously from 0.05 to 15% by weight, preferably from 0.1 to 5% by weight, based on the composition.

The photopolymerizable compositions can be used for various purposes, for example as printing inks, as varnishes or clearcoats, as white paints, for example for wood or metal, as coating substances, inter alia, for paper, wood, metal or plastic, as daylight-curable coatings for buildings and roadmarking, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as etch resists or permanent resists and as solder masks for electronic circuits, for the production of three-dimensional articles by bulk curing (UV curing in transparent moulds) or by the stereolithography process, as described, for example, in U.S. Pat. No. 4,575,330, for the preparation of composite materials (for example styrenic polyesters, which may contain glass fibres and other assistants) and other thick-layer compositions, for the coating or encapsulation of electronic components or as coatings for optical fibres. The compounds according to the invention may also be used as initiators for emulsion polymerizations, as initiators of a polymerization for the fixing of ordered states of liquid-crystalline mono- and oligomers, as initiators for the fixing of dyes to organic materials, and for curing powder coatings.

In coating materials, mixtures of a prepolymer with polyunsaturated monomers are often used which also contain a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent by means of which the viscosity is reduced without the need to use a solvent.

Unsaturated polyester resins are mostly used in two-component systems in conjunction with a monounsaturated monomer, preferably styrene. For photoresists, specific one-component systems are frequently employed, for example polymaleimides, polychalcones or polyimides, as described in DE-A2308830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamidoglycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator (or mixture of photoinitiators) according to the invention. The powder coatings may also contain binders as described for example in DE-A-4228514 or EP-A-636669. The UV-curable powder coatings may also comprise white or coloured pigments. Thus, for example, preferably rutile titanium dioxide can be employed in concentrations of up to 50% by weight in order to give a cured powder coating having good covering power. The process normally comprises electrostatic or tribostatic spraying of the powder onto the substrate, for example of metal or wood, melting the powder by heating and, after a smooth film has been formed, radiation-curing of the coating using ultraviolet and/or visible light, for example with medium-pressure mercury lamps, metal halide lamps or xenon lamps. A particular advantage of the radiation-curable powder coatings over their heat-curable counterparts is that the flow time after the melting of the powder particles can be selectively extended in order to ensure the formation of a smooth, high-gloss coating. In contrast to heat-curable systems, radiation-curable powder coatings can be formulated without the unwanted effects of a reduction in their lifetime so that they melt at relatively low temperatures. For this reason, they are also suitable as coatings for heat-sensitive substrates such as wood or plastics.

In addition to the photoinitiators according to the invention, the powder coating formulations may also contain UV absorbers. Appropriate examples have been listed above under items 1–8.

The photocurable compositions according to the invention are suitable, for example, as coating substances for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$, on which it is desired to apply a protective coating or, by imagewise exposure, an image.

The substrates can be coated by applying a liquid composition, a solution or suspension to the substrate. The choice of the solvent and the concentration depend predominantly on the type of composition and the coating procedure. The solvent should be inert: in other words it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. Using known coating processes, the solution is applied evenly to a substrate, for example by spincoating, dip coating, knife coating, curtain coating, brushing, spraying, especially electrostatic spraying, and reverse roll coating. It is also possible to apply the photosensitive layer to a temporary, flexible support and then to coat the final substrate, for example a copper-laminated circuit board, by means of layer transfer via lamination.

The quantity applied (layer thickness) and the nature of the substrate (layer support) are functions of the desired application. The range of coat thicknesses generally comprises values from about 0.1 µm to more than 100 µm.

The radiation-sensitive compositions according to the invention find application as negative resists which have a very high photosensitivity and can be developed in an aqueous-alkaline medium without swelling. They are suitable as photoresists for electronics (galvanoresists, etch resists and solder resists), the production of printing plates such as offset printing plates or screen printing formes, and can be used for chemical milling or as microresists in the production of integrated circuits. There is a correspondingly wide range of variation in the possible layer supports and the processing conditions for the coated substrates.

The compounds according to the invention also find application for the production of one- or more-layered materials for the image recording ore image reproduction (copies, reprography), which may be uni- or polychromatic. Furthermore the materials are suitable for colour proofing systems. In this technology formulations containing microcapsules can be applied and for the image production the radiation curing can be followed by a thermal treatment. Such systems and technologies and their applications are for example disclosed in U.S. Pat. No. 5,376,459.

Examples of the layer supports for photographic information recordings are films made of polyester, cellulose acetate or plastic-coated papers; for offset printing plates, specially treated aluminium; for the production of printed circuits, copper-faced laminates; and for the production of integrated circuits, silicon wafers. The layer thicknesses for photographic materials and offset printing plates are generally from about 0.5 µm to 10 µm, while for printed circuits they are from 1.0 µm to about 100 µm.

Following the coating of the substrates, the solvent is generally removed by drying to leave a layer of the photoresist on the substrate.

The term "imagewise exposure" relates both to exposure through a photomask containing a predetermined pattern, for example a slide, exposure by a laser beam which is moved under control from a computer, for example, over the surface of the coated substrate, thereby generating an image, and irradiation with computer-controlled electron beams.

Following the imagewise exposure of the material and prior to developing, it may be advantageous to carry out a brief thermal treatment, in which only the exposed parts are thermally cured. The temperatures employed are generally 50–150° C. and preferably 80–130° C.; the duration of the thermal treatment is generally between 0.25 and 10 minutes.

The photocurable composition can also be used in a process for the production of printing plates or photoresists as described, for example, in DE-A-4013358. In this process the composition is exposed before, simultaneously with or after the imagewise irradiation, exposure being carried out for a short period with visible light at a wavelength of at least 400 nm without a mask.

Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small quantities of wetting agents and/or organic solvents may also be added, if desired, to these solutions. Examples of typical organic solvents which may be added in small quantities to the developing liquids are cyclohexanone, 2-ethoxyethanol, toluene, acetone and mixtures of such solvents.

Photocuring is of considerable importance for printing inks, since the drying time of the binder is a crucial factor for the production rate of graphic products and should be in the order of fractions of seconds. UV-curable inks are important, in particular, for screen printing.

Subject of the invention therefore also is a printing ink comprising a composition as described above and a pigment or a dye and optionally a sensitizer, preferably a thioxanthone or a derivative thereof.

The printing inks according to the invention contain a pigment or a dye. Suitable pigments or dyes are known to the person skilled in the art. The pigment is, for example, an inorganic pigment, e.g. titanium dioxide (rutile or anatase), iron yellow, iron red, chrome yellow, chrome green, nickel-titanium yellow, ultramarine blue, cobalt blue, cadmium yellow, cadmium red or zinc white. Or, the pigment is, for example, an organic pigment, e.g. a monoazo or bisazo pigment or a metal complex thereof, a phthalocyanine pigment or a poylcyclic pigment, for example a perylene, thioindigo, flavanthrone, quinacridone, tetrachloroisoindolinone or triphenylmethane pigment. Or, the pigment is a carbon black or a metal powder, for example aluminum or copper powder, or any other pigment known to be useful in the printing technology. The pigment employed may also be a mixture of one or more pigments, such as is customary for achieving specific colour shades. The pigment or pigment mixture is present in an amount customary in the printing ink technology, for example in an amount of 5 to 60% by weight, based on the total composition; preferably 10–30% by weight of pigment are present in a printing ink. Suitable dyes belong, for example, to a very wide variety of classes, for example azo dyes, methine dyes, anthraquinone dyes or metal complex dyes. Ion the concentrations used, these dyes are soluble in the particular binders. The customary concentrations are, for example, from 0.1 to 20%, preferably 1–5% by weight, based on the total composition.

As already mentioned, the mixtures according to the invention are also highly suitable for the production of printing plates, where, for example, mixtures of soluble, linear polyamides or styrene/butadiene or styrene/isoprene rubber, polyacrylates or polymethyl methacrylates containing carboxyl groups, polyvinyl alcohols or urethane acrylates are used with photo-polymerizable monomers, for example acrylamides, methacrylamides, acrylates or methacrylates, and a photoinitiator. Films and plates made from these systems (wet or dry) are exposed through the negative (or positive) of the print original, and the uncured parts are subsequently washed out using a suitable solvent.

A further area of application for photocuring is the coating of metals, for example in the coating of metal sheets and tubes, cans or bottle caps, and the photocuring of plastic coatings, for example PVC-based wall or floor coverings.

Examples of the photocuring of paper coatings are the colourless coating of labels, record sleeves or book covers.

The use of the compounds according to the invention for curing shaped articles made from composite compositions is likewise of interest. The composite composition is made up of a self-supporting matrix material, for example a glass-fibre fabric, or else, for example, plant fibres [cf. K.-P. Mieck and T. Reussmann in Kunststoffe 85 (1995), 366–370], which is impregnated with the photocuring formulation. Shaped articles which are produced from composite compositions, using the compounds according to the invention, are of high mechanical stability and resistance. The compounds according to the invention can also be employed as photocuring agents in moulding, impregnating and coating compositions, as described, for example, in EP-A-7086. Examples of such compositions are fine coating resins on which stringent requirements are placed with respect to their curing activity and yellowing resistance, or fibre-reinforced mouldings such as planar or longitudinally or transversely corrugated light diffusing panels. Processes for the production of such mouldings, for example hand lay-up, spray lay-up, centrifugal or filament winding processes, are described by, for example P. H. Selden in "Glasfaserverstärkte Kunststoffe" [Glass fibre-reinforced plastics], page 610, Springer Verlag Berlin-Heidelberg-New York 1967. Examples of articles for use which can be produced by this process are boats, chipboard or plywood panels coated on both sides with glass fibre-reinforced plastic, pipes, containers and the like. Other examples of moulding, impregnating and coating compositions are UP resin fine coatings for mouldings containing glass fibres (GRP), e.g. corrugated sheets and paper laminates. Paper laminates may also be based on urea or melamine resins. The fine coating is produced on a support (for example a film) prior to the production of the laminate. The photocurable compositions according to the invention can also be used for casting resins or for encapsulating articles such as electronic components and the like. Curing employs medium-pressure mercury lamps as are conventional in UV curing. However, less intense lamps are also of particular interest, for example those of the type TL40W/03 or TL40W/05. The intensity of these lamps corresponds approximately to that of sunlight. Direct sunlight can also be used for curing. A further advantage is that the composite composition can be removed from the light source in a partially cured, plastic state and can be deformed. Curing is subsequently carried out to completion.

The compositions and compounds according to the invention can be used for the production of waveguide and optical switches wherein advantage is taken of the development of a difference in the index of refraction between irradiated and unirradiated areas.

Also important is the use of photocurable compositions for imaging processes and for the optical production of information carriers. In these applications, the coat (wet or dry) applied to the support is irradiated—as already described above—with UV or visible light through a photomask and the unexposed areas of the coat are removed by treatment with a solvent (=developer). The photocurable layer can also be applied by electrodeposition to metal. The exposed areas are crosslinked/polymeric and thus insoluble and remain on the support. If appropriate colouration is carried out, visible images are formed. If the support is a metallized layer, then the metal can be removed from the unexposed areas by etching after exposure and development or can be increased in thickness by electroplating. In this way, printed electronic circuits and photoresists can be produced.

The photosensitivity of the compositions according to the invention generally ranges from the UV region (about 200 nm) up to about 600 nm, and therefore spans a very wide range. Suitable radiation comprises, for example, sunlight or light from artificial sources. Therefore, a large number of very different types of light source can be used. Both point sources and flat radiators (lamp carpets) are appropriate. Examples are: carbon arc lamps, xenon arc lamps, medium-pressure, high-pressure and low-pressure mercury lamps, doped with metal halides if desired (metal halogen lamps), microwave-stimulated metal vapour lamps, excimer lamps, superactinic fluorescent tubes, fluorescent lamps, incandescent argon lamps, electronic flashlights or photographic flood lamps. Also other types of radiation, e.g. electron beams and X-rays, produced by means of synchrotrons, or laser plasma are suitable. The distance between the lamp and the substrate according to the invention which is to be exposed can vary depending on the application and on the type and/or power of the lamp, for example from between 2 cm and 150 cm. Of particular suitability are laser light sources, for example excimer lasers, such as krypton F lasers for exposure at 248 nm. Lasers in the visible range may also be employed. In this case the high sensitivity of the materials according to the invention is very advantageous. By this method it is possible to produce printed circuits in the electronics industry, lithographic offset printing plates or relief printing plates, and photographic image recording materials.

The invention likewise relates to the use of compounds of the formula I, II, III and IV for the curing of shaped articles made from composite compositions, and to a process of curing shaped articles made from composite compositions using the above-defined compounds of the formula I, II, III and IV.

The invention also relates to the use of a composition according to the invention for producing pigmented and nonpigmented paints and varnishes, for producing clear and pigmented aqueous dispersions, powder coatings, printing inks, printing plates, adhesives, dental filling compositions, waveguides, optical switches, colour proofing systems, glass fibre cable coatings, screen printing stencils, resist materials, composite compositions, for photographic reproductions, for producing masks for screen printing, for photoresists for printed electronic circuits, for encapsulating electrical and electronic components, for producing magnetic recording materials, for producing three-dimensional objects by means of stereolithography or bulk-curing, and as image recording material, especially for holographic recordings.

The invention additionally relates to a process for the photopolymerization of nonvolatile monomeric, oligomeric or polymeric compounds containing at least one ethylenically unsaturated double bond, which comprises adding at least one compound of the formula I, II, III or IV to said compounds and irradiating the resulting composition with light having a wavelength ranging from 200 to 600 nm.

In accordance with the invention this process is also used for the production of coating substances, especially white paints for wood coatings and metal coatings, or clear coating materials, for the production of coating materials for daylight-curable constructional coatings and road markings, for the production of composite materials, for the production of printing plates, for the production of masks for screen printing, for the production of photoresists for printed electronic circuits, for the production of adhesives, for the production of coatings for optical fibres, for the production of coatings or encapsulations of electronic components, and in the method of bulk curing or stereolithography.

The invention likewise relates to a coated substrate which is coated on at least one surface with a cured composition as described above, and to a process for the photographic production of relief images in which a coated substrate is subjected to imagewise exposure and then the unexposed areas are removed with a solvent or exposing a coated substrate by means of a movable laser beam (without a mask) and then removing the unexposed areas with a solvent.

The compounds according to the invention can be dissolved very readily in the mixtures to be polymerized, and are of only very low volatility. They exhibit a good sensitivity, especially as initiators in solder resists, and satisfactory yellowing values of the compositions cured using the compounds according to the invention are achieved.

The Examples that follow further illustrate the invention. As in the remainder of the description and in the patent claims, unless otherwise indicated data in parts or percentages are based on the weight. Where in the designations of alkyl radicals having more than 3 carbon atoms no specific isomers are indicated, these radicals are in each the n-isomers.

EXAMPLE 1

1-[4-(3-Mercaptopropylthio)phenyl]-2-methyl-2-morpholine-4-yl-propan-1-one 1a (4-Fluorophenyl)-3,3-dimethyl-2-methoxyoxirane 100.32 g (0.41 mol) of 2-bromo-1-(4-fluorophenyl)-2-methylpropan-1-one, prepared by brominating 1-(4-fluorophenyl)-2-methylpropan-1-one (as is described in EP-A-3002), are dissolved in 80 ml of dry methanol and 24.3 g (0.45 mol) of sodium methoxide in a solvent mixture of 60 ml dry methanol and 120 ml of chlorobenzene are added dropwise at 20° C. The methanol is then distilled off and the chlorobenzene solution is concentrated. The liquid crude product (90.8 g) is further purified by distillation at 60° C. and 0.2 mm Hg.

1b 1-(4-Fluorophenyl)-2-methyl-2-morpholine-4-yl-propan-1-one 69.3 g (0.35 mol) of (4-fluorophenyl)-3,3-dimethyl-2-methoxyoxirane and 200 ml of dry morpholine are mixed and heated to reflux temperature (about 130° C.). After 26 h, the unreacted excess morpholine is distilled off. The residue is taken up in toluene and washed with water and saturated sodium chloride solution successively. The toluene solution is dried with $MgSO_4$ and is concentrated. The residue, 88.1 g, crystallizes from ethanol with a melting point of 63–66° C.

1c 1-[4-(3-mercaptopropylthio)phenyl]-2-methyl-2-morpholine-4-yl-propan-1-one 52.8 g (0.488 mol) of 1,3-propanedithiol are dissolved in 100 ml of dry dimethylacetamide, 22.0 g of potassium carbonate are added and the solution is heated to about 40° C. 20.0 g (0.08 mol) of 1-(4-fluorophenyl)-2-methyl-2-morpholine-4-yl-propan-1-one in 50 ml of dry dimethylacetamide are added dropwise over 14 h. The resulting suspension is stirred for additional 5 h, then the solid is filtered off and washed with toluene. From the filtrate the excess 1,3-propanedithiol and toluene are distilled off. The residue is dissolved in ethyl acetate and the resulting solution is washed with saturated ammonium chloride solution, is dried over $MgSO_4$ and concentrated. The residue is recrystallized from ethanol. The obtained product has a melting point of 67–68° C. The structure is confirmed by the $^1$H-NMR-spectrum, measured in $CDCl_3$. The signals ($\delta$ in ppm) are 1.31 (s, 6H), 1.39 (t, 1H), 2.00 (m,2H), 2.57 (t,4H), 2.70 (q,2H), 3.13 (t,2H), 3.69 (t,4H), 7.28 (d,2H), 8.50 (d, 2H).

EXAMPLE 2

1-[4-(mercaptoethylthio)phenyl]-2-methyl-2-morpholine-4-yl-propane-1-one 22.5 g (0.24 mol) of 1,2-ethanedithiol are dissolved in 70 ml of dry dimethylacetamide, 10.0 g of potassium carbonate are added and the solution is heated to about 40° C. 10.1 g o(0.04 mol) of 1-(4-fluorophenyl)-2-methyl-2-morpholine-4-yl-propane-1-one (prepared as described in example 1b) in 30 ml of dry dimethylacetamide are added dropwise. The suspension is stirred for 5 h, then the solid is filtered off and washed with toluene. From the filtrate the excess 1,2-ethanedithiol and toluene are distilled off. The residue is purified by column chromatography on silica gel with ethyl acetate-hexane (20:80) as eluent. The resulting product has a melting point of 92–93° C. The structure is confirmed by the $^1$H-NMR-spectrum, measured in $CDCl_3$. The signals ($\delta$ in ppm) are 1.31 (s,6H), 1.75 (t, 1H), 2.57 (t,4H), 2.80 (q,2H), 3.21 (t,2H), 3.70 (t,4H), 7.29 (d,2H), 8.51 (d,2H).

EXAMPLE 3

1-[4-(4-mercaptophenylthio)phenyl]-2-methyl-2-morpholine-4-yl-propane-1-one 20.0 g (0.14 mol) of 1,3-benzenedithiol are dissolved in 50 ml of dry dimethylacetamide, 14.0 g of potassium carbonate are added and the resulting solution is heated to about 45° C. 7.2 g (0.029 mol) of 1-(4-fluorophenyl)-2-methyl-2-morpholine-4-yl-propane-1-one (prepared as described in example 1b) in 40 ml of dry dimethylacetamide are added dropwise. The suspension is stirred for 17 h, then the solid is filtered off and washed with methylene chloride. From the filtrate the solvent and the excess 1,3-benzenedithiol are distilled off. The residual oil is purified by column chromatography on silica gel with ethyl acetate-hexane (20:80) as eluent. The structure is confirmed by the $^1$H-NMR-spectrum, measured in CDCl$_3$. The signals (δ in ppm) are 1.30 (s,6H), 2.56 (t,4H), 3.52 (s, 1H), 3.68 (t,4H), 7.19 (d,2H), 7.26 (s,3H), 7.40 (s,1H), 8.47 (d,2H).

EXAMPLE 4

1-[4-(2,3-dihydroxy-4-mercaptobutylthio)phenyl]-2-methyl-2-morpholine-4-yl-propane-1-one 1.0 g (4.0 mmol) of 1-[4-(4-mercaptophenylthio)phenyl]-2-methyl-2-morpholine-4-yl-propane-1-one and 1.37 g (8.9 mmol) of 1,4-dimercapto-2,3-butanediol are dissolved in 50 ml of dry dimethylacetamide, 1.10 g (8.0 mmol) of potassium carbonate are added and the mixture is stirred for 17 h. The resulting suspension is poured into water and extracted with ethyl acetate, the combined organic phases are washed with water. The solvent is distilled off and the residual oil is purified by column chromatography on silica gel with ethanol-methylene chloride (5:95) as eluent. The structure is confirmed by the $^1$H-NMR-spectrum, measured in CDCl$_3$. The signals (δ in ppm) are 1.31 (s,6H), 1.55 (t,1 H), 2.57 (m,4H), 2.75 (m, 1H), 3.24 (m,5H), 3.70 (m,5H), 4.18 (s,1H), 7.53 (d,2H), 8.49 (d,2H).

EXAMPLE 5

1-[3-(Mercaptopropylthio)phenyl]-2-dimethylamino-2-benzyl-propan-1-one 5a 1-(4-Fluorophenyl) 2-dimethylamino-2-benzyl-propan-1-one 11.2 g of sodium hydride (66%) are washed with hexane to remove oil, and added to 200 ml of dry dimethylacetamide. 50.0 g (0.256 mol) of 1-(4-fluorophenyl)-2-dimethylamino-propan-1-one (prepared by the method described in U.S. Pat. No. 5,534,629) are dissolved in 50 ml of dry dimethylacetamide and added dropwise to the above described solution. Successively, 48.2 g (0.282 mol) of benzyl bromide are slowly added dropwise with stirring and warmed up to 105° C. When the mixture has been stirred at this temperature for 12 h, the reaction mixture is poured to 500 ml of ice/water and extracted with toluene. The organic phase is washed with water, dried over MgSO$_4$ and evaporated. The residue is purified by column chromatography on silica gel with ethyl acetate-hexane (1:20) as eluent. The structure is confirmed by the $^1$H-NMR-spectrum, measured in CDCl$_3$. The signals (δ in ppm) are 1.17 (s,3H), 2.33 (s,6H), 2.96 (d, 1H), 3.39 (d, 1H), 6.87 (m,2H), 7.03–7.13 (m,5H), 8.55 (m, 2H).

5b 1-[3-(Mercaptopropylthio)phenyl]-2-dimethylamino-2-benzyl-propan-1-one 22.8 g (0.21 mol) of 1,3-propandithiol is dissolved in 50 ml of dry dimethylacetamide, 4.8 g of potassium carbonate are added and the mixture is heated to about 50° C. 10.0 g of 1-(4-fluorophenyl) 2-dimethylamino-2-benzyl-propan-1-one in 50 ml of dry dimethylacetamide are added dropwise. The suspension is stirred at 50° C. for 12 h, the solid is filtered off. The excess 1,3-propanedithiol and dimethylacetamide are distilled off. To the residue toulene is added and the resulting precipitate is filtered off. After the toluene is distilled off, the residue is purified by column chromatography on silica gel with ethyl acetate-hexane (1:9) as eluent. The structure is confirmed by the $^1$H-NMR-spectrum, measured in CDCl$_3$. The signals (δ in ppm) are 1.16 (s,3H), 1.40 (t, 1H), 2.02 (m,2H), 2.34 (s,6H), 2.71 (q,2H), 2.96 (d, 1H), 3.14 (t,2H), 3.68 (d,1H), 6.88 (m,2H), 7.12 (m,3H), 7.29 (d,2H), 8.44 (d,2H).

EXAMPLE 6

1-[4-(3-Mercaptopropylthio)phenyl]-2-dimethylamino-2-methylpent-4-en-1-one 6a 1-(4-Fluorophenyl)-2-dimethylamino-2-methylpent-4-en-1-one 11.2 g of sodium hydride (66%) are washed with hexane to remove oil, and added to 200 ml of dry dimethylacetamide. 50.0 g (0.256 mol) of 1-(4-fluorophenyl)-2-dimethylamino-propan- 1-one (prepared by the method described in U.S. Pat. No. 5,534,629) are dissolved in 50 ml of dry dimethylacetamide and added dropwise to the above described solution. Successively, 34.1 g (0.282 mol) of ally bromide are slowly added dropwise with stirring and warmed up to 105° C. When the mixture has been stirred at this temperature for 12 hours, the reaction mixture is poured to 500 ml of ice/water and extracted with toluene. The organic phase is washed with water, dried over MgSO$_4$ and evaporated. The residue is purified by column chromatography on silica gel with ethyl acetate-hexane (1:9) as eluent. The structure is confirmed by the $^1$H-NMR-spectrum, measured in CDCl$_3$. The signals (δ in ppm) are 1.19 (s,3H), 2.28 (sw,6H), 2.42 (m, 1H), 2.70 (m, 1H), 4.79–4.93 (m,2H), 5.51 (m, 1H), 7.05 (m,2H), 8.53 (d,2H).

6b 1-[4-(3-Mercaptopropylthio)phenyl]-2-dimethylamino-2-methylpent-4-en-1-one 25.0 g (0.23 mol) of 1,3-propandithiol are dissolved in 80 ml of dry dimethylacetamide and 6.0 g of potassium carbonate are added. 10.0 g of 1-(4-fluorophenyl)-2-dimethylamino-2-methylpent-4-en-1-one in 20 ml of dry dimethylacetamide are added dropwise. The suspension is stirred at 50° C. for 12 h, the solid is filtered off. The excess 1,3-propanedithiol and dimethylacetamide are distilled off. To the residue toluene is added and the precipitate is filtered off. After toluene is distilled off, the residue is purified by column chromatography on silica gel with ethyl acetate-hexane (1:10) as eluent and an oily product is obtained. The structure is confirmed by the $^1$H-NMR-spectrum, measured in CDCl$_3$. The signals (δ in ppm) are 1.18 (s,3H), 1.39 (t,1H), 2.00 (m,2H), 2.27 (s,5H), 2.42 (m, 1H), 2.66–2.72 (m,3H), 3.12 (t,2H), 4.83–4.93 (m,2H), 5.52 (m, 1H), 7.26 (d,2H), 8.38 (d,2H).

EXAMPLE 7

1-[4-(3-Mercaptopropylthio)phenyl]-2-dimethylamino-2-benzyl-butan-1-one 32.5 g (0.3 mol) of 1,3-propanedithiol are dissolved in 50 ml of dry dimethylacetamide, and the solution is heated to about 50° C. together with 13.8 g (0.1 mol) of potassium carbonate. 15.0 g (0.05 mol) of 1-(4-fluorophenyl)-2-dimethylamino-2-benzyl-butan-1-one in 30 ml of dry dimethylacetamide are added dropwise. The suspension is stirred at 50° C. overnight (about 12 hours), then the solid is filtered off. The excess 1,3-propanedithiol and dimethylacetamide are distilled off. To the residue is added toluene, then the precipitate is filtered off. After distilling off the toluene, the residue is purified by means of column chromatography on silica gel with ethyl acetate-hexane (1:7) as an eluent, and an oily product is obtained. The structure is confirmed by the $^1$H-NMR spectrum (CDCl$_3$): δ [ppm]: 0.68 (t, 3H), 1.39 (t, 1H), 1.79–1.88 (m, 1H), 1.97–2.11 (m, 3H), 2.36 (s, 6H), 2.69 (q, 2H), 3.12 (t, 2H), 3.19 (s, 2H), 7.15–7.27 (m, 7H), 8.28 (d, 2H).

EXAMPLE 8

1-[4-(3-Mercaptopropylamino)phenyl]-2-dimethylamino-2-benzyl-propan-1-one 8a 1-[4-(3-Hydroxypropylamino)phenyl]-2-dimethylamino-2-benzyl-propan-1-one 10.0 g (0.035 mol) of 1-(4-fluorophenyl)-2-dimethylamino-2-benzyl-propan-1-one and 18.4 g (0.25 mol) of 3-amino-1-propanol are dissolved in 20 ml of dry dimethylacetamide, and the solution is heated up to 150° C. together with 9.7 g (0.07 mol) of potassium carbonate, and stirred overnight (about 12 hours). After the solution is cooled down, it is poured into 300 ml of water and extracted with toluene. The organic phase is washed with water and saturated sodium chloride solution, and dried over MgSO$_4$. After distilling off the toluene, the residue is purified by means of column chromatography on silica gel with ethyl acetate-hexane (1:1) as an eluent, and an oily product is obtained. The structure is confirmed by the $^1$H-NMR spectrum (CDCl$_3$): δ [ppm]:1.14 (s, 3H), 1.50 (br, 1H), 1.93 (m, 2H), 2.33 (s, 6H), 2.96 (d, 1H), 3.37 (m, 2H), 3.42 (d, 1H), 3.85 (m, 2H), 4.45 (br, 1H), 6.56 (d, 2H), 6.89–6.91 (m, 2H), 7.10–7.12 (m, 3H), 8.45 (d, 2H).

8b 1-[4-(3-Iodopropylamino)phenyl]-2-dimethylamino-2-benzyl-propan-1-one 6.7 g (0.02 mol) of 1-[4-(3-Hydroxypropylamino)phenyl]-2-dimethylamino-2-benzyl-propan-1-one, 3.35 g (0.05 mol) of imidazole and 12.9 g (0.05 mol) of triphenyl phosphine are dissolved in 50 ml of methylene chloride. To the solution are added 10 g (0.039 mol) of iodine and stirred at room temperature (about 20° C.) for 1 hour. 100 ml of methylene chloride is added to the reaction mixture and washed with aqueous solution of sodium sulfite and water, and dried over MgSO$_4$. After distilling off the methylene chloride, the residue is purified by means of column chromatography on silica gel with ethyl acetate-hexane (1:3) as an eluent, and an oily product is obtained. The structure is confirmed by the $^1$H-NMR spectrum (CDCl$_3$): δ [ppm]: 1.14 (s, 3H), 2.14 (m, 2H), 2.33 (s, 6H), 2.96 (d, 1H), 3.29 (t, 2H), 3.35–3.40 (m, 2H), 3.42 (d, 1H), 4.21 (br, 1H), 6.56 (d, 2H), 6.89–6.91 (m, 2H), 7.10–7.12 (m, 3H), 8.46 (d, 2H).

8c 1-[4-(3-Mercaptopropylamino)phenyl]-2-dimethylamino-2-benzyl-propan-1-one 6.6 g (0.015 mol) of 1-[4-(3-Iodopropylamino)phenyl]-2-dimethylamino-2-benzyl-propan-1-one are dissolved in 50 ml of dimethylacetamide. To the solution are added 2.42 g of potassium thioacetate and heated up to 50° C. After the reaction mixture is stirred at 50° C. for 2 h, it is poured into 100 ml of water and extracted with ethyl acetate. The organic phase is washed with water and saturated sodium chloride solution, and dried over MgSO$_4$. After distilling off the ethyl acetate, the residue is dissolved in 70 ml of ethanol and the solution is bubbled by nitrogen for 30 min. to remove oxygen. To the solution are added 7 ml of 2 N sodium hydroxide solution and stirred at 0° C. for 30 min. After the reaction mixture is neutralized by adding 2 N hydrochloric acid solution, the resulting solution is poured into 100 ml of water and extracted with ethyl acetate. The organic phase is washed with water and saturated sodium chloride solution, and dried over MgSO$_4$. After ethyl acetate is distilled off, the residue is purified by means of column chromatography on silica gel with ethyl acetate-hexane (1:2) as an eluent, and an oily product is obtained. The structure is confirmed by the $^1$H-NMR spectrum (CDCl$_3$): δ [ppm]: 1.14 (s, 3H), 1.43 (t, 1H), 1.97 (m, 2H), 2.33 (s, 6H), 2.68 (q, 2H), 2.96 (d, 1H), 3.34–3.39 (m, 2H), 3.42 (d, 1H), 4.18 (br, 1H), 6.57 (d, 2H), 6.89–6.92 (m, 2H), 7.10–7.12 (m, 3H), 8.46 (d, 2H).

EXAMPLE 9

1-[4-(3-Mercaptopropylamino)phenyl]-2-dimethylamino-2-benzyl-butan-1-one 9a 1-[4-(3-Hydroxypropylamino) phenyl]-2-dimethylamino-2-benzyl-butan-1-one 15.0 g (0.050 mol) of 1-(4-fluorophenyl)-2-dimethylamino-2-benzyl-butan-1-one and 26.3 g (0.35 mol) of 3-amino-1-propanol are dissolved in 30 ml of dry dimethylacetamide, and the solution is heated up to 150° C. together with 13.8 g (0.1 mol) of potassium carbonate, and stirred overnight (about 12 h). After the solution is cooled down, it is poured into 300 ml of water and extracted with ethyl acetate. The organic phase is washed with water and saturated sodium chloride solution, and dried over MgSO$_4$. After distilling off the ethyl acetate, the residue is purified by means of column chromatography on silica gel with ethyl acetate-hexane (1:1) as an eluent, and an oily product is obtained. The structure is confirmed by the $^1$H-NMR spectrum (CDCl$_3$): δ [ppm]: 0.68 (t, 3H), 1.52 (br, 1H), 1.82–1.94 (m, 3H), 2.00–2.07 (m, 1H), 2.35 (s, 6H), 3.17 (d, 1H), 3.20 (d, 1H), 3.32–3.37 (m, 2H), 3.81–3.85 (m, 2H), 4.42 (br, 1H), 6.52 (d, 2H), 7.14–7.28 (m, 5H), 8.32 (d, 2H).

9b 1-[4-(3-Iodopropylamino)phenyl]-2-dimethylamino-2-benzyl-butan-1-one 14.5 g (0.041 mol) of 1-[4-(3-Hydroxypropylamino)phenyl]-2-dimethylamino-2-benzyl-butan-1-one, 6.96 g (0.1 mol) of imidazole and 26.8 g (0.1 mol) of triphenyl phosphine are dissolved in 100 ml of methylene chloride. To the solution are added 20.8 g (0.082 mol) of iodine and stirred at room temperature (about 20° C.) for 20 min. 200 ml of methylene chloride are added to the reaction mixture and washed with aqueous solution of sodium sulfite and water, and dried over MgSO$_4$. After distilling off the methylene chloride, the residue is purified by means of column chromatography on silica gel with ethyl acetate-hexane (1:4) as an eluent, and an oily product is obtained. The structure is confirmed by the $^1$H-NMR spectrum (CDCl$_3$): δ [ppm]: 0.68 (t, 3H), 1.82–1.88 (m, 1H), 2.02–2.35 (m, 3H), 2.35 (s, 6H), 3.17 (d, 1H), 3.20 (d, 1H), 3.27 (t, 2H), 3.34–3.37 (m, 2H), 4.17 (br, 1H), 6.53 (d, 2H), 7.15–7.28 (m, 5H), 8.32 (d, 2H).

9c 1-[4-(3-Mercaptopropylamino)phenyl]-2-dimethylamino-2-benzyl-butan-1-one 6.4 g (0.014 mol) of 1-[4-(3-Iodopropylamino)phenyl]-2-dimethylamino-2-benzyl-butan-1-one are dissolved in 50 ml of dimethylacetamide. To the solution are added 2.28 g of potassium thioacetate and heated up to 50° C. After the reaction mixture is stirred at 50° C. for 15 min, it is poured into 150 ml of water and extracted with ethyl acetate. The organic phase is washed with water and saturated sodium chloride solution, and dried over MgSO$_4$. After distilling off the ethyl acetate, the residue is dissolved in 50 ml of ethanol and the solution is bubbled by nitrogen for 30 min. to remove oxygen. To the solution are added 7 ml of 2 N sodium hydroxide solution and stirred at 0° C. for 15 min. After the reaction mixture is neutralized by adding 2% hydrochloric acid solution, the resulting solution is poured into 100 ml of water and extracted with ethyl acetate. The organic phase is washed with water and saturated sodium chloride solution, and dried over MgSO$_4$. After distilling off the ethyl acetate, the residue is purified by means of column chromatography on silica gel with ethyl acetate-hexane (1:3) as an eluent, and an oily product is obtained. The structure is confirmed by the $^1$H-NMR spectrum (CDCl$_3$): δ [ppm]: 0.68 (t, 3H), 1.41 (t, 1H), 1.83–2.08 (m, 4H), 2.35 (s, 6H), 2.66 (q, 2H), 3.17 (d, 1H), 3.20 (d, 1H), 3.34 (br, 2H), 4.15 (br, 1H), 6.52 (d, 2H), 7.14–7.28 (m, 5H), 8.32 (d, 2H).

EXAMPLE 10

1-[4-(6-mercaptohexylthio)-phenyl]-2-methyl-2-morpholine-4-yl-propane-1-one 10.0 g (0.066 mol) of 1,6-hexanedithiol are added to a suspension of 3.6 g (0.026 mol) of potassium carbonate in 15 ml of dimethylacetamide. The suspension is heated to 85° C., and a solution of 3.6 g (0.013 mol) of 1-(4-chlorophenyl)-2-methyl-2-morpholin-4-yl-propan-1-one in 20 ml of dimethylacetamide is added dropwise over 20 min. After stirring for 18 h, the reaction mixture is cooled, diluted with ethyl acetate (60 ml), and filtered. The filtrate is washed with water (3×50 ml), dried over $MgSO_4$, and concentrated i.v. (85° C./5 mm Hg). The resulting oil is purified by flash chromatography on silica gel (hexane/ethyl acetate 85:15) to a pale yellow oil which crystallizes to a colorless solid upon standing. m.p. 61–64° C. The structure is confirmed by the $^1$H-NMR spectrum ($CDCl_3$): δ [ppm] 1.31 (s, 6H), 1.35 (t, SH), 1.4–1.8 (m, 8H), 2.53 (q, 2H), 2.57 (t, 4H), 3.00 (t, 2H), 3.69 (t, 4H), 7.24 (d, 2H), 8.50 (d, 2H).

EXAMPLE 11

1-(4-{2-[2-(2-Mercapto-ethoxy)-ethoxy]-ethylthio}-phenyl)-2-methyl-2-morpholin-4-yl-propan-1-one 10.0 ml (0.06 mol) of dimercaptoethylethyleneglycol are added to a suspension of 3.3 g (0.024 mol) of potassium carbonate in 20 ml of dimethylacetamide. The suspension is heated to 85° C., and a solution of 3.2 g (0.012 mol) of 1-(4-chlorophenyl)-2-methyl-2-morpholin-4-yl-propan-1-one in 10 ml of dimethylacetamide is added dropwise over 30 min. After stirring for 18 h, the reaction mixture is cooled, diluted with ethyl acetate (100 ml), extracted with water (3×50 ml) to remove the carbonate and dimethylacetamide, dried over $MgSO_4$, and concentrated under vacuum. The resulting yellow oil is purified by flash chromatography on silica gel (hexane/ethyl acetate 85:15) to yield a pale yellow oil. The structure is confirmed by the $^1$H-NMR spectrum ($CDCl_3$). δ [ppm] 1.31 (s, 6H), 1.60 (t, SH), 2.57 (t, 4H), 2.69 (q, 2H), 3.22 (t, 2H), 3.61–3.65 (m, 6H), 3.69 (t, 4H), 3.75 (t, 2H), 7.29 (d, 2H), 8.49 (d, 2H).

EXAMPLE 12

1-{4-[2-(2-Mercapto-ethylthio)-ethylthio]-phenyl}-2-methyl-2-morpholin-4-yl-propan-1-one 25.7 g (0.15 mol) of 2-mercaptoethylsulfide (purity 90%) are added to a suspension of 8.3 g (0.06 mol) of potassium carbonate in 50 ml of dimethylacetamide. A solution of 8.0 g (0.03 mol) 1-(4-chlorophenyl)-2-methyl-2-morpholin-4-yl-propan-1-one in 25 ml of dimethylacetamide is added dropwise at 85° C. over 60 min. After stirring for 5 h, the reaction mixture is cooled, diluted with ethyl acetate (100 ml), extracted with water (3×100 ml) to remove the carbonate and dimethylacetamide, dried over $MgSO_4$, and concentrated under vacuum. The resulting yellow liquid (stench) is purified by flash chromatography on silica gel (hexane/ethyl acetate 85:15) to yield a pale yellow oil. The structure is confirmed by the $^1$H-NMR spectrum ($CDCl_3$): δ [ppm] 1.31 (s, 6H), 1.750 (t, SH), 2.57 (t, 4H), 2.71–2.85 (m, 6H), 3.20 (t, 2H), 3.70 (t, 4), 7.31 (d, 2H), 8.51 (d, 2H).

EXAMPLE 13

1-[4-(10-mercaptodecanylthio)-phenyl]-2-methyl-2-morpholine-4-yl-propane-1-one 51.7 g (0.25 mol) of 1,10-decanedithiol are added to a suspension of 13.9 g (0.10 mol) of potassium carbonate in 50 ml of dimethylacetamide. The suspension is heated to 85° C., and a solution of 13.4 g (0.05 mol) of 1-(4-chlorophenyl)-2-methyl-2-morpholin-4-yl-propan-1-one in 25 ml of dimethylacetamide is added dropwise over 5 h. After stirring for 18 h, the solid is filtered off, the filtrate is poured into 30 ml of 2N HCl solution. The formed white precipitate is collected by filtration and then dissolved in methylene chloride and neutralized with 30 ml of 2N NaOH solution. After methylene chloride is distilled off, the residual crystals are further purified by recrystallization from chloroform-ethanol (20:80). The obtained product has a melting point of 87–90° C. The structure is confirmed by the $^1$H-NMR spectrum ($CDCl_3$): δ [ppm] 1.28–1.39 (m, 9H), 1.45 (m, 2H),1.31 (s, 6H), 1.64 (q, 4H), 1.69 (m, 2H), 2.52 (q, 2H), 2.56 (m, 4H), 2.99 (m, 2H), 3.71 (m, 4H), 7.26 (d, 2H), 8.49 (d, 2H).

EXAMPLE 14

1-[4-(4-Mercaptobutylthio)-phenyl]-2-methyl-2-morpholin-4-yl-propan-1-one 40 g (0.15 mol) of 1-(4-chlorophenyl)-2-methyl-2-morpholin-4-yl-propan-1-one and 109 g (0.89 mol) of 1,4-butanedithiol are dissolved in 300 ml of dimethylacetamide, and the solution is stirred at around 100° C. together with 41 g of potassium carbonate for 5 h. Then the solution is cooled to room temperature and poured into water. The crude product is extracted with ethyl acetate, washed with saturated sodium chloride solution, dried over $MgSO_4$, and concentrated. The residue is purified by column chromatography on silica gel with ethyl acetate -hexane (20:80) as an eluent. Melting point 98 ° C. The structure is confirmed by the $^1$H-NMR spectrum ($CDCl_3$): δ [ppm] 1.31 (s, 6H), 1.36 (t, 1H), 1.76–1.90 (m, 4H), 2.53–2.62 (m, 6H), 2.98–3.04 (m, 2H), 3.69 (t, 4H), 7.25 (d, 2H), 8.50 (d, 2H).

EXAMPLE 15

1-[4-(4-Mercaptomethyl-benzylthio)-phenyl]-2-methyl-2-morpholin-4-yl-propan-1-one 1.51 g (6.0 mmol) of 1-(4-fluorophenyl)-2-methyl-2-morpholin-4-yl-propan-1-one and 1.0 g (6.0 mmol) of 1,4-bis(mercaptobenzene) are dissolved in 12 ml of dry dimethylformamide, and 12 mmol of sodium hydride are added. The solution is stirred at room temperature for 2 h. Then the solution is poured into water. The crude product is extracted with methylene chloride, washed with water, dried over $MgSO_4$, and concentrated. The residue is purified by column chromatography on silica gel with methylene chloride as an eluent. The structure is confirmed by the $^1$H-NMR spectrum ($CDCl_3$): δ [ppm] 1.30 (s, 6H), 1.76 (t, 1H), 2.56 (t, 4H), 3.68 (t, 4H), 3.73 (d, 2H), 4.20 (s, 2H), 7.20–7.38 (m, 6H), 8.46 (d, 2H).

EXAMPLE 16

1-[4-(Bis-mercaptomethyl-trimethyl-benzylthio)-phenyl]-2-methyl-2-morpholin-4-yl-propan-1-one 0.67 g (2.7 mmol) of 1-(4-fluorophenyl)-2-methyl-2-morpholin-4-yl-propan-1-one and 3.44 g (13.3 mmol) of 1,3,5-tris(mercaptomethyl)-2,4,6-trimethylbenzene are dissolved in 70 ml of dry dimethylformamide, and 5.4 mmol of sodium hydride are added. The solution is stirred at room temperature for 2 h. Then the solution is poured into water. The crude product is extracted with methylene chloride, washed with water, dried over $MgSO_4$, and concentrated. The residue is purified by column chromatography on silica gel with methylene chloride as an eluent. The structure is confirmed by the $^1$H-NMR spectrum ($CDCl_3$): δ [ppm] 1.33

(s, 6H), 1.60 (t, 2H), 2.49 (s, 9H), 2.59 (t, 4H), 3.71 (t, 4H), 3.80 (d, 4H), 4.27 (s, 2H), 7.34 (d, 2H), 8.54 (d, 2H).

EXAMPLE 17

1-[4-(3-Mercapto-2-mercaptomethyl-2-methyl-propylthio)-phenyl]-2-methyl-2-morpholin-4-yl-propan-1-one 3.6 g (14.3 mmol) of 1-(4-fluorophenyl)-2-methyl-2-morpholin-4-yl-propan-1-one and 12 g (71.3 mmol) of 1,1,1-trismercaptomethylethane are dissolved in 70 ml of dry dimethylformamide, and 28.6 mmol of sodium hydride are added. The solution is stirred at room temperature for 2 h. Then the solution is poured into water. The crude product is extracted with methylene chloride, washed with water, dried over MgSO$_4$, and concentrated. The residue is purified by column chromatography on silica gel with methylene chloride as an eluent. The structure is confirmed by the $^1$H-NMR spectrum (CDCl$_3$): δ [ppm] 1.12 (s, 3H), 1.30 (t, 2H), 1.31 (s, 6H), 2.57 (t, 4H), 2.62–2.72 (m, 4H), 3.14 (s, 2H), 3.69 (t, 4H), 7.33 (d, 2H), 8.49 (d, 2H).

EXAMPLE 18

[4-(2-Methyl-2-morpholin-4-yl-propionyl)-phenylthio]-acetic acid 2,2-bis-mercaptoacetoxymethyl-butyl ester 1.26 g (5.0 mmol) of 1-(4-fluorophenyl)-2-methyl-2-morpholin-4-yl-propan-1-one and 7.0 ml (25.0 mmol) of trimethylolpropane tris(2-mercaptoacetate) are dissolved in 25 ml of dry dimethylformamide, and 10.0 mmol of sodium hydride are added. The solution is stirred at room temperature for 2 h. Then the solution is poured into water. The crude product is extracted with methylene chloride, washed with water, dried over MgSO$_4$, and concentrated. The residue is purified by column chromatography on silica gel with methylene chloride-methanol (100:1) as an eluent. The structure is confirmed by the $^1$H-NMR spectrum (CDCl$_3$): δ [ppm] 0.93 (t, 3H), 1.31 (s, 6H), 1.44 (q, 2H), 1.95–2.13 (m, 2H), 2.57 (t, 4H), 3.25–3.32 (m, 6H), 3.70 (t, 4H), 4.10–4.15 (m, 6H), 7.33 (d, 2H), 8.51 (d, 2H).

EXAMPLE 19

3-Mercapto-propionic acid 2-[4-(2-methyl-2-morpholin-4-yl-propionyl)-phenylthio]-ethyl ester 5.9 g (19.1 mmol) of 1-[4-(2-hydroxyethylthio)-phenyl]-2-methyl-2-morpholin-4-yl-propan-1-one, 4.2 ml (38.2 mmol) of ethyl thioglycolate, and 4.4 g (22.9 mmol) of p-toluenesulfonic acid monohydrate are mixed and stirred at 100° C. for 24 h. Then the solution is cooled to room temperature and neutralized with 1N NaOH. The crude product is extracted with ethyl acetate, washed with saturated sodium chloride solution, dried over MgSO$_4$, and concentrated. The residue is purified by column chromatography on silica gel with ethyl acetate -hexane (30:70) as an eluent. The structure is confirmed by the $^1$H-NMR spectrum (CDCl$_3$): δ [ppm] 1.31 (s, 6H), 1.99 (t, 1H), 2.57 (t, 4H), 3.22–3.30 (m, 4H), 3.70 (t, 4H), 4.36 (t, 2H), 7.34 (d, 2H), 8.51 (d, 2H).

EXAMPLE 20

Mercapto-acetic acid 2-[4-(2-methyl-2-morpholin-4-yl-propionyl)-phenylthio]-ethyl ester 70 g (0.266 mol) of 1-[4-(2-hydroxyethylthio)-phenyl]-2-methyl-2-morpholin-4-yl-propan-1-one, 39 ml (0.452 mol) of 3-mercaptopropionic acid, and 47 g (0.249 mol) of p-toluenesulfonic acid monohydrate are mixed and stirred at 140° C. for 4 h. Then the solution is cooled to room temperature and neutralized with 1N NaOH. The crude product is extracted with ethyl acetate, washed with saturated sodium chloride solution, dried over MgSO$_4$, and concentrated. The residue is purified by column chromatography on silica gel with ethyl acetate-hexane (30:70) as an eluent. The structure is confirmed by the $^1$H-NMR spectrum (CDCl$_3$): δ [ppm] 1.31 (s, 6H), 1.65 (t, 1H), 2.57 (t, 4H), 2.65 (t, 2H), 2.76 (dt, 2H), 3.26 (t, 2H), 3.70 (t, 4H), 4.33 (t, 2H), 7.33 (d, 2H), 8.51 (d, 2H).

EXAMPLE 21

2-Benzyl-2-dimethylamino-1-[4-(3-mercapto-propoxy)-3-methoxy-phenyl]-butan-1-one 21a 2-Benzyl-2-dimethylamino-1-[4-(3-hydroxy-propoxy)-3-methoxy-phenyl]-butan-1-one 0.40 mol of sodium hydride are suspended in 500 ml of dry dimethylacetamide and 72.3 ml (1.0 mol) of 1,3-propanediol are added dropwise at 0° C. Then 68.3 g (0.20 mol) of 2-benzyl-1-(3,4-dimethoxy-phenyl)-2-dimethylamino-butan-1-one in dimethylacetamide are added dropwise at 0° C. After the solution is stirred at 120° C. for 18 h, the solution is poured into water. The crude product is extracted with ethyl acetate, washed with water, dried over MgSO$_4$, and concentrated. The residue is purified by column chromatography on silica gel with ethyl acetate-hexane (40:60) as an eluent. The structure is confirmed by the $^1$H-NMR spectrum (CDCl$_3$): δ [ppm] 0.69 (t, 3H), 1.83–1.92 (m, 1H), 2.04–2.16 (m, 3H), 2.38 (s, 6H), 2.40–2.55 (bs, 1H), 3.18–3.23 (m, 2H), 3.88 (s, 3H), 3.89 (t, 2H), 4.27 (t, 2H), 6.84 (d, 1H), 7.15–7.28 (m, 5H), 7.93 (d, 1H), 8.20 (dd, 1H).

21b 2-Benzyl-1-[4-(3-bromo-propoxy)-3-methoxy-phenyl]-2-dimethylamino-butan-1-one 14.3 g (37.1 mmol) of 2-benzyl-2-dimethylamino-1-[4-(3-hydroxy-propoxy)-3-methoxy-phenyl]-butan-1-one are dissolved in 200 ml of methylene chloride, and 10.7 g (40.8 mmol) of triphenylphosphine and 13.5 g (40.8 mmol) of carbon tetrabromide are added at 0° C. successively. The solution is stirred at 0° C. for 0.5 h. Then the solution is concentrated to give the crude product, which is purified by column chromatography on silica gel with ethyl acetate-hexane (20:80) as an eluent. The structure is confirmed by the $^1$H-NMR spectrum (CDCl$_3$): δ [ppm] 0.69 (t, 3H), 1.83–1.92 (m, 1H), 2.03–2.13 (m, 1H), 2.38 (s, 6H), 2.38–2.45 (m, 2H), 3.17–3.25 (m, 2H), 3.64 (t, 2H), 3.88 (s, 3H), 4.22 (t, 2H), 6.86 (d, 1H), 7.15–7.28 (m, 5H), 7.93 (d, 1H), 8.20 (dd, 1H).

21c 2-Benzyl-2-dimethylamino-1-[4-(3-mercapto-propoxy)-3-methoxy-phenyl]-butan-1-one 9.26 g (20.7 mmol) of 2-benzyl-1-[4-(3-bromo-propoxy)-3-methoxy-phenyl]-2-dimethylamino-butan-1-one are dissolved in 100 ml of dimethylacetamide, and 2.60 g (22.8 mmol) of potassium thioacetate are added. The solution is stirred at 50° C. for 1 h. Then the solution is cooled to room temperature and poured into water. The crude product is extracted with ethyl acetate, washed with saturated sodium chloride solution, dried over MgSO$_4$, and concentrated to give the thioacetate. This product is dissolved in 100 ml of ethanol, and 11.4 ml of 2N NaOH are added dropwise. The reaction solution is stirred at room temperature for 20 min. Then the solution is poured into water. The crude product is extracted with ethyl acetate, washed with saturated sodium chloride solution, dried over MgSO$_4$, and concentrated. The residue is purified by column chromatography on silica gel with ethyl acetate-hexane (20:80) as an eluent. The structure is confirmed by the $^1$H-NMR spectrum (CDCl$_3$): δ [ppm]

0.69 (t, 3H), 1.45 (t, 1H), 1.82–1.92 (m, 1H), 2.01–2.10 (m, 1H), 2.10–2.19 (m, 2H), 2.38 (s, 6H), 2.76 (dt, 2H), 3.16–3.23 (m, 2H), 3.88 (s, 3H), 4.20 (t, 3H), 6.84 (d, 1H), 7.16–7.28 (m, 5H), 7.93 (d, 1H), 8.20 (dd, 1H).

EXAMPLE 22

2-(3-Mercaptomethyl-piperidin-1-yl)-2-methyl-1-(4-methylthio-phenyl)-propan-1-one 22a 2-Bromo-1-(4-methylthiophenyl)-2-methylpropan-1-one 149.2 g (0.77 mol) of 2-methyl-1-[4-(methylthio)-phenyl]-propan-1-one, prepared by acylating thioanisol (as is described in EP-A-3002), are dissolved in 770 ml of methylene chloride. 0.2 ml of chlorosulfonic acid and 123.0 g (0.77 mol) of bromine are added dropwise slowly to this solution, with cooling, at room temperature. After stirring overnight, the solution is concentrated and is then reacted further as described below.

22b 3-Dimethyl-2-methoxy-2-(4-methylthiophenyl) oxirane 47.6 g (0.88 mol) of sodium methoxide are dissolved in 180 ml of dry methanol, and 201.4 g (0.74 mol) of 2-bromo-1-[4-(methylthio)-phenyl]-2-methylpropan-1-one, dissolved in a mixture of 180 ml of dry methanol and 180 ml of chlorobenzene, are added dropwise to this solution at 20 ° C. The methanol is then distilled off and the chlorobenzene solution is concentrated. The liquid crude product is further purified by distillation at 90 ° C. and 0.15 mmHg.

22c 2-(3-Hydroxymethyl-piperidin-1-yl)-2-methyl-1-[4-(methylthio)-phenyl]-propan-1-one 25.0 g (0.22 mol) of 3-hydroxymethylpiperidine, 25.5 g (0.11 mol) of 3-dimethyl-2-methoxy-2-[4-(methylthio)-phenyl]oxirane and 50 ml of p-xylene are mixed and heated to reflux temperature. After 20 h, the solvent is distilled off. The residue is purified by column chromatography on silica gel with ethyl acetate-hexane (20:80) as eluent, and oily product is obtained. The structure is confirmed by the $^1$H-NMR spectrum (CDCl$_3$): δ [ppm] 1.01–1.20 (m, 2H), 1.29 (s, 3H), 1.31 (s, 3H), 1.52–1.79 (m, 4H), 2.10 (m, 1H), 2.25 (m, 1H), 2.52 (s, 3H), 2.69 (m, 1H), 2.90 (m, 1H), 3.48 (m, 2H), 7.20 (d, 2H), 8.51 (d, 2H).

22d 2-(3-Mercaptomethyl-piperidin-1-yl)-2-methyl-1-[4-(methylthio)-phenyl]-propan-1-one 10.2 g (0.33 mol) of 2-(3-hydroxymethyl-piperidin-1-yl)-2-methyl-1-[4-(methylthio)-phenyl]-propan-1-one and 10.5 g of triphenylphosphine are dissolved in 60 ml of methylene chloride. 13.3 g of carbon tetrabromide is dissolved in 15 ml of methylene chloride and is added dropwise to the above solution at 5 ° C. After stirring for 2 h, the resulting solution is concentrated to give a slurry. This material is purified by column chromatography on silica gel with ethyl acetate-hexane (50-50) as an eluent, and an oily product is obtained. The resulting material is used for the next reaction. 13.0 g of the above oily product is dissolved in 80 ml of dried dimethylacetamide and 4.95 g of potassium thioacetate is added. After stirring for 2.5 h at 50 ° C., the reaction mixture is poured into ice-water and extracted with ethyl acetate. The combined organic layer is washed with saturated sodium chloride solution and died over MgSO$_4$. The solvent is removed by evaporator and the crude oil is further purified by column chromatography on silica gel with ethyl acetate-hexane (10:90) as an eluent, and an oily product is obtained. The product is dissolved in 40 ml of ethanol and the solution is bubbled by nitrogen for 10 min. to remove oxygen. To the solution are added 10 ml of 2N sodium hydroxide solution and stirred at 0° C. for 1 h. After the reaction mixture is neutralized by adding 2N hydrochloric acid solution, the resulting solution is poured into 10 ml of water and extracted with ethyl acetate. The organic layer is washed with water and saturated sodium chloride solution, and dried over MgSO$_4$. After ethyl acetate is distilled off, the residue is purified by means of column chromatography on silica gel with ethyl acetate-hexane (5-95) as an eluent, and an oily product is obtained. The structure is confirmed by the $^1$H-NMR spectrum (CDCl$_3$): δ [ppm] 1.02 (m, 1H), 1.26 (t, 1H), 1.29 (s, 3H), 1.30 (s, 3H), 1.43–1.55 (m, 1H), 1.61–1.66 (m, 2H), 1.87 (m, 1H), 2.06 (m, 1H), 2.23 (m, 1H), 2.40 (t, 2H), 2.52 (s, 3H), 2.69 (m, 1H), 2.88 (d, 1H), 7.22 (d, 2H), 8.49 (d, 2H).

EXAMPLE 23

2-[4-(2-Mercapto-ethyl)-piperidin-1-yl]-2-methyl-1-[4-(methylthio)-phenyl]-propan-1-one 23a 2-[4-(2-Hydroxy-ethyl)-piperidin-1-yl]-2-methyl-1-[4-(methylthio)-phenyl]-propan-1-one 9.21 g (71.3 mmol) of 4-hydroxyethylpiperidine, 11.2 g (50.1 mmol) of 3-dimethyl-2-methoxy-2-[4-(methylthio)-phenyl]oxirane and 50 ml of p-xylene are mixed and heated to reflux temperature. After 20 h, the solvent is distilled off. The residue is purified by column chromatography on silica gel with ethyl acetate-hexane (30:70) as an eluent, and oily product is obtained. The structure is confirmed by the $^1$H-NMR spectrum (CDCl$_3$): δ [ppm] 1.16–1.26 (m, 3H), 1.28 (S, 6H), 1.43 (m, 1H), 1.52 (q, 2H), 1.66 (d, 2H), 2.55 (t, 2H), 2.52 (s, 3H), 2.78 (d, 2H), 3.68 (t, 2H).

23b 2-[4-(2-Mercapto-ethyl)-piperidin-1-yl]-2-methyl-1-[4-(methylthio)-phenyl]-propan-1-one 9.81 g (30.5 mmol) of 2-[4-(2-hydroxy-ethyl)-piperidin-1-yl]-2-methyl-1-[4-(methylthio)-phenyl]-propan-1-one and 8.0 g of triphenylphosphine are dissolved in 100 ml of methylene chloride. 10.1 g of carbon tetrabromide is dissolved in 50 ml of methylene chloride and is added dropwise to the above solution at 5 ° C. After stirring for 1 h, the resulting solution is concentrated to give a slurry, this material is purified by column chromatography on silica gel with ethyl acetate-hexane (10:90) as an eluent, and an oily product is obtained. The resulting material is used for the next reaction. 13.0 g of the above oily product are dissolved in 100 ml of dried dimethylacetamide and 4.56 g of potassium thioacetate are added. After stirring for 2.5 h at 50° C., the reaction mixture is poured into ice-water and extracted with ethyl acetate. The combined organic layers are washed with saturated sodium chloride solution and dried over MgSO$_4$. The solvent is removed by evaporator and the crude oil is further purified by column chromatography on silica gel with ethyl acetate-hexane (10:90) as an eluent, and an oily product is obtained. The product is dissolved in 40 ml of ethanol and the solution is bubbled by nitrogen for 10 min. to remove oxygen. To the solution are added 10 ml of 2N sodium hydroxide solution and stirred at 0° C. for 1 h. After the reaction mixture is neutralized by adding 2N hydrochloric acid solution, the resulting solution is poured into 10 ml of water and extracted with ethyl acetate. The organic layer is washed with water and saturated sodium chloride solution, and dried over MgSO$_4$. After ethyl acetate is distilled off, the residue is purified by means of column chromatography on silica gel with ethyl acetate-hexane (5-95) as an eluent, and an oily product is obtained. The structure is confirmed by the $^1$H-NMR spectrum (CDCl$_3$): δ [ppm] 1.16 (m, 2H), 1.28 (s, 6H), 1.31 (t, 1H), 1.42 (m, 1H), 1.56 (q, 2H), 1.63 (d, 2H), 2.24 (t, 2H), 2.52 (s, 3H), 2.53 (m, 2H), 2.79 (d, 2H), 7.21 (d, 2H), 8.53 (d, 2H).

EXAMPLE 24

1-[4-(3-Mercapto-propoxy)-phenyl]-2-methyl-2-morpholin-4-yl-propan-1-one 24a 1-[4-(3-hydroxy-propoxy)-phenyl]-2-methyl-2-morpholin-4-yl-propan-1-one 24.9 g (0.33 mol) of 1,3-propanol are dissolved in 50 ml of dry dimethylacetamide, and 6.4 g of sodium hydride (ca 60% dispersed in oil) are added by portions at such rate as to maintain a temperature of 5° C. 20.0 g ( 0.08 mol) of 1-(4-fluorophenyl)-2-methyl-2-morpholin-4-yl-propan-1-one in 50 ml of dry dimethylacetamide are added dropwise over 8 hr. The suspension is stirred for additional 17 h, then the resulting reaction mixture is poured into ice-water. The crude product is extracted with ethyl acetate, washed with saturated NaCl solution and dried over $MgSO_4$. After ethyl acetate is distilled off, the residue is purified by means of column chromatography on silica gel with ethyl acetate-hexane (40:60) as an eluent, and an oily product is obtained. The structure is confirmed by the $^1$H-NMR spectrum ($CDCl_3$): δ [ppm] 1.31 (s, 6H), 1.85 (s, 1H), 1.87 (m, 2H), 2.57 (m, 4H), 3.69 (m, 4H), 3.87 (t, 2H), 4.19 (m, 2H), 6.90 (d, 2H), 8.59 (d, 2H).

24b 1-[4-(3-Iodo-propoxy)-phenyl]-2-methyl-2-morpholin-4-yl-propan-1-one 16.2 g (53 mmol) of 1-[4-(3-hydroxy-propoxy)-phenyl]-2-methyl-2-morpholin-4-yl-propan-1-one, 8.97 g (132 mmol) of imidazole and 34.5 g (132 mmol) of triphenyl phosphine are dissolved in 150 ml of methylene chloride. To the solution are added 27.0 g (106 mmol) of iodine and stirred at room temperature for 1 hour. 100 ml of methylene chlorideare added to the reaction mixture and washed with sodium sulfite aqueous solution and water, and dried over $MgSO_4$. After methylene chloride is distilled off, the residue is purified by means of column chromatography on silica gel with ethyl acetate-hexane (1:3) as an eluent, and an oily product is obtained. The structure is confirmed by the $^1$H-NMR spectrum ($CDCl_3$): δ [ppm] 1.31 (s, 6H), 2.30 (m, 2H), 2.57 (m, 4H), 3.38 (t, 2H), 3.69 (m, 4H), 4.11 (t, 2H), 6.91 (d, 2H), 8.60 (d, 2H).

24c 1-[4-(3-Mercapto-propoxy)-phenyl]-2-methyl-2-morpholin-4-yl-propan-1-one 12.5 g (29.9 mmol) of 1-[4-(4-iodo-propoxy)-phenyl]-2-methyl-2-morpholin-4-yl-propan-1-one are dissolved in 80 ml of dimethylacetamide. To the solution are added 4.47 g of potassium thioacetate and the mixture is heated up to 50° C. After the reaction mixture is stirred at 50 degree for 4 hours, it is poured to 100 ml of water and extracted with ethyl acetate. The organic phase is washed with water and saturated sodium chloride solution, dried over $MgSO_4$, and concentrated to leave an oily product. 3.71 g of the resulting intermediate are dissolved in 100 ml of ethanol and the solution is bubbled by nitrogen for 30 min. to remove oxygen. To the solution are added 10 ml of 2 N sodium hydroxide solution and it is stirred at 0° C. for 30 min. After the reaction mixture is neutralized by adding 2 N hydrochloric acid solution, the solution is concentrated and extracted with ethyl acetate. The organic phase is washed with water and saturated sodium chloride solution, and dried over $MgSO_4$. After ethyl acetate is distilled off, the residue is purified by means of column chromatography on silica gel with ethyl acetate-hexane (20:80) as an eluent, and an oily product is obtained. The structure is confirmed by the $^1$H-NMR spectrum ($CDCl_3$): δ [ppm] 1.31 (s, 6H), 1.39 (t, 1H), 2.11 (m, 2H), 2.57 (m, 4H), 2.57 (m, 4H), 2.75 (q, 2H), 3.69 (m, 4H), 4.15 (m, 2H), 6.91 (d, 2H), 8.58 (d, 2H).

EXAMPLE 25

1-[4-(3-Mercapto-propylthio)-phenyl]-2-(3-mercaptomethyl-piperidin-1-yl)-2-methyl-propan-1-one 25a 1-(4-Chloro-phenyl)-2-(3-hydroxymethyl-piperidin-1-yl)-2-methyl-propan-1-one 24.3 g (0.22 mol) of 3-hydroxymethylpiperidine, 23.2 g (0.11 mol) of 3-dimethyl-2-methoxy-2-[4-chloro-phenyl] oxirane and 50 ml of p-xylene are mixed and heated to reflux temperature. After 20 h, the mixture is washed with water, saturated sodium chloride solution successively and then dried over $MgSO_4$. After distilling off the solvent, the crude oil is purified by column chromatography on silica gel with ethyl acetate-hexane (30:80) as an eluent, and an oily product is obtained. The structure is confirmed by the $^1$H-NMR spectrum ($CDCl_3$): δ [ppm] 1.03 (m, 1H), 1.28 (m, 4H), 1.30 (s, 3H), 1.50 (m, 1H), 1.63 (m, 1H), 1.74 (m, 2H), 2.04 (t, 1H), 2.24 (m, 1H), 2.68 (d, 1H), 2.88 (d, 1H), 3.46 (m, 2H), 7.34 (d, 2H), 8.51 (d, 2H).

25b 1-[4-(3-Hydroxy-propylthio)-phenyl]-2-(3-hydroxymethyl-piperidin-1-yl)-2-methyl-propan-1-one 22.4 g of 1-(4-chloro-phenyl)-2-(3-hydroxymethyl-piperidin-1-yl)-2-methyl-propan-1-one, 8.39 g of 3-mercaptopropanol and 21.0 g of potassium carbonate are mixed in 75 ml of dried dimethylacetamide. After stirring for 18 h at 80° C., the mixture is filtered to remove solids and poured into ice-water. The crude product is extracted with ethyl acetate, washed with saturated NaCl solution and dried over $MgSO_4$. After ethyl acetate is distilled off, the residue is purified by means of column chromatography on silica gel with ethyl acetate-hexane (40:60) as an eluent, and an oily product is obtained. The structure is confirmed by the $^1$H-NMR spectrum ($CDCl_3$): δ [ppm] 1.02 (m, 1H), 1.29 (s, 3H), 1.30 (s, 3H), 1.52–1.77 (m, 6H), 1.95 (m, 2H), 2.05 (t, 1H), 2.27 (t, 1H), 2.67 (d, 1H), 2.86 (d, 1H), 3.12 (t, 2H), 3.44 (m, 2H), 3.78 (m, 2H), 7.28 (d, 2H), 8.48 (d, 2H).

25c Thioacetic acid S-(1-{2-[4-(3-acetylthio-propylthio)-phenyl]-1,1-dimethyl-2-oxo-ethyl}-piperidin-3-ylmethyl) ester 10.2 g (32.0 mmol) of 1-[4-(3-hydroxy-propylthio)-phenyl]-2-(3-hydroxymethyl-piperidin-1-yl)-2-methyl-propan-1-one and 20.1 g (76.8 mmol) of triphenylphosphine are dissolved in 100 ml of methylene chloride. 25.5 g of carbon tetrabromide are dissolved in 30 ml of methylene chloride and are added dropwise to the above solution at 5° C. After stirring for 1.5 h, the resulting solution is concentrated to give a slurry, which is purified by column chromatography on silica gel with ethyl acetate-hexane (5:95) as an eluent, and an oily product is obtained. The resulting material is used for the next reaction. 11.1 g of the above oily product are dissolved in 90 ml of dried dimethylacetamide and 6.92 g of potassium thioacetate are added by portions. After stirring for 1 h at 50 ° C., the reaction mixture is poured into ice-water and extracted with ethyl acetate. The combined organic layers are washed with saturated sodium chloride solution and dried over $MgSO_4$. The solvent is removed by evaporator and the crude oil is further purified by column chromatography on silica gel with ethyl acetate-hexane (10:90) as an eluent, and an oily product is obtained. The structure is confirmed by the $^1$H-NMR spectrum ($CDCl_3$): δ [ppm] 1.06 (m, 1H), 1.27 (s, 3H), 1.29 (s, 3H), 1.47 (m, 1H), 1.59 (m, 1H), 1.75 (m, 2H), 1.98 (m, 3H), 2.23 (m, 1H), 2.30 (s, 3H), 2.35 (s, 3H), 2.62 (d, 1H), 2.79 (m, 3H), 3.04 (m, 4H), 7.25 (d, 2H), 8.44 (d, 2H).

25d 1-[4-(3-Mercapto-propylthio)-phenyl]-2-(3-mercaptomethyl-piperidin-1-yl)-2-methyl-propan-1-one 6.97 g (14.9 mmol) of the product of example 25c are dissolved in a mixture of 60 ml of ethanol and 10 ml of dimethylacetamide and the resulting solution is bubbled by nitrogen for 10 min. to remove oxygen. To the solution are added 15 ml of 2N sodium hydroxide solution and stirred at 0° C. for 15 min. After the reaction mixture is neutralized by adding 2N hydrochloric acid solution, the ethanol is removed by distillation. The crude product is extracted with ethyl acetate and the combined organic layers are washed with water and saturated sodium chloride solution, and dried over $MgSO_4$. After ethyl acetate is distilled off, the residue is purified by means of column chromatography on silica gel with ethyl acetate-hexane (5:95) as an eluent, and an oily product is obtained. The structure is confirmed by the $^1$H-NMR spectrum ($CDCl_3$): δ [ppm] 1.02 (m, 1H), 1.21 (m, 1H), 1.28 (s, 3H), 1.30 (s, 3H), 1.39 (t, 1H), 1.48 (m, 1H), 1.64 (m, 2H), 1.88 (m, 1H), 2.02 (m, 3H), 2.23 (m, 1H), 2.40 (t, 2H), 2.68 (m, 3H), 2.90 (d, 1H), 3.11 (t, 2H), 7.26 (2H, d), 8.48 (2H, d).

EXAMPLE 26

1-[4'-(3-Mercapto-propylthio)-biphenyl-4-yl]-2-methyl-2-morpholin-4-yl-propan-1-one 3.5 g (9.0 mmol) of 1-(4'-Bromo-biphenyl-4-yl)-2-methyl-2-morpholin-4-yl-propan-1-one (prepared by the method described in EP-A-3002) and 5.4 ml (54 mmol) of 1,3-propanedithiol are dissolved in 50 ml of dimethylacetamide, and the solution is stirred at around 140° C. together with 2.5 g of potassium carbonate for 2.5 h. Then the solution is cooled to room temperature and poured into water. The crude product is extracted with methylene chloride, washed with saturated sodium chloride solution, dried over $MgSO_4$, and concentrated. The residue is purified by column chromatography on silica gel with ethyl acetate-hexane (10:90) as an eluent. The structure is confirmed by the $^1$H-NMR spectrum ($CDCl_3$): δ [ppm] 1.35 (s, 6H), 1.38 ( t, 1H), 1.98 (tt, 2H), 2.61 (t, 4H), 2.69 (dt, 2H), 3.11 (t, 2H), 3.72 (t, 4H), 7.42 (d, 2H), 7.51 (d, 2H), 7.62 (d, 2H), 8.63 (d, 2H).

EXAMPLE 27

2-Benzyl-2-dimethylamino-1-[4'-(3-mercapto-propylthio)-biphenyl-4-yl]-butan-1-one 9.2 mmol of sodium hydride are suspended in 40 ml of dry dimethylformamide and 2.3 ml (23 mmol) of 1,3-propanedithiol are added dropwise. Then 2.0 g (4.6 mmol) of 2-benzyl-1-(4'-bromo-biphenyl-4-yl)-2-dimethylamino-butan-1-one (prepared by the method described in U.S. Pat. No. 5,534,629) in 60 ml of dimethylformamide are added dropwise. After stirring the solution at 100° C. for 2 h, the solution is poured into water. The crude product is extracted with methylene chloride, washed with water, dried over $MgSO_4$, and concentrated. The residue is purified by column chromatography on silica gel with ethyl acetate-hexane (10:90) as an eluent. The structure of the product is confirmed by the $^1$H-NMR spectrum ($CDCl_3$): δ [ppm] 0.72 (t, 3H), 1.37 (t, 1H), 1.84–2.01 (m, 3H), 2.09 (dq, 1H), 2.40 (s, 6H), 2.68 (dt, 2H), 3.10 (t, 2H), 3.23 (s, 2H), 7.15–7.29 (m, 5H), 7.41 (d, 2H), 7.55–7.62 (m, 4H), 8.41 (d, 2H).

EXAMPLE 28

A photocurable formulation is prepared by mixing the following components:

10.0 g of dipentaerythritol monohydroxypentaacrylate, ®SR 399, Sartomer Co., Berkshire, GB 15.0 g of tripropylene glycol diacrylate, Sartomer Co., Berkshire, GB 15.0 g of N-vinylpyrrolidone, Fluka 10.0 g of trimethylolpropane triacrylate, Degussa 50.0 g of urethane acrylate ®Actylan AJ20, Société Nationale des Poudres et Explosifs 0.3 g of levelling assistant ®Byk 300, Byk-Mallinckrodt Portions of this composition are mixed with 2%, based on the overall quantity of the formulation, of the photoinitiator of example 1. All operations are carried out under red light. The samples to which the photoinitiator has been added are are applied to a 300 μm aluminium foil. The thickness of the dry film is 60 μm. To this film there is applied a 76 μm thick polyester film, over which a standardized test negative having 21 steps of different optical density (Stouffer wedge) is placed. The sample is covered with a second UV-transparent film and compressed on a metal plate by means of vacuum. Exposure is carried out in a first test series for 5 seconds, in a second series for 10 seconds and in a third series for 20 seconds, using a 4 kW xenon lamp at a distance of 30 cm. Following exposure, the cover films and the mask are removed and the exposed film is developed in ethanol for 10 seconds at 23° C. in an ultrasound bath. Drying is carried out at 40° C. in a convection oven for 5 minutes. The sensitivity of the initiator system used is characterized by indicating the last wedge step which was reproduced (i.e. polymerized) without tack. The higher the number of steps, the more sensitive the system tested. A further test is carried out, employing the same formulation, but adding additionally 0.2% of a mixture of 2-isopropylthioxanthone and 4-isopropylthioxanthone (®Quantacure ITX, International Biosynthetics). The results are summarized in table 1.

TABLE 1

| Compound from Example | Number of steps reproduced after exposure times of | | |
|---|---|---|---|
| | 5 s | 10 s | 20 s |
| 1 | 8 | 8 | 13 |
| 1 + ITX | 12 | 13 | 14 |

EXAMPLE 29

A photocurable formulation is prepared by mixing the following components:

| | |
|---|---|
| 150.30 g of ®Scripset 540 (30% solution of polystyrol-maleic acid anhydride-copolymer in aceton); Monsanto | 45.1 g |
| 48.30 g of trimethylolpropane triacrylate | 48.3 g |
| 6.60 g of polyethylenglycole diacrylate | 6.6 g |
| | 100.0 g solid contents |

Portions of this composition are mixed with 2%, based on the overall quantity of the formulation, of the photoinitiator of example. 1. All operations are carried out under red light. The samples to which the photoinitiator has been added are applied to a 200 μm aluminium foil (10×15 cm). The solvent is evaporated through warming to 60° C. for 15 minutes in a convection oven. On the thus prepared film there is applied a 76 μm thick polyester film, over which a standardized test negative having 21 steps of different optical density (Stouffer wedge) is placed. The sample is covered with a second UV-transparent film and compressed on a metal plate by means of vacuum. Exposure is carried out for 40 seconds, using a MO61/5 KW lamp at a distance of 30 cm. Following exposure, the cover films and the mask are removed and the exposed film is developed in a 0.85% aqueous $Na_2CO_3$ solution for 120 seconds in an ultrasound bath. Drying is carried out at 40° C. in a convection oven for 5 minutes. The sensitivity of the initiator system used is characterized by indicating the last wedge step which was reproduced (i.e. polymerized) without tack. The higher the number of steps, the more sensitive the system tested. With the photoinitiator of example 1 a step number of 11 is achieved in the above described test.

EXAMPLE 30

A photocurable composition is prepared by mixing the following components:

| | |
|---|---|
| 37.64 g | of ®Sartomer SR 444, pentaerythritol triacrylate, (Sartomer Company, Westchester) |
| 10.76 g | of ®Cymel 301, hexamethoxymethylmelamine (American Cyanamid, U.S.A.) |
| 47.30 g | of ®Carboset 525, thermoplastic polyacrylate containing carboxyl groups (B. F. Goodrich) |
| 4.30 g | of polyvinylpyrrolidone PVP (GAF, U.S.A.) |
| 100.00 g | of this composition are mixed with |
| 319.00 g | of methylene chloride and |
| 30.00 g | of methanol. |

Samples of this composition are mixed with 2% of the photoinitiator of example 1, based on the solids content, by stirring at room temperature for one hour. All operations are carried out under red light. The samples to which initiator has been added are applied to a 300 μm aluminium foil (10×15 cm). The solvent is removed by first drying at room temperature for 5 minutes and then heating at 60° C. for 15 minutes in a convection oven, to give a dry film thickness of 35 μm. A 76 μm thick polyester film is placed on the liquid film, and a standardized test negative with 21 steps of different optical density (Stouffer wedge) is placed over this. The sample is covered with a second UV-transparent film and is compressed on a metal plate by means of vacuum. The sample is then exposed for 10 seconds in the first test series, 20 seconds in a second series and 40 seconds in a third series using a 4 kW xenon lamp at a distance of 30 cm. After exposure, the cover films and the mask are removed and the exposed film is developed for 240 seconds with 1% strength aqueous sodium carbonate solution in an ultrasound bath and then dried at 60° C. in a convection oven for 15 minutes. The sensitivity of the initiator system used is characterized by indicating the last wedge step reproduced without tack. The higher the number of steps, the more sensitive the system. A further test series is provided, employing the same formulation, but adding additionally 0.2% of a mixture of 2-isopropylthioxanthone and 4-isopropylthioxanthone (®Quantacure ITX, International Biosynthetics). The results are summarized in table 2.

TABLE 2

| Compound from Example | Number of steps reproduoed after exposure for | | |
|---|---|---|---|
| | 10 s | 20 s | 40 s |
| 1 | 10 | 13 | 15 |
| 1 + ITX | 14 | 15 | 17 |

EXAMPLE 31

A photocurable formulation for sensitivity tests is prepared by mixing the following components:

- 200 parts by weight of acyrylated acrylcopolymer ACA200M, provided by Daicel Industries, Ltd.
- 15 parts by weight of dipentaerythritol hexaacrylate (DPHA), provided by UCB Chemicals
- 15 parts by weight of the photoinitiator to be tested All operations are carried out under yellow light. The formulations are applied to a aluminum plate. The solvent is removed by heating at 80° C. for 15 minutes in a convection oven. The thickness of the dry film is 25 μm. To this coating there is applied an acetate film, over which a standardized test negative with 21 steps of different optical density (Stouffer wedge) is placed. The sample is covered with a second UV-transparent film and compressed on a metal plate by means of vacuum. Exposure is carried out in a first test series for 10 seconds, in a second series for 20 seconds and in a third series for 40 seconds, using a 3 kW metal halide lamp at a distance of 60 cm. Following exposure, the cover films and the mask are removed and the exposed film is developed in 1% sodium carbonate aqueous solution for 240 sec. at 30° C. in an ultrasound bath. The sensitivity of the initiator system used is characterized by indicating the last wedge step which was reproduced (i.e. polymerized) without tack. The higher the number of steps, the more sensitive the system tested. A further test series is provided, adding a mixture of 2-isopropylthioxanthone and 4-isopropylthioxanthone (®Quantacure ITX, International Biosynthetics) to the above described formulation:

- 200 parts by weight of acyrylated acrylcopolymer ACA200M, provided by Daicel Industries, Ltd.
- 15 parts by weight of dipentaerythritol hexaacrylate (DPHA), provided by UCB Chemicals
- 15 parts by weight of the photoinitiator to be tested
- 1 part by weight of ®Quantacure ITX, provided by International Biosynthetics The test results are summarized in table 3.

TABLE 3

| Photoinitiator of example | Number of steps reproduced after exposure time of | | |
|---|---|---|---|
| | 10 sec. | 20 sec. | 40 sec. |
| 11 | 8 | 11 | 13 |
| 11 + ITX | 10 | 13 | 15 |
| 12 | 9 | 11 | 13 |
| 12 + ITX | 10 | 12 | 14 |
| 21 | 9 | 11 | 13 |
| 21 + ITX | 10 | 12 | 14 |
| A | 7 | 10 | 12 |
| A + ITX | 10 | 12 | 14 |
| B | 4 | 6 | 8 |
| B + ITX | 7 | 9 | 11 |

Compound A:

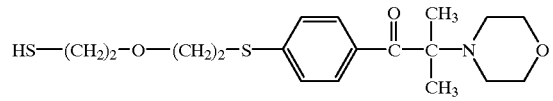

Compound B:

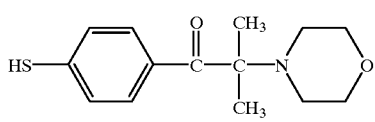

What is claimed is:
1. Compounds of the formula I, II, III or IV

(I)
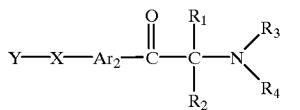

(II)
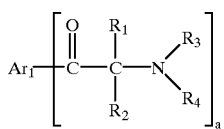

(III)
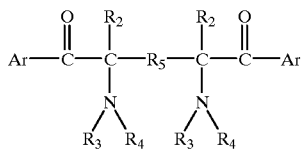

(IV)
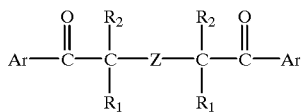

wherein a is an integer 1, 2 or 4;

Ar is a phenyl, biphenyl or benzoylphenyl group, which is unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —OR$_7$, —SH, —SR$_8$, —SOR$_8$, —SO$_2$R$_8$, —CN, —SO$_2$NH$_2$, —SO$_2$NH($C_1$–$C_4$alkyl), —SO$_2$—N($C_1$–$C_4$alkyl)$_2$, —NR$_9$R$_{10}$, —NHCOR$_9$, or by a group of the formula V, (V)
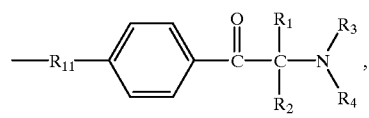

or Ar is a group of the formula VI or VII (VI)
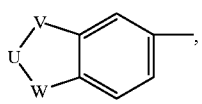

(VII)
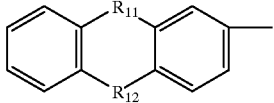

Ar$_1$ if a is 1 has the same meanings as Ar;
if a is 2, Ar$_1$ is a divalent aromatic radical of the formula VIII or VIIIa (VIII)
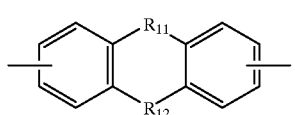

(VIIIa)
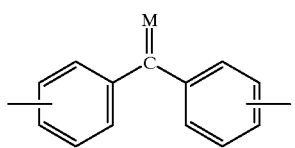

if a is 4, Ar$_1$ is a tetravalent aromatic radical of the formula VIIIb (VIIIb)
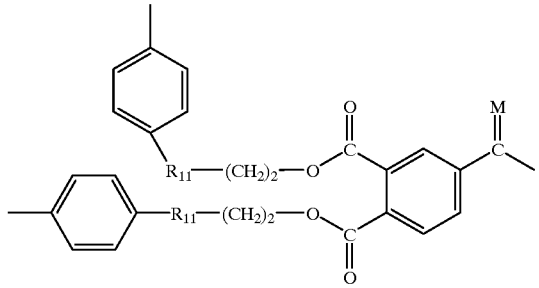

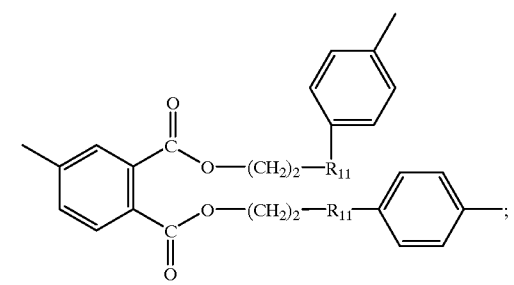

Ar$_2$ is

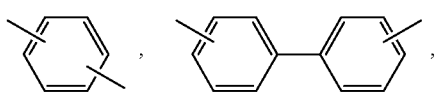

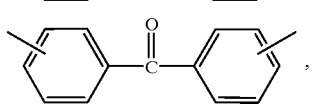

these groups are unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO ($C_1$–$C_4$alkyl), —$OR_7$, —SH, —$SR_8$, —$SOR_8$, —$SO_2R_8$, —CN, —$SO_2NH_2$, —$SO_2NH(C_1$–$C_4$alkyl), —$SO_2$—N($C_1$–$C_4$alkyl)$_2$, —$NR_9R_{10}$, —$NHCOR_9$, or by a group of the formula V as defined above, or $Ar_2$ is a group of the formula VIa or VIIa

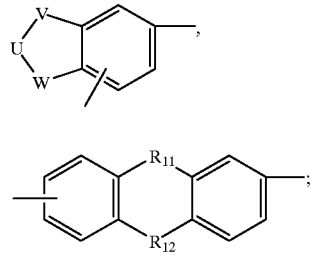

(VIa)

(VIIa)

X is a direct bond, —O—, —S— or —N($R_6$)—;

Y is hydrogen, $C_1$–$C_{12}$alkyl, which is unsubstituted or substituted by 1 to 5 OH, $OR_6$, $COOR_6$, SH, $N(R_6)_2$ or halogen or substituted 1 to 5 times by a group of the formula Ia

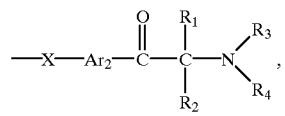

(Ia)

or Y is $C_2$–$C_{20}$alkyl, which is interrupted by 1 to 9 —O—, —N($R_6$)—, —S—, —SS—, —X—C(=O)—, —X—C(=S)—, —C(=O)—X—, —X—C(=O)—X—, —C(=S)—X—,

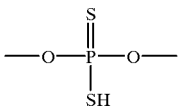

wherein the interrupted $C_2$–$C_{20}$alkyl can further be substituted by 1 to 5 SH, or Y is benzyl which is unsubstituted or substituted once or twice by —$CH_2SH$ and said benzyl may further be substituted by $C_1$–$C_4$alkyl, or Y is Ar (as defined above), or a group

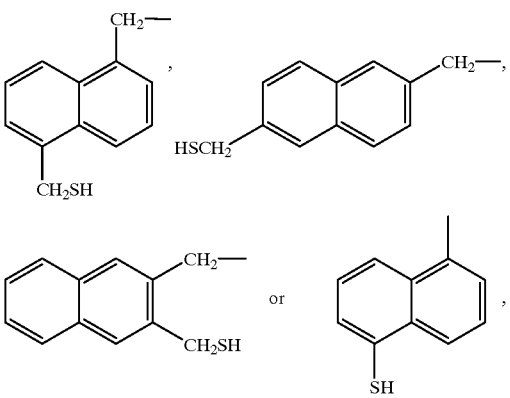

or Y is a heterocyclic 5–7 membered aliphatic or aromatic ring, comprising 1 to 4 N, O or/and S-atoms, or Y is a 8–12 membered bicyclic aliphatic or aromatic ring system, comprising 1 to 6 N, O or/and S-atoms, which mono- or bicyclic rings can further be substituted by SH or 1–5 times by a group of the formula Ia, or Y is a group

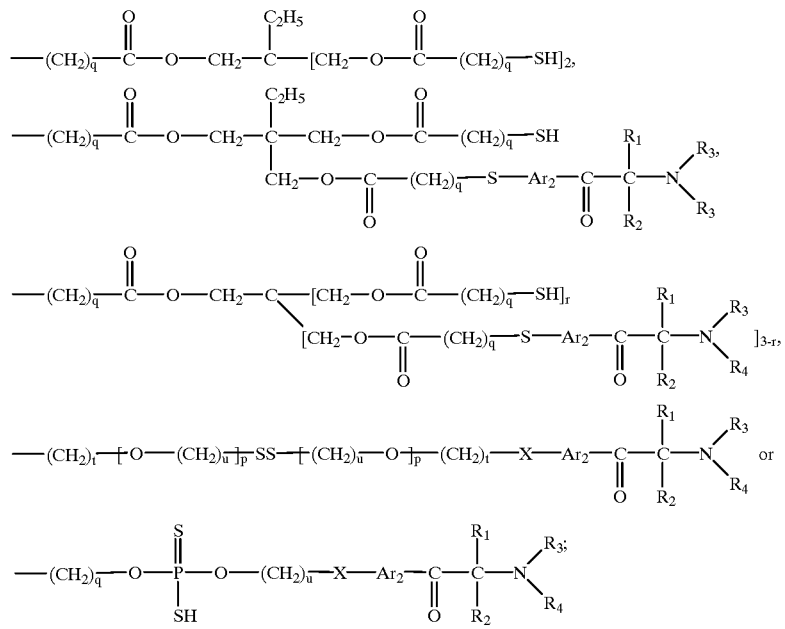

q is 1 or 2;

r is 1, 2 or 3;

p is 0 or 1;

t is 1 to 6;

u is 2 or 3;

$R_1$ and $R_2$ independently of one another are $C_1$–$C_8$alkyl, which is unsubstituted or substituted by OH, $C_1$–$C_4$alkoxy, SH, CN, —COO($C_1$–$C_8$alkyl), ($C_1$–$C_4$alkyl)—COO— or —N($R_3$)($R_4$), or $R_1$ and $R_2$ independently of one another are $C_3$–$C_6$alkenyl, phenyl, chlorophenyl, $R_7$—O-phenyl, $R_8$—S-phenyl or phenyl-$C_1$–$C_3$-alkyl, wherein said $C_3$–$C_6$alkenyl, phenyl, chlorophenyl, $R_7$—O-phenyl, $R_8$—S-phenyl or phenyl-$C_2$–$C_3$-alkyl are unsubstituted or substituted by 1 to 5 SH, or $R_1$ and $R_2$ together are unbranched or branched $C_2$–$C_9$alkylene, $C_3$–$C_9$oxaalkylene or $C_3$–$C_9$azaalkylene, wherein said $C_2$–$C_9$alkylene, $C_3$–$C_9$oxaalkylene or $C_3$–$C_9$azaalkylene are unsubstituted or substituted by 1 to 5 SH or $R_1$ and $R_2$ independently of one another are a radical of the formula IX or X

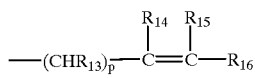
(IX)

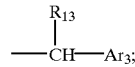
(X)

$R_3$ is hydrogen, $C_1$–$C_{12}$alkyl, $C_2$–$C_4$alkyl, which is substituted by OH, SH, $C_1$–$C_4$alkoxy, CN or —COO($C_1$–$C_4$alkyl), or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl, $C_2$–$C_4$alkyl, which is substituted by OH, SH, $C_1$–$C_4$alkoxy, CN or —COO($C_1$–$C_4$alkyl), or $R_4$ is $C_3$–$C_5$alkenyl, $C_5$–$C_{12}$-cycloalkyl, phenyl-$C_1$–$C_3$alkyl, unsubstituted phenyl or phenyl, which is substituted by halogen, $C_1$–$C_{12}$alkyl, $C_1$–$C_4$alkoxy or —COO($C_1$–$C_4$alkyl);

or $R_4$ together with $R_2$ is $C_1$–$C_7$alkylene, phenyl-$C_1$–$C_4$alkylene, o-xylylene, 2-butenylene or $C_2$–$C_3$oxaalkylene or $C_2$–$C_3$azaalkylene;

or $R_3$ and $R_4$ together are $C_3$–$C_7$alkylene, which can be interrupted by —O—, —S—, —CO— or —N($R_6$)— and which $C_3$–$C_7$alkylene can be substituted by OH, $C_1$–$C_4$alkoxy or —COO($C_1$–$C_4$alkyl);

$R_5$ is $C_1$–$C_6$alkylene, xylylene, cyclohexylene, wherein said $C_1$–$C_6$alkylene, xylylene, cyclohexylene are unsubstituted or substituted by 1 to 5 SH, or $R_5$ is a direct bond;

$R_6$ is hydrogen, unsubstituted or OH—, SH— or HS—($CH_2$)$_q$—COO-substituted $C_1$–$C_{12}$alkyl, $C_2$–$C_{12}$alkyl, which is interrupted by —O—, —NH— or —S—, or $R_6$ is $C_3$–$C_5$alkenyl, phenyl-$C_1$–$C_3$alkyl, $CH_2CH_2CN$, unsubstituted or OH- or SH-substituted $C_1$–$C_4$alkyl-CO—$CH_2CH_2$—, unsubstituted or OH- or SH-substituted $C_2$–$C_8$alkanoyl or $R_6$ is benzoyl;

Z is a divalent radical of the formula

—N($R_{17}$)— or —N($R_{17}$)—$R_{18}$—N($R_{17}$)—;

U is unbranched or branched $C_1$–$C_7$alkylene;

V and W independently of one another are a direct bond, —O—, —S— or —N($R_6$)—, provided that V and W are not both a direct bond simultaneously;

M is O, S or N($R_6$);

$R_7$ is hydrogen, $C_1$–$C_{12}$alkyl, $C_3$–$C_{12}$-alkenyl, cyclohexyl, hydroxycyclohexyl, or $R_7$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —OOCR$_{19}$, —COOH, —COO($C_1$–$C_8$alkyl), —CONH($C_1$–$C_4$alkyl), —CON($C_1$–$C_4$alkyl)$_2$,

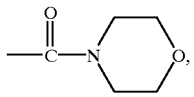

—CO($C_1$–$C_4$alkyl) or

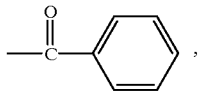

or $R_7$ is 2,3-epoxypropyl, —(CH$_2$CH$_2$O)$_m$H, unsubstituted phenyl, or phenyl which is substituted by halogen, $C_1$–$C_4$alkyl, $C_1$–$C_4$alkoxy or —COO($C_1$–$C_4$alkyl), or $R_7$ is phenyl-$C_1$–$C_3$alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si(R$_{20}$)(R$_{21}$)$_2$, or —SO$_2$R$_{22}$;

$R_8$ is $C_1$–$C_{12}$alkyl, $C_3$–$C_{12}$alkenyl, cyclohexyl, hydroxycyclohexyl, or $R_8$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO($C_1$–$C_4$alkyl), —OOCR$_{19}$, —COOH, —COO($C_1$–$C_8$alkyl), —CON($C_1$–$C_4$alkyl)$_2$,

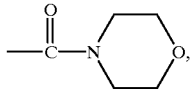

—CO($C_1$–$C_4$alkyl) or

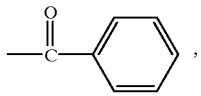

or $R_8$ is 2,3-epoxypropyl, phenyl-$C_1$–$C_3$alkyl, phenyl-$C_1$–$C_3$hydroxyalkyl, unsubstituted phenyl or phenyl which is mono- or poly-substituted by halogen, SH, $C_1$–$C_4$alkyl, $C_1$–$C_4$alkoxy or —COO($C_1$–$C_4$alkyl), or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

R₉ and R₁₀ independently of one another are hydrogen, C₁–C₁₂alkyl, C₂–C₄alkyl, which is substituted by OH, SH, C₁–C₄alkoxy, CN or —COO(C₁–C₄alkyl), or R₉ and R₁₀ independently of one another are C₃–C₅alkenyl, cyclohexyl, phenyl-C₁–C₃alkyl, unsubstituted phenyl or phenyl which is mono- or polysubstituted by C₁–C₁₂alkyl or halogen, or R₉ and R₁₀ together are C₂–C₇alkylene which can be interrupted by —O—, —S— or —N(R₁₈)—;

R₁₁ and R₁₂ independently of one another are a direct bond, —CH₂—, —CH₂CH₂—, —O—, —S—, —CO— or —N(R₆)—; provided that R₁₁ and R₁₂ are not a direct bond at the same time;

R₁₃ is hydrogen, C₁–C₈alkyl or phenyl wherein C₁–C₈alkyl or phenyl are unsubstituted or substituted by 1 to 5 SH;

R₁₄, R₁₅ and R₁₆ independently of one another are hydrogen or unsubstituted or SH-substituted C₁–C₄alkyl;

R₁₇ is hydrogen, unsubstituted or SH-substituted C₁–C₈alkyl or unsubstituted or SH-substituted phenyl;

R₁₈ is unbranched or branched C₂–C₁₆alkylene, which can be interrupted by 1 to 6 —O—, —S— or —N(R₁₇)— or substituted by 1 to 5 groups SH;

R₁₉ is C₁–C₄alkyl, C₂–C₄alkenyl or phenyl;

R₂₀ and R₂₁ independently of one another are C₁–C₄alkyl or phenyl;

R₂₂ is C₁–C₁₈alkyl, phenyl or phenyl substituted by C₁–C₁₄alkyl;

Ar₃ is phenyl, naphthyl, furyl, thienyl or pyridiyl, wherein said radicals are unsubstituted or substituted by halogen, SH, OH, C₁–C₁₂alkyl, C₁–C₄alkyl, which is substituted by OH, halogen, SH, —N(R₁₇)₂, C₁–C₁₂alkoxy, —COO(C₁–C₁₈alkyl), —CO(OCH₂CH₂)ₙOCH₃ or —OCO(C₁–C₄alkyl), or said radicals are substituted by C₁–C₁₂alkoxy, C₁–C₄alkoxy, which is substituted by —COO (C₁–C₁₈alkyl) or —CO(OCH₂CH₂)ₙOCH₃, or said radicals are substituted by —(OCH₂CH₂)ₙOH, —(OCH₂CH₂)ₙOCH₃, C₁–C₈alkylthio, phenoxy, —COO(C₁–C₁₈alkyl), —CO(OCH₂CH₂)ₙOCH₃, phenyl or benzoyl;

n is 1 to 20;

m is 2 to 20;

provided that at least one of the radicals Ar, Ar₁, Ar₂, Ar₃, R₁, R₂, R₃, R₄, R₅ or Y is substituted by 1 to 5 SH groups, or provided that Y contains at least one —SS— group; and provided that if R₃ and R₄ are morpholino and R₁ and R₂ simultaneously are methyl, Ar₁ is not phenyl substituted by SR₈, with R₈ being H or —CH₂CH₂—O—CH₂CH₂SH or CH₂CH₂CH₂SH; or an acid addition salt of a compound of the formula I, II, III or IV.

2. Compound according to claim 1 of the formula II, wherein a is 1.

3. Compound of formula I according to claim 1, wherein Ar₂ is a group

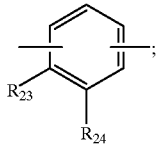

R₂₃ and R₂₄ independently of one another are hydrogen, halogen, C₁–C₁₂alkyl, cyclopentyl, cyclohexyl, phenyl, benzyl, benzoyl, OR₂₅, SH, SR₂₆, SOR₂₆, SO₂R₂₆, NR₂₇R₂₈, NHSO₂R₂₉;

R₂₅ is hydrogen, C₁–C₁₂alkyl, C₁–C₆alkyl substituted by —CN, —OH or —SH, or R₂₅ is C₁–C₄alkoxy, C₃–C₅alkenoxy, OCH₂CH₂CN, OCH₂—CH₂COOR₃₀, COOH or COOR₃₀, —(CH₂—CH₂O)ₛH, C₂–C₈alkanoyl, C₃–C₁₂alkenyl, cyclohexyl, hydroxycyclohexyl, phenyl, phenyl substituted by halogen, C₁–C₁₂alkyl or C₁–C₄alkoxy, or R₂₅ is phenyl-C₁–C₃-alkyl, or —Si(C₁–C₈-alkyl)ᵣ(phenyl)₃₋ᵣ;

s is 2–20;

r is 1, 2 or 3;

R₂₆ is C₁–C₁₂alkyl, C₁–C₆alkyl substituted by —OH, —SH, —CN, —COOR₃₀, C₁–C₄alkoxy, —OCH₂CH₂CN or —OCH₂—CH₂COOR₃₀, or R₂₆ is C₃–C₁₂alkenyl, cyclohexyl, phenyl-C₁–C₃-alkyl, phenyl, phenyl substituted by halogen, C₁–C₁₂alkyl or C₁–C₄alkoxy;

R₂₇ and R₂₈ independently of one another are hydrogen, unsubstituted or SH-substituted C₁–C₁₂alkyl, C₂–C₄hydroxyalkyl, C₂–C₁₀alkoxyalkyl, C₃–C₅alkenyl, C₅–C₁₂cycloalkyl, phenyl-C₁–C₃-alkyl, phenyl, phenyl substituted by halogen, OH, SH, C₁–C₁₂alkyl or C₁–C₄alkoxy, or R₂₇ and R₂₈ are C₂–C₃alkanoyl or benzoyl; or R₂₇ and R₂₈ together are C₂–C₈alkylene which can be interrupted by —O—, —S— or —NR₆, or together are C₂–C₈alkylene which can be substituted by —OH, C₁–C₄alkoxy or COOR₃₀;

R₆ is hydrogen, unsubstituted or OH—, SH— or HS—(CH₂)q—COO-substituted C₁–C₁₂alkyl, C₂–C₁₂alkyl, which is interrupted by —O—, —NH— or —S—, or R₆ is C₃–C₅alkenyl, phenyl-C₁–C₃-alkyl, CH₂CH₂CN, unsubstituted or OH- or SH-substituted C₁–C₄alkyl-CO—CH₂CH₂—, unsubstituted or OH- or SH-substituted C₂–C₈alkanoyl or R₆ is benzoyl;

q is 1 or 2;

R₂₉ is C₁–C₁₈alkyl, unsubstituted phenyl or naphthyl, phenyl or naphthyl substituted by halogen, C₁–C₁₂alkyl or C₁–C₈alkoxy,; and R₃₀ is unsubstituted C₁–C₄alkyl or C₁–C₄alkyl, which is substituted by OH or SH.

4. Compound of formula I according to claim 3, wherein Ar₂ is

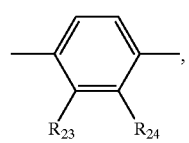

X is S and Y is Ar substituted by SR₈ or OR₇.

5. Compound of formula I according to claim 1, wherein Y is SH-substituted C₁–C₁₂alkyl, C₂–C₂₀alkyl, which is interrupted by —S— or —SS—, or Y is a SH-substituted phenyl-, biphenyl- or benzoylphenyl-group, or a group

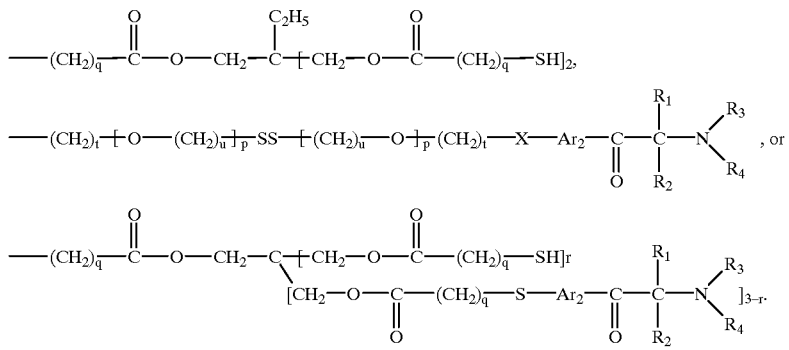

6. Compound of the formula I or II according to claim 1, wherein $R_1$ and $R_2$ independently of one another are $C_1$–$C_4$alkyl, benzyl or $C_3$–$C_6$alkenyl;

$R_3$ and $R_4$ independently of one another are $C_1$–$C_4$alkyl or $R_3$ and $R_4$ together are $C_3$–$C_7$alkylene, which is interrupted by —O—;

$Ar_1$ is phenyl substituted by $SR_8$;

$R_8$ is SH-substituted $C_1$–$C_4$alkyl or SH-substituted phenyl;

$Ar_2$ is phenylene;

X is S or NH; and

Y is $C_1$–$C_{10}$alkyl substituted by SH and/or 1 to 2 OH.

7. A composition comprising (a) at least one ethylenically unsaturated photopolymerizable compound and (b) at least one compound of the formula I, II, III or IV as defined in claim 1.

8. A composition comprising (a) a polymer or oligomer having at least two ethylenically unsaturated groups and at least one carboxyl function within the molecule structure and (b) as photoinitiator, at least one compound of the formula I, II, III or IV

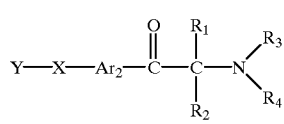

(I)

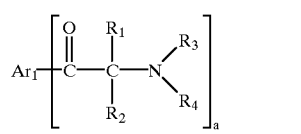

(II)

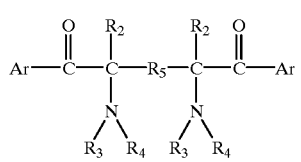

(III)

-continued

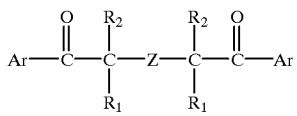

(IV)

wherein a is an integer 1, 2 or 4;

Ar is a phenyl, biphenyl or benzoylphenyl group, which is unsubstituted or substituted by 1 to 5 of the radicals halogen, $C_1$–$C_{12}$alkyl, $C_3$–$C_{12}$alkenyl, $C_5$–$C_6$cycloalkyl, phenyl-$C_1$–$C_3$alkyl, —COOH, —COO($C_1$–$C_4$alkyl), —$OR_7$, —SH, —$SR_8$, —$SOR_8$, —$SO_2R_8$, —CN, —$SO_2NH_2$, —$SO_2NH(C_1$–$C_4$alkyl), —$SO_2$—N($C_1$–$C_4$alkyl)$_2$, —$NR_9R_{10}$, —$NHCOR_9$, or by a group of the formula V,

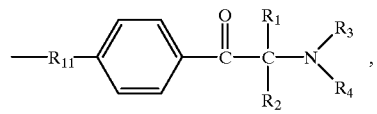

(V)

or Ar is a group of the formula VI or VII

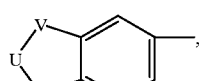

(VI)

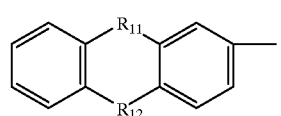

(VII)

$Ar_1$ if a is 1 has the same meanings as Ar;

if a is 2, $Ar_1$ is a divalent aromatic radical of the formula VIII or VIIIa

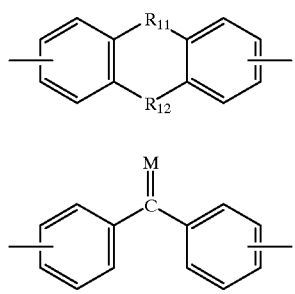 (VIII)

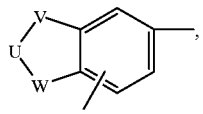 (VIa)

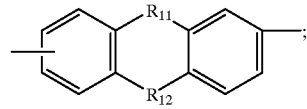 (VIIa)

if a is 4, Ar$_1$ is a tetravalent aromatic radical of the formula VIIIb

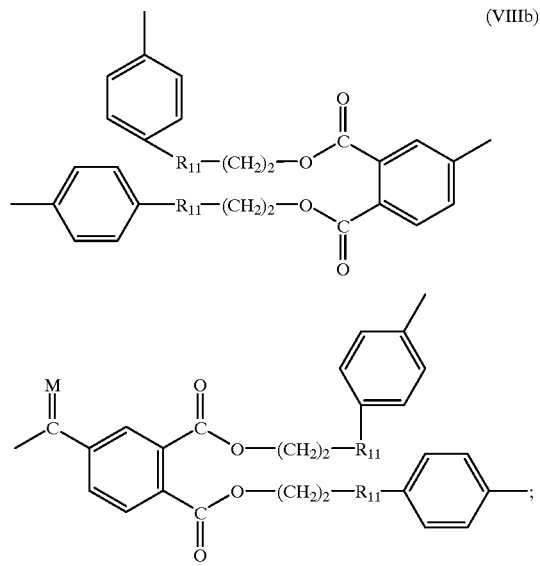

(VIIIb)

Ar$_2$ is

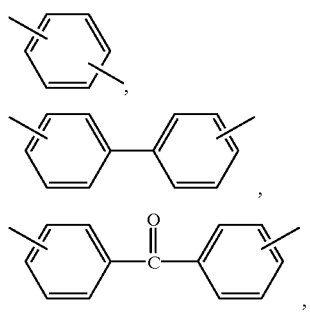

these groups are unsubstituted or substituted by 1 to 5 of the radicals halogen, C$_1$–C$_{12}$alkyl, C$_3$–C$_{12}$alkenyl, C$_5$–C$_6$cycloalkyl, phenyl-C$_1$–C$_3$alkyl, —COOH, —COO(C$_1$–C$_4$alkyl), —OR$_7$, —SH, —SR$_8$, —SOR$_8$, —SO$_2$R$_8$, —CN, —SO$_2$NH$_2$, —SO$_2$NH(C$_1$–C$_4$alkyl), —SO$_2$—N(C$_1$–C$_4$alkyl)$_2$, —NR$_9$R$_{10}$, —NHCOR$_9$, or by a group of the formula V as defined above, or Ar$_2$ is a group of the formula VIa or VIIa X is a direct bond, —O—, —S— or —N(R$_6$)—;

Y is hydrogen, C$_1$–C$_{12}$alkyl, which is unsubstituted or substituted by 1 to 5 OH, OR$_6$, COOR$_6$, SH, N(R$_6$)$_2$ or halogen or substituted 1 to 5 times by a group of the formula Ia

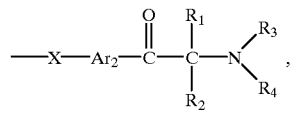 (Ia)

or Y is C$_2$–C$_{20}$alkyl, which is interrupted by 1 to 9 —O—, —N(R$_6$)—, —S—, —SS—, —X—C(=O)—, —X—C(=S)—, —C(=O)—X—, —X—C(=O)—X—, —C(=S)—X—,

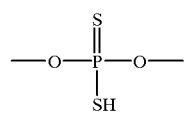

wherein the interrupted C$_2$–C$_{20}$alkyl can further be substituted by 1 to 5 SH, or Y is benzyl which is unsubstituted or substituted once or twice by —CH$_2$SH and said benzyl may further be substituted by C$_1$–C$_4$alkyl, or Y is Ar (as defined above), or a group

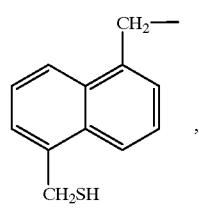

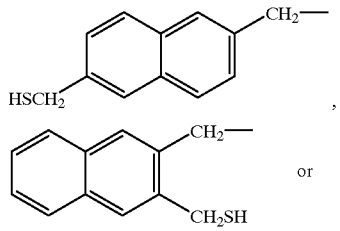

-continued

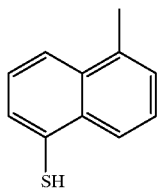

or Y is a heterocyclic 5–7 membered aliphatic or aromatic ring, comprising 1 to 4 N, O or/and S-atoms, or Y is a 8–12 membered bicyclic aliphatic or aromatic ring system, comprising 1 to 6 N, O or/and S-atoms, which mono- or bicyclic rings can further be substituted by SH or 1–5 times by a group of the formula Ia, or Y is a group

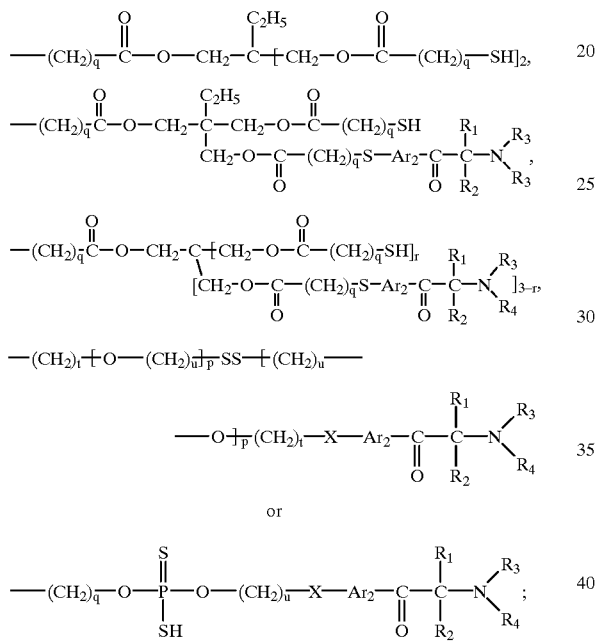

q is 1 or 2;
r is 1, 2 or 3;
p is 0 or 1;
t is 1 to 6;
u is 2 or 3;

$R_1$ and $R_2$ independently of one another are $C_1$–$C_8$alkyl, which is unsubstituted or substituted by OH, $C_1$–$C_4$alkoxy, SH, CN, —COO($C_1$–$C_8$alkyl), ($C_1$–$C_4$alkyl)-COO— or —N($R_3$)($R_4$), or $R_1$ and $R_2$ independently of one another are $C_3$–$C_6$alkenyl, phenyl, chlorophenyl, $R_7$—O-phenyl, $R_8$—S-phenyl or phenyl-$C_1$–$C_3$-alkyl, wherein said $C_3$–$C_6$alkenyl, phenyl, chlorophenyl, $R_7$—O-phenyl, $R_8$—S-phenyl or phenyl-$C_2$–$C_3$-alkyl are unsubstituted or substituted by 1 to 5 SH, or $R_1$ and $R_2$ together are unbranched or branched $C_2$–$C_9$alkylene, $C_3$–$C_9$oxaalkylene or $C_3$–$C_9$azaalkylene, wherein said $C_2$–$C_9$alkylene, $C_3$–$C_9$oxaalkylene or $C_3$–$C_9$azaalkylene are unsubstituted or substituted by 1 to 5 SH or $R_1$ and $R_2$ independently of one another are a radical of the formula IX or X

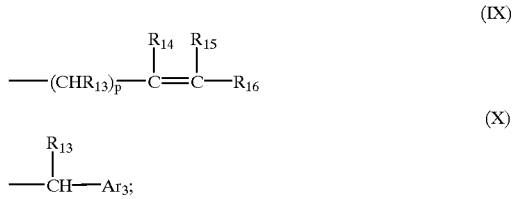

$R_3$ is hydrogen, $C_1$–$C_{12}$alkyl, $C_2$–$C_4$alkyl, which is substituted by OH, SH, $C_1$–$C_4$alkoxy, CN or —COO ($C_1$–$C_4$alkyl), or $R_3$ is $C_3$–$C_5$alkenyl, $C_5$–$C_{12}$-cycloalkyl or phenyl-$C_1$–$C_3$alkyl;

$R_4$ is $C_1$–$C_{12}$alkyl, $C_2$–$C_4$alkyl, which is substituted by OH, SH, $C_1$–$C_4$alkoxy, CN or —COO($C_1$–$C_4$alkyl), or $R_4$ is $C_3$–$C_5$alkenyl, $C_5$–$C_{12}$-cycloalkyl, phenyl-$C_1$–$C_3$alkyl, unsubstituted phenyl or phenyl, which is substituted by halogen, $C_1$–$C_{12}$alkyl, $C_1$–$C_4$alkoxy or —COO($C_1$–$C_4$alkyl);

or $R_4$ together with $R_2$ is $C_1$–$C_7$alkylene, phenyl-$C_1$–$C_4$alkylene, o-xylylene, 2-butenylene or $C_2$–$C_3$oxaalkylene or $C_2$–$C_3$azaalkylene;

or $R_3$ and $R_4$ together are $C_3$–$C_7$alkylene, which can be interrupted by —O—, —S—, —CO— or —N($R_6$)— and which $C_3$–$C_7$alkylene can be substituted by OH, $C_1$–$C_4$alkoxy or —COO($C_1$–$C_4$alkyl);

$R_5$ is $C_1$–$C_6$alkylene, xylylene, cyclohexylene, wherein said $C_1$–$C_6$alkylene, xylylene, cyclohexylene are unsubstituted or substituted by 1 to 5 SH, or $R_5$ is a direct bond;

$R_6$ is hydrogen, unsubstituted or OH—, SH— or HS—$(CH_2)_q$—COO-substituted $C_1$–$C_{12}$alkyl, $C_2$–$C_{12}$alkyl, which is interrupted by —O—, —NH— or —S—, or $R_6$ is $C_3$–$C_5$alkenyl, phenyl-$C_1$–$C_3$alkyl, $CH_2CH_2CN$, unsubstituted or OH- or SH-substituted $C_1$–$C_4$alkyl-CO—$CH_2CH_2$—, unsubstituted or OH- or SH-substituted $C_2$–$C_8$alkanoyl or $R_6$ is benzoyl;

Z is a divalent radical of the formula

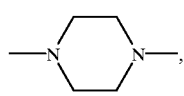

—N($R_{17}$)— or —N($R_{17}$)—$R_{18}$—N($R_{17}$)—;

U is unbranched or branched $C_1$–$C_7$alkylene;

V and W independently of one another are a direct bond, —O—, —S— or —N($R_6$)—, provided that V and W are not both a direct bond simultaneously;

M is O, S or N($R_6$);

$R_7$ is hydrogen, $C_1$–$C_{12}$alkyl, $C_3$–$C_{12}$-alkenyl, cyclohexyl, hydroxycyclohexyl, or $R_7$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO ($C_1$–$C_4$alkyl), —OOCR$_{19}$, —COOH, —COO ($C_1$–$C_8$alkyl), —CONH($C_1$–$C_4$alkyl), —CON ($C_1$–$C_4$alkyl)$_2$,

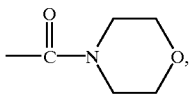

—CO($C_1$–$C_4$alkyl) or

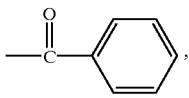

or $R_7$ is 2,3-epoxypropyl, —(CH$_2$CH$_2$O)$_m$H, unsubstituted phenyl, or phenyl which is substituted by halogen, $C_1$–$C_4$alkyl, $C_1$–$C_4$alkoxy or —COO($C_1$–$C_4$alkyl), or $R_7$ is phenyl-$C_1$–$C_3$alkyl, tetrahydropyranyl, tetrahydrofuranyl, —COOR$_{19}$, —COO($C_1$–$C_8$alkyl), —CONH($C_1$–$C_4$alkyl), —CON($C_1$–$C_8$alkyl)$_2$, —Si($R_{20}$)($R_{21}$)$_2$, or —SO$_2$R$_{22}$;

$R_8$ is $C_1$–$C_{12}$alkyl, $C_3$–$C_{12}$alkenyl, cyclohexyl, hydroxycyclohexyl, or $R_8$ is $C_1$–$C_4$alkyl, which is mono- or polysubstituted with Cl, Br, CN, SH, —N($C_1$–$C_4$alkyl)$_2$, piperidino, morpholino, OH, $C_1$–$C_4$alkoxy, —OCH$_2$CH$_2$CN, —OCH$_2$CH$_2$COO ($C_1$–$C_4$alkyl), —OOCR$_{19}$, —COOH, —COO ($C_1$–$C_8$alkyl), —CON($C_1$–$C_4$alkyl)$_2$,

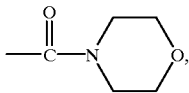

—CO($C_1$–$C_4$alkyl) or

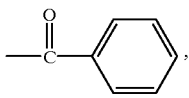

or $R_8$ is 2,3-epoxypropyl, phenyl-$C_1$–$C_3$alkyl, phenyl-$C_1$–$C_3$hydroxyalkyl, unsubstituted phenyl or phenyl which is mono- or poly-substituted by halogen, SH, $C_1$–$C_4$alkyl, $C_1$–$C_4$alkoxy or —COO($C_1$–$C_4$alkyl), or $R_8$ is 2-benzothiazyl, 2-benzimidazolyl, —CH$_2$CH$_2$—O—CH$_2$CH$_2$—SH or —CH$_2$CH$_2$—S—CH$_2$CH$_2$—SH;

$R_9$ and $R_{10}$ independently of one another are hydrogen, $C_1$–$C_{12}$alkyl, $C_2$–$C_4$alkyl, which is substituted by OH, SH, $C_1$–$C_4$alkoxy, CN or —COO($C_1$–$C_4$alkyl), or $R_9$ and $R_{10}$ independently of one another are $C_3$–$C_5$alkenyl, cyclohexyl, phenyl-$C_1$–$C_3$alkyl, unsubstituted phenyl or phenyl which is mono- or poly-substituted by $C_1$–$C_{12}$alkyl or halogen, or $R_9$ and $R_{10}$ together are $C_2$–$C_7$alkylene which can be interrupted by —O—, —S— or —N(R$_{18}$)—;

$R_{11}$ and $R_{12}$ independently of one another are a direct bond, —CH$_2$—, —CH$_2$CH$_2$—, —O—, —S—, —CO— or —N(R$_6$)—; provided that $R_{11}$ and $R_{12}$ are not a direct bond at the same time;

$R_{13}$ is hydrogen, $C_1$–$C_8$alkyl or phenyl wherein $C_1$–$C_8$alkyl or phenyl are unsubstituted or substituted by 1 to 5 SH;

$R_{14}$, $R_{15}$ and $R_{16}$ independently of one another are hydrogen or unsubstituted or SH-substituted $C_1$–$C_4$alkyl;

$R_{17}$ is hydrogen, unsubstituted or SH-substituted $C_1$–$C_8$alkyl or unsubstituted or SH-substituted phenyl;

$R_{18}$ is unbranched or branched $C_2$–$C_{16}$alkylene, which can be interrupted by 1 to 6 —O—, —S— or —N(R$_{17}$)— or substituted by 1 to 5 groups SH;

$R_{19}$ is $C_1$–$C_4$alkyl, $C_2$–$C_4$alkenyl or phenyl;

$R_{20}$ and $R_{21}$ independently of one another are $C_1$–$C_4$alkyl or phenyl;

$R_{22}$ is $C_1$–$C_{18}$alkyl, phenyl or phenyl substituted by $C_1$–$C_{14}$alkyl;

Ar$_3$ is phenyl, naphthyl, furyl, thienyl or pyridiyl, wherein said radicals are unsubstituted or substituted by halogen, SH, OH, $C_1$–$C_{12}$alkyl, $C_1$–$C_4$alkyl, which is substituted by OH, halogen, SH, —N(R$_{17}$)$_2$, $C_1$–$C_{12}$alkoxy, —COO($C_1$–$C_{18}$alkyl), —CO (OCH$_2$CH$_2$)$_n$OCH$_3$ or —OCO($C_1$–$C_4$alkyl), or said radicals are substituted by $C_1$–$C_{12}$alkoxy, $C_1$–$C_4$alkoxy, which is substituted by —COO ($C_1$–$C_{18}$alkyl) or —CO(OCH$_2$CH$_2$)$_n$OCH$_3$, or said radicals are substituted by —(OCH$_2$CH$_2$)$_n$OH, —(OCH$_2$CH$_2$)$_n$OCH$_3$, $C_1$–$C_8$alkylthio, phenoxy, —COO($C_1$–$C_{18}$alkyl), —CO(OCH$_2$CH$_2$)$_n$OCH$_3$, phenyl or benzoyl;

n is 1 to 20;

m is 2 to 20;

provided that at least one of the radicals Ar, Ar$_1$, Ar$_2$, Ar$_3$, $R_1$, $R_2$, $R_3$, $R_4$, $R_5$ or Y is substituted by 1 to 5 SH groups, or provided that Y contains at least one —SS— group; or an acid addition salt of a compound of the formula I, II, III or IV.

9. A composition according to claim 7, comprising in addition to components (a) and (b) at least one coinitiator (c).

10. A composition according to claim 8, comprising in addition to components (a) and (b) at least one coinitiator (c).

11. A composition according to claim 7, comprising in addition to components (a) and (b), and optionally (c), at least one further photoinitiator (d) and/or other additives.

12. A composition according to claim 8, comprising in addition to components (a) and (b), and optionally (c), at least one further photoinitiator (d) and/or other additives.

13. A composition according to claim 11, comprising as photoinitiator (d) a titanocene, a ferrocene, a benzophenone, a benzoin alkyl ether, a benzil ketal, a 4-aroyl-1,3-dioxolane, a dialkoxyacetophenone, an α-hydroxy- or a further α-aminoacetophenone, an α-hydroxycycloalkyl phenyl ketone, a xanthone, a thioxanthone, an anthraquinone or a mono- or bisacylphosphine oxide, or mixtures thereof.

14. A composition according to claim 12, comprising as photoinitiator (d) a titanocene, a ferrocene, a benzophenone, a benzoin alkyl ether, a benzil ketal, a 4-aroyl-1,3-dioxolane, a dialkoxyacetophenone, an α-hydroxy- or a further α-aminoacetophenone, an α-hydroxycycloalkyl phenyl ketone, a xanthone, a thioxanthone, an anthraquinone or a mono- or bisacylphosphine oxide, or mixtures thereof.

15. A composition according to claim 7, comprising in addition to components (a) and (b) at least one dye-borate compound and/or a borate salt, optionally together with an onium compound.

16. A composition according to claim 8, comprising in addition to components (a) and (b) at least one dye-borate compound and/or a borate salt, optionally together with an onium compound.

17. A composition, containing from 0.05 to 15% by weight of component (b), or, if a component (d) is present, of components (b) and (d) taken together, based on the composition.

18. A printing ink comprising a composition according to claim 7 and a pigment or a dye.

19. A printing ink comprising a composition according to claim 8 and a pigment or a dye.

20. A printing ink according to claim 18, additionally comprising a sensitizer.

21. A printing ink according to claim 19, additionally comprising a sensitizer.

22. A process for the photopolymerization of nonvolatile monomeric, oligomeric or polymeric compounds containing at least one ethylenically unsaturated double bond, which comprises adding at least one compound of the formula I, II, III or IV according to claim 1 to said compounds and irradiating the resulting composition with light having a wavelength ranging from 200 nm to 600 nm.

23. A process according to claim 22 for producing pigmented and nonpigmented paints and varnishes, for producing clear and pigmented aqueous dispersions, powder coatings, printing inks, printing plates, adhesives, dental filling compositions, waveguides, optical switches, colour proofing systems, glass fibre cable coatings, screen printing stencils, resist materials, composite compositions, for photographic reproductions, for producing masks for screen printing, for photoresists for printed electronic circuits, for encapsulating electrical and electronic components, for producing magnetic recording materials, for producing three-dimensional objects by means of stereolithography or bulk-curing, and as image recording material.

24. A coated substrate which is coated on at least one surface with a composition according to claim 7.

25. A coated substrate which is coated on at least one surface with a composition according to claim 8.

26. A process for the photographic production of relief images, which comprises subjecting a coated substrate according to claim 24 to imagewise exposure and then removing the unexposed areas with a solvent or exposing a coated substrate according to claim 24 by means of a movable laser beam (without a mask) and then removing the unexposed areas with a solvent.

27. A process for the photographic production of relief images, which comprises subjecting a coated substrate according to claim 25 to imagewise exposure and then removing the unexposed areas with a solvent or exposing a coated substrate according to claim 25 by means of a movable laser beam (without a mask) and then removing the unexposed areas with a solvent.

* * * * *

UNITED STATES PATENT AND TRADEMARK OFFICE
CERTIFICATE OF CORRECTION

PATENT NO. : 6,022,906
DATED : February 8, 2000
INVENTOR(S) : Masaki Ohwa et al.

It is certified that error appears in the above-identified patent and that said Letters Patent is hereby corrected as shown below:

On the title page, item [30], should read as follows:

-- [30] Foreign Application Priority Data

December 6, 1996 [EPO] Europe 96810854.8 --.

Signed and Sealed this

Second Day of January, 2001

Attest:

*Attesting Officer*

Q. TODD DICKINSON
*Commissioner of Patents and Trademarks*